United States Patent
Schmidt et al.

(10) Patent No.: US 9,284,301 B2
(45) Date of Patent: Mar. 15, 2016

(54) SOLUBLE GUANYLATE CYCLASE ACTIVATORS

(75) Inventors: Darby Schmidt, Arlington, MA (US); Subharekha Raghavan, Teaneck, NJ (US); John Stelmach, Westfield, NJ (US); Jian Guo, Scotch Plains, NJ (US); Jonathan Groeper, Metuchen, NJ (US); Linda Brockunier, Orange, NJ (US); Keith Rosauer, Laurence Harbor, NJ (US); Hong Shen, West Windsor, NJ (US); Rui Liang, East Brunswick, NJ (US); Fa-Xiang Ding, Staten Island, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/636,760

(22) PCT Filed: Mar. 22, 2011

(86) PCT No.: PCT/US2011/029294
§ 371 (c)(1),
(2), (4) Date: Sep. 24, 2012

(87) PCT Pub. No.: WO2011/119518
PCT Pub. Date: Sep. 29, 2011

(65) Prior Publication Data
US 2013/0012511 A1  Jan. 10, 2013

Related U.S. Application Data

(60) Provisional application No. 61/317,538, filed on Mar. 25, 2010.

(51) Int. Cl.
| | | |
|---|---|---|
| *C07D 403/14* | (2006.01) | |
| *C07D 401/14* | (2006.01) | |
| *C07D 403/04* | (2006.01) | |
| *C07D 413/14* | (2006.01) | |
| *C07D 417/14* | (2006.01) | |
| *C07D 471/04* | (2006.01) | |
| *C07D 487/04* | (2006.01) | |

(52) U.S. Cl.
CPC ............ *C07D 403/14* (2013.01); *C07D 401/14* (2013.01); *C07D 403/04* (2013.01); *C07D 413/14* (2013.01); *C07D 417/14* (2013.01); *C07D 471/04* (2013.01); *C07D 487/04* (2013.01)

(58) Field of Classification Search
CPC .. C07D 401/14; C07D 403/04; C07D 403/14; C07D 413/14; C07D 417/14; C07D 471/04; C07D 487/04
See application file for complete search history.

(56) References Cited

U.S. PATENT DOCUMENTS

| | | |
|---|---|---|
| 5,585,381 A | 12/1996 | Yanaka et al. |
| 6,162,819 A | 12/2000 | Schindler et al. |
| 6,166,027 A | 12/2000 | Straub et al. |
| 6,613,772 B1 | 9/2003 | Schindler et al. |
| 6,693,102 B2 * | 2/2004 | Stasch et al. ................. 514/256 |
| 6,743,798 B1 | 6/2004 | Straub et al. |
| 6,844,347 B1 | 1/2005 | Schnidler et al. |
| 7,045,526 B2 | 5/2006 | Schindler et al. |
| 7,115,599 B2 | 10/2006 | Stasch et al. |
| 7,173,037 B2 | 2/2007 | Alonso-Alija et al. |
| 7,666,867 B2 | 2/2010 | Makriyannis et al. |

(Continued)

FOREIGN PATENT DOCUMENTS

| | | |
|---|---|---|
| CA | 2804470 | 1/2012 |
| CA | 2804471 | 1/2012 |

(Continued)

OTHER PUBLICATIONS

Plantadosi et al, Potential Anticancer agents, Aug. 23, 1963.*

(Continued)

*Primary Examiner* — Wu-Cheng Winston Shen
*Assistant Examiner* — Jean Cornet
(74) *Attorney, Agent, or Firm* — Eric A. Meade; Catherine D. Fitch

(57) ABSTRACT

The invention relates to compounds having the structure of Formula (I) and pharmaceutically acceptable salts thereof, which are soluble guanylate cyclase activators. The compounds are capable of modulating the body's production of cyclic guanosine monophosphate ("cGMP") and are generally suitable for the therapy and prophylaxis of diseases which are associated with a disturbed cGMP balance. The compounds are useful for treatment or prevention of cardiovascular diseases, endothelial dysfunction, diastolic dysfunction, atherosclerosis, hypertension, pulmonary hypertension, angina pectoris, thromboses, restenosis, myocardial infarction, strokes, cardiac insufficiency, pulmonary hypertonia, erectile dysfunction, asthma bronchiale, chronic kidney insufficiency, diabetes, or cirrhosis of the liver.

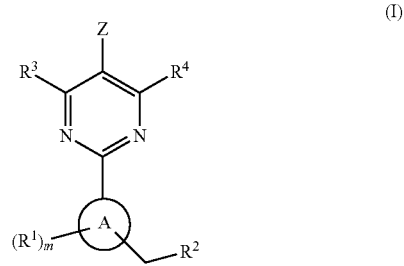

(I)

4 Claims, No Drawings

(56) References Cited

U.S. PATENT DOCUMENTS

| | | | |
|---|---|---|---|
| 8,114,400 | B2 | 2/2012 | Schirok et al. |
| 8,222,262 | B2 | 7/2012 | Eriksen et al. |
| 2004/0048866 | A1 | 3/2004 | Kolasa et al. |
| 2004/0053915 | A1 | 3/2004 | Geiss et al. |
| 2004/0121994 | A1 | 6/2004 | Anderson et al. |
| 2005/0143405 | A1 | 6/2005 | Boehringer et al. |
| 2005/0147600 | A1 | 7/2005 | Acton et al. |
| 2005/0222170 | A1 | 10/2005 | Weigand et al. |
| 2006/0014951 | A1 | 1/2006 | Feurer et al. |
| 2006/0052397 | A1 | 3/2006 | Alonso-Alija et al. |
| 2006/0106041 | A1 | 5/2006 | Kuo et al. |
| 2008/0188666 | A1 | 8/2008 | Berger et al. |
| 2008/0214641 | A1 | 9/2008 | Berger et al. |
| 2010/0029653 | A1* | 2/2010 | Schirok et al. ................ 514/245 |
| 2011/0130445 | A1 | 6/2011 | Lampe et al. |
| 2012/0022084 | A1 | 1/2012 | Follmann et al. |
| 2012/0029002 | A1 | 2/2012 | Straub et al. |
| 2013/0065884 | A1 | 3/2013 | No et al. |

FOREIGN PATENT DOCUMENTS

| | | |
|---|---|---|
| DE | 19744027 | 4/1999 |
| EP | 1339717 B1 | 9/2001 |
| EP | 1390365 B1 | 4/2002 |
| EP | 1509228 B1 | 5/2003 |
| JP | 2012/165399 | 12/2012 |
| WO | 01/83490 | 11/2001 |
| WO | WO2005046725 A1 | 5/2005 |
| WO | WO2007003435 A2 | 1/2007 |
| WO | WO2007009607 A1 | 1/2007 |
| WO | 2008031513 A1 | 3/2008 |
| WO | 2008061657 A1 | 5/2008 |
| WO | 2010/065275 | 6/2010 |
| WO | 2011/149921 | 12/2011 |

OTHER PUBLICATIONS

Compr Ther. Nov. 1982;8(11):43-52.*
Richard B. Silverman, The Organic Chemistry of Drug Design and Drug Action (Academic Press, Inc., 1992).*
Int'l Search Report of PCT/US2011/029294, mailed Jun. 1, 2011.
Int'l Preliminary Report on Patentability of PCT/US2011/029294, dated Sep. 25, 2012.
Supplementary European Search Report of EP 11 76 0012, dated Jul. 9, 2013; 8 pages.
Hering, K.W., et. al., "The design and synthesis of YC-1 analogues as probes for soluble guanylate cyclase"; Bioorg. Med. Chem. Lett, 2006, vol. 16, pp. 618-621.
Hoenick, M.J., "Purified soluble guanylyl cyclase expressed in baculovirus/sf9 system:stimulation by YC-1, nitric oxide and carbon monoxide"; J. Mol. Med., 1999, vol. 77, pp. 14-23.
Mulsch, A., et. al., "Effect of YC-1, an NO-independent, super-oxide sensitive stimulator of soluble guanylyl cyclase, on smooth muscle responsiveness to nitrovasodilators", British Journal of Pharmacology, 1997, vol. 120, pp. 681-689.
Stasch, et. al., "Pharmacological actions of a novel NO-independent guanylyl cyclase stimulator, BAY 41-8543: in vitro studies", British Journal of Pharmacology, vol. 135, 2002, pp. 333-343.
Stasch, J. P., et. al., "NO-independent regulatory site on soluble guanylate cyclase"; NATURE, vol. 410, 2001, pp. 212-215.
Stasch, J.P., et. al., "Cardiovascular actions of a novel NO-independent guanylyl cyclase stimulator, BAY 41-8543: in vivo studies", British Journal of Pharmacology, vol. 135, 2002, pp. 244-355.
Straub, A., et. al., "Metabolites of Orally Active NO-independent Pyrazolopyridine Stimulators of Soluble Guanylate Cyclase", Bioorg. Med. Chem., vol. 10, 2002, pp. 1711-1717.
Straub, A., et. al., "NO Independent stimulators of Soluble Guanylate Cyclase"; Bioorg. Med.Chem.Lett, vol. 11, 2001, pp. 781-784.

* cited by examiner

SOLUBLE GUANYLATE CYCLASE ACTIVATORS

RELATED APPLICATIONS

This application is a 35 U.S.C. §371 filing from International Application No. PCT/US2011/029294 filed Mar. 22, 2011, which claims priority to U.S. Provisional Application No. 61/317,538, filed Mar. 25, 2010.

BACKGROUND OF THE INVENTION

Cyclic GMP (cGMP) is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidie messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Active soluble guanylate cyclases are composed of an $\alpha$ and a $\beta$ subunit each. Several subunit subtypes have been described which differ from one another with respect to sequence, tissue-specific distribution and expression in different development stages. The subtypes $\alpha_1$ and $\beta_1$ are mainly expressed in brain and lung, while $\beta_2$ is found in particular in liver and kidney. The subtype $\alpha_2$ was shown to be present in human fetal brain. The subunits referred to as $\alpha_3$ and $\beta_3$ were isolated from human brain and are homologous to $\alpha_1$ and $\beta_1$. More recent works indicate an $\alpha_{2i}$ subunit which contains an insert in the catalytic domain. All subunits show great homologies in the region of the catalytic domain. The enzymes presumably contain one heme per heterodimer, which is bound via $\beta_1$-Cys-78 and/or $\beta_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thromboses, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons predominantly only have weak effects on the cGMP formation in cell lysates. D. L. Vesely, Eur. J. Clin. Invest., vol. 15, 1985, p. 258; D. L. Vesely, Biochem. Biophys. Res. Comm., vol. 88, 1979, p. 1244. A stimulation of heme-free guanylate cyclase by protoporphyrin IX was demonstrated by Ignarro et al., Adv. Pharmacol., vol. 26, 1994, p. 35. Pettibone et al., Eur. J. Pharmacol., vol. 116, 1985 p. 307, described an antihypertensive action of diphenyliodonium hexafluorophosphate and attributed this to a stimulation of sGC. According to Yu et al., Brit. J. Pharmacol, vol. 114, 1995, p. 1587, isoliquiritigenin, which has a relaxing action on isolated rat aortas, also activates sGC. Ko et al., Blood vol. 84, 1994, p. 4226, Yu et al., Biochem. J. vol. 306, 1995, p. 787, and Wu et al., Brit. J. Pharmacol. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent Application No. 908,456 and German Patent Application No. 19,744,027.

A series of 2-sulfonylaminobenzoic acid N-arylamides, the N-aryl group of which carries a thio substituent, have been mentioned in the literature. These compounds in which the N-aryl group generally carries as further substituents groups which are readily oxidizable such as, for example, two hydroxy groups being in para position with respect to one another and which in this case can be regarded as hydroquinone derivatives, are auxiliaries for the preparation of photographic materials (see, for example, Chemical Abstracts 119, 105757; 120, 41858; 123, 70224; or 126, 257007). British patent publication No. 876,526 (Chemical Abstracts 56, 15432e) discloses 3,5-dichloro-2-methylsulfonylaminobenzoic acid N-(5-chloro-2-(4-chlorophenylmercapto)-phenyl)-amide which can be used for the protection of wool against moths.

It has now been found that the compounds of the present invention effect a strong activation of guanylate cyclase and are therefore suitable for the therapy and prophylaxis of disorders which are associated with a low cGMP level.

SUMMARY OF THE INVENTION

The present invention relates to compounds which activate soluble guanylate cyclase which are valuable pharmaceutically active compounds for the therapy and prophylaxis of diseases, for example for cardiovascular diseases such as hypertension, heart failure, pulmonary hypertension, angina pectoris, diabetes, cardiac insufficiency, thromboses or atherosclerosis. The compounds of the Formula I

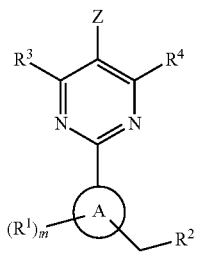

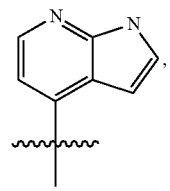 [SMILES: *c1ccnc2[nH]ccc12]

b) aryl,
c) —NR⁶C(O)R⁶,
d) —NR⁶C(O)OR⁶, or
e) —NR⁶C(O)SR⁸;

are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of the Formula I, to their use for the therapy and prophylaxis of the above mentioned diseases and for preparing pharmaceuticals for this purpose, and to pharmaceutical preparations which comprise compounds of the Formula I.

said aryl or heteroaryl being optionally substituted with one to three substituents independently selected from the group consisting of —$(CR^6_2)_n C_1$-$C_6$ alkyl, halo, —$CF_3$, —$NR^6_2$, —$NR^6C(O)OR^6$, —$S(O)_q R^8$, —$(CR^6_2)_n OR^6$, —$(CR^6_2)_n$—$C_3$-$C_{10}$ cycloalkyl, —$NR^6C(O)R^6$, aryl, heteroaryl, and —$NR^6C(O)SR^8$;

$R^1$ is —H, halo, —$OR^5$, aryl, or heteroaryl, said aryl or heteroaryl being optionally substituted with one to three substituents independently selected from the group consisting of —$C_1$-$C_6$ alkyl, —$CF_3$, and halo;

DETAILED DESCRIPTION OF THE INVENTION AND PREFERRED EMBODIMENTS

The invention concerns compounds of Formula I:

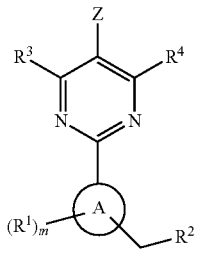

$R^2$ is

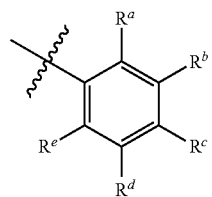

or a pharmaceutically acceptable salt thereof, wherein

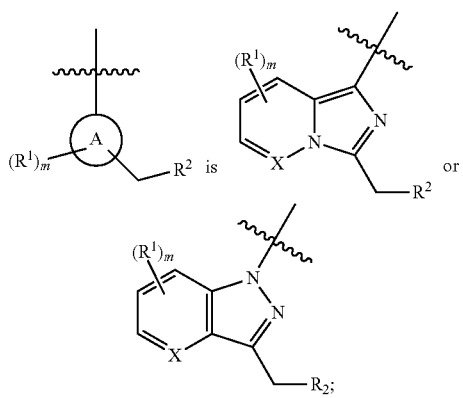

or —$C_1$-$C_6$ alkyl, said alkyl being optionally substituted with one to three substituents independently selected from the group consisting of —$C_1$-$C_6$ alkyl, —$C_{3-10}$ cycloalkyl, —$OR^6$, halo, and —$CF_3$;

$R^3$ and $R^4$ are independently selected from H or $NH_2$, wherein at least one is $NH_2$;

each $R^5$ is independently H or —$C_1$-$C_6$ alkyl;

each $R^6$ is independently H, —$C_1$-$C_6$ alkyl or —$C_{3-10}$ cycloalkyl;

$R^8$ is —$C_1$-$C_6$ alkyl;

each $R^a$, $R^b$, $R^c$, $R^d$ and $R^e$ is independently H, halo or $C_1$-$C_6$ alkyl, provided no more than two of $R^a$, $R^b$, $R^c$, $R^d$ and $R^e$ are H;

m is 0 or 1;

each n is independently 0, 1, 2, 3, 4, 5 or 6; and each q is independently 0, 1 or 2.

X is N or CH;
Z is
a) heteroaryl selected from pyrazolyl, pyridinyl, oxazolyl, morpholinyl, pyrimidinyl, pyrazinyl, imidazolyl, quinolinyl, isoxazolyl, thiazolyl and In a further embodiment, the invention is directed to compounds of Formula I having structural Formula II:

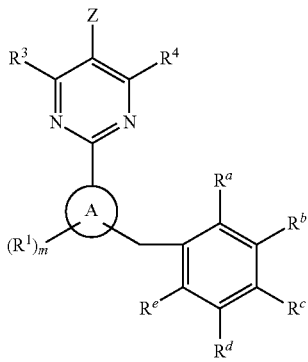

II or a pharmaceutically acceptable salt thereof, wherein
Z is
  a) heteroaryl selected from pyrazolyl, pyridinyl, oxazolyl, pyrimidinyl, pyrazinyl, imidazolyl, quinolinyl, isoxazolyl, thiazolyl and

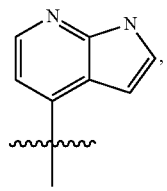

b) phenyl,
  c) —NR$^6$C(O)R$^6$,
  d) —NR$^6$C(O)OR$^6$, or
  e) —NR$^6$C(O)SRS;
said phenyl or heteroaryl being optionally substituted with one to three substituents independently selected from the group consisting of —(CR$^6{}_2$)$_n$C$_1$-C$_6$ alkyl, halo, —CF$_3$, NR$^6{}_2$, —NR$^6$C(O)OR$^6$, —S(O)$_q$R$^8$, —(CR$^6{}_2$)$_n$OR$^6$, —(CR$^6{}_2$)$_n$—C$_3$-C$_{10}$ cycloalkyl, —NR$^6$C(O)R$^6$, aryl, heteroaryl, and —NR$^6$C(O)SR$^8$;
R$^1$ is H, halo or phenyl;
each R$^a$, R$^b$, R$^c$, R$^d$ and R$^e$ is independently H or halo, provided no more than two of R$^a$, R$^b$, R$^c$, R$^d$ and R$^e$ are H; and all other variables are as previously defined in Formula I.

In another embodiment, the invention is directed to compounds of Formula IV:

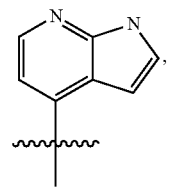 [SMILES: *c1ccnc2[nH]ccc12]

or a pharmaceutically acceptable salt thereof, wherein
Z is
  a) heteroaryl selected from pyrazolyl, pyridinyl, oxazolyl, pyrazinyl, imidazolyl, quinolinyl, isoxazolyl, thiazolyl and

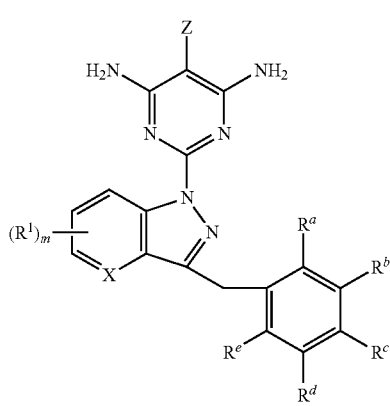

b) phenyl,
  c) —NR$^6$C(O)R$^6$,
  d) —NR$^6$C(O)OR$^6$, or
  e) —NR$^6$C(O)SR$^8$;
said phenyl or heteroaryl being optionally substituted with one to three substituents independently selected from the group consisting of —(CR$^6{}_2$)$_n$C$_1$-C$_6$ alkyl, halo, —CF$_3$, —NR$^6{}_2$, —NR$^6$C(O)OR$^6$, —S(O)$_q$R$^8$, —(CR$^6{}_2$)$_n$OR$^6$, —(CR$^6{}_2$)$_n$—C$_3$-C$_{10}$ cycloalkyl, —NR$^6$C(O)R$^6$, aryl, heteroaryl, and —NR$^6$C(O)SR$^8$;
and all other variables are as previously defined in Formula I.

In a further embodiment, the invention is directed to compounds of Formula I having structural Formula III:

III

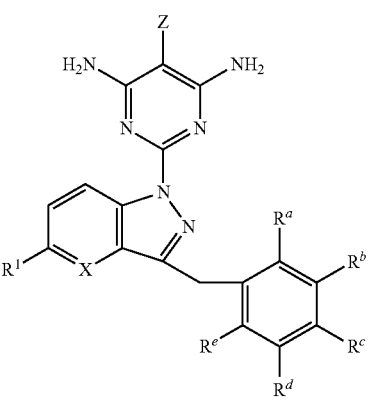

IV or a pharmaceutically acceptable salt thereof, wherein:
Z is a) heteroaryl selected from pyrazolyl or pyridinyl, said heteroaryl being optionally substituted with one to three substituents selected from the group consisting of —C$_1$-C$_6$ alkyl, halo, —CF$_3$, or —(CR$^6{}_2$)$_n$OR$^6$, or b) —NR$^6$C(O)OR$^6$;
each R$^1$ is independently H or halo;
each R$^6$ is independently H or —C$_1$-C$_6$ alkyl;
each R$^a$, R$^b$, R$^c$, R$^d$ and R$^e$ is independently H or halo, provided no more than two of R$^a$, R$^b$, R$^c$, R$^d$ and R$^e$ are H; and
each n is independently 0, 1, 2, 3, 4, 5 or 6;
and all other variables are as previously defined in Formula I.

In another embodiment of this invention are compounds wherein

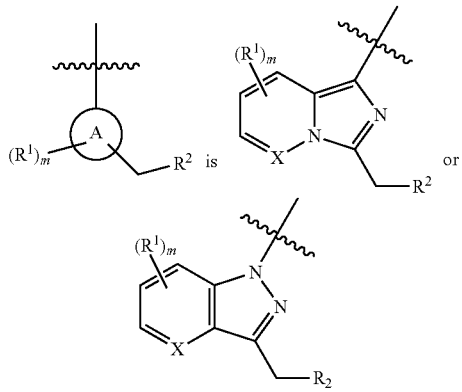

where X is CH or N. In a further embodiment

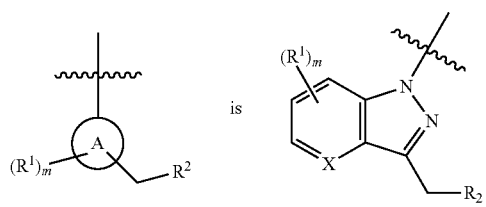

and X is CH.

In another embodiment,

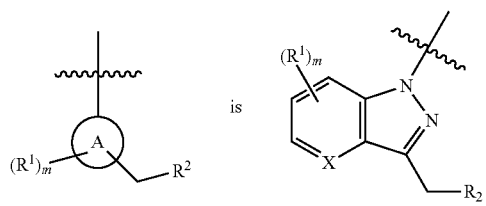

and X is N.

In another embodiment, Z is a) heteroaryl selected from pyrazolyl, pyridinyl, oxazolyl, pyrimidinyl, pyrazinyl, imidazolyl, quinolinyl, isoxazolyl, thiazolyl and

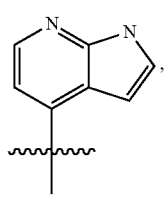 [SMILES: *c1ccnc2[nH]ccc12]

b) phenyl, c) —NR$^6$C(O)R$^6$, d) —NR$^6$C(O)OR$^6$, or e) —NR$^6$C(O)SR$^8$;

said phenyl or heteroaryl being optionally substituted with one to three substituents independently selected from the group consisting of —(CR$^6{}_2$)$_n$C$_1$-C$_6$ alkyl, halo (particularly —F or —Cl), —CF$_3$, —NR$^6{}_2$, —NR$^6$C(O)OR$^6$, —S(O)$_q$R$^8$, —(CR$^6{}_2$)$_n$OR$^6$ (particularly —OCH$_3$), —(CR$^6{}_2$)$_n$—C$_3$-C$_{10}$ cycloalkyl, —NR$^6$C(O)R$^6$, aryl (particularly phenyl), heteroaryl (particularly pyrazolyl), and —NR$^6$C(O)SR$^8$. In a further embodiment, Z is (a) an optionally substituted heteroaryl selected from pyrazolyl, pyridinyl, oxazolyl or quinolinyl, and more particularly pyrazolyl or pyridinyl, or (b) —NR$^6$C(O)OR$^6$. In a further embodiment, Z is optionally substituted with —OCH$_3$.

In another embodiment, each R$^1$ is independently H, halo, —OR$^5$, aryl (particularly wherein aryl is phenyl), or heteroaryl (particularly wherein heteroaryl is pyrazolyl), said aryl or heteroaryl being optionally substituted with one to three substituents selected from —C$_1$-C$_6$ alkyl, —CF$_3$, or halo, particularly wherein the halo is —F or —Cl. In another embodiment, each R$^1$ is independently H or halo, particularly wherein halo is —F or —Cl.

In another embodiment, R$^2$ is

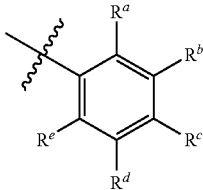

or —C$_1$-C$_6$ alkyl, said alkyl being optionally substituted with one to three substituents independently selected from —C$_1$-C$_6$ alkyl, —C$_{3-10}$ cycloalkyl, —OR$^6$, halo, or —CF$_3$. In another embodiment, R$^2$ is

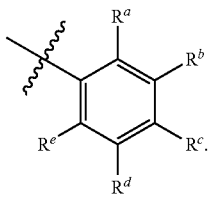

In another embodiment, R$^2$ is —C$_1$-C$_6$ alkyl, said alkyl being optionally substituted with one to three substituents independently selected from —C$_1$-C$_6$ alkyl, —C$_{3-10}$ cycloalkyl, —OR$^6$, halo, or —CF$_3$. Preferably halo is —F or —Cl.

In another embodiment, each R$^a$, R$^b$, R$^c$, R$^d$ and R$^e$ is independently H, halo (particularly —F) or —C$_1$-C$_6$ alkyl, provided no more than two of R$^a$, R$^b$, R$^c$, R$^d$ and R$^e$ are H.

In a further embodiment, each R$^a$, R$^b$, R$^c$, R$^d$ and R$^e$ is independently H or halo, provided no more than two of R$^a$, R$^b$, R$^c$, R$^d$ and R$^e$ are H.

In another embodiment, compounds of the invention are:

| EXAMPLE | IUPAC NAME |
| --- | --- |
| 2 | 2-[7-(2,3,6-trifluorobenzyl)imidazo[1,5-b]pyridazin-5-yl]-5-(1,3,5-trimethyl-1H-pyrazol-4-yl)pyrimidin-4-amine |

| EXAMPLE | IUPAC NAME |
|---|---|
| 3 | 5-[1,5-dimethyl-3-(trifluoromethyl)-1H-pyrazol-4-yl]-2-[7-(2,3,6-trifluorobenzyl)imidazo[1,5-b]pyridazin-5-yl]pyrimidin-4-amine |
| 4 | 5-(2-methylpyridin-4-yl)-2-[7-(2,3,6-trifluorobenzyl)imidazo[1,5-b]pyridazin-5-yl]pyrimidin-4-amine |
| 5 | methyl {4,6-diamino-2-[7-(2,3,6-trifluorobenzyl)imidazo[1,5-b]pyridazin-5-yl]pyrimidin-5-yl}carbamate |
| 6 | methyl {4,6-diamino-2-[7-(2,3,6-trifluorobenzyl)imidazo[1,5-b]pyridazin-5-yl]pyrimidin-5-yl}methylcarbamate |
| 7 | 5-quinolin-5-yl-2-[7-(2,3,6-trifluorobenzyl)imidazo[1,5-b]pyridazin-5-yl]pyrimidin-4-amine |
| 8 | 5-pyridin-4-yl-2-[7-(2,3,6-trifluorobenzyl)imidazo[1,5-b]pyridazin-5-yl]pyrimidin-4-amine |
| 9 | 5-pyridin-3-yl-2-[7-(2,3,6-trifluorobenzyl)imidazo[1,5-b]pyridazin-5-yl]pyrimidin-4-amine |
| 10 | 2-[7-(2,3,6-trifluorobenzyl)imidazo[1,5-b]pyridazin-5-yl]-5-[5-(trifluoromethyl)pyridin-3-yl]pyrimidin-4-amine |
| 11 | 5-(5-fluoropyridin-3-yl)-2-[7-(2,3,6-trifluorobenzyl)imidazo[1,5-b]pyridazin-5-yl]pyrimidin-4-amine |
| 12 | 5-(2-methoxypyridin-3-yl)-2-[7-(2,3,6-trifluorobenzyl)imidazo[1,5-b]pyridazin-5-yl]pyrimidin-4-amine |
| 13 | 5-(4-methylpyridin-3-yl)-2-[7-(2,3,6-trifluorobenzyl)imidazo[1,5-b]pyridazin-5-yl]pyrimidin-4-amine |
| 14 | 5-(4-methoxypyridin-3-yl)-2-[7-(2,3,6-trifluorobenzyl)imidazo[1,5-b]pyridazin-5-yl]pyrimidin-4-amine |
| 15 | 5-(1-methyl-1H-pyrazol-4-yl)-2-[7-(2,3,6-trifluorobenzyl)imidazo[1,5-b]pyridazin-5-yl]pyrimidin-4-amine |
| 16 | 5-(1-methyl-1H-pyrazol-5-yl)-2-[7-(2,3,6-trifluorobenzyl)imidazo[1,5-b]pyridazin-5-yl]pyrimidin-4-amine |
| 17 | 5-(7-fluoroquinolin-4-yl)-2-[7-(2,3,6-trifluorobenzyl)imidazo[1,5-b]pyridazin-5-yl]pyrimidin-4-amine |
| 18 | 2-[7-(2,3,6-trifluorobenzyl)imidazo[1,5-b]pyridazin-5-yl]-5-[2-(trifluoromethyl)quinolin-4-yl]pyrimidin-4-amine |
| 19 | 5-(3-fluoropyridin-4-yl)-2-[7-(2,3,6-trifluorobenzyl)imidazo[1,5-b]pyridazin-5-yl]pyrimidin-4-amine |
| 20 | 2-[7-(2,3,6-trifluorobenzyl)imidazo[1,5-b]pyridazin-5-yl]-5-[2-(trifluoromethyl)pyridin-4-yl]pyrimidin-4-amine |
| 21 | 2-[7-(2,3,6-trifluorobenzyl)imidazo[1,5-b]pyridazin-5-yl]-5-[2-(trifluoromethyl)quinolin-4-yl]pyrimidin-4-amine |
| 22 | 5-[1-methyl-3-(trifluoromethyl)-1H-pyrazol-4-yl]-2-[7-(2,3,6-trifluorobenzyl)imidazo[1,5-b]pyridazin-5-yl]pyrimidin-4-amine |
| 23 | 5-pyridin-4-yl-2-[7-(2,3,5-trifluorobenzyl)imidazo[1,5-b]pyridazin-5-yl]pyrimidin-4-amine |
| 24 | 5-pyridin-3-yl-2-[7-(2,3,5-trifluorobenzyl)imidazo[1,5-b]pyridazin-5-yl]pyrimidin-4-amine |
| 25 | 5-(4-methoxypyridin-3-yl)-2-[7-(2,3,5-trifluorobenzyl)imidazo[1,5-b]pyridazin-5-yl]pyrimidin-4-amine |
| 26 | 5-(4-methylpyridin-3-yl)-2-[7-(2,3,5-trifluorobenzyl)imidazo[1,5-b]pyridazin-5-yl]pyrimidin-4-amine |
| 27 | 5-quinolin-5-yl-2-[7-(2,3,5-trifluorobenzyl)imidazo[1,5-b]pyridazin-5-yl]pyrimidin-4-amine |
| 28 | 5-(2-methylpyridin-4-yl)-2-[7-(2,3,5-trifluorobenzyl)imidazo[1,5-b]pyridazin-5-yl]pyrimidin-4-amine |
| 29 | 2-[7-(2-chloro-3,6-difluorobenzyl)imidazo[1,5-b]pyridazin-5-yl]-5-pyridin-4-ylpyrimidin-4-amine |
| 30 | 2-[7-(2-chloro-3,6-difluorobenzyl)imidazo[1,5-b]pyridazin-5-yl]-5-(1,3,5-trimethyl-1H-pyrazol-4-yl)pyrimidin-4-amine |
| 31 | 2-[7-(2-chloro-3,6-difluorobenzyl)imidazo[1,5-b]pyridazin-5-yl]-5-(2-methylpyridin-4-yl)pyrimidin-4-amine |
| 32 | 2-[7-(2-chloro-3,6-difluorobenzyl)imidazo[1,5-b]pyridazin-5-yl]-5-quinolin-5-ylpyrimidin-4-amine |
| 33 | 2-[7-(2-chloro-3,6-difluorobenzyl)imidazo[1,5-b]pyridazin-5-yl]-5-[2-(trifluoromethyl)pyridin-4-yl]pyrimidin-4-amine |
| 34 | 2-[7-(2-chloro-3,6-difluorobenzyl)imidazo[1,5-b]pyridazin-5-yl]-5-pyridin-3-ylpyrimidin-4-amine |
| 35 | 2-[7-(2-chloro-3,6-difluorobenzyl)imidazo[1,5-b]pyridazin-5-yl]-5-(4-methoxypyridin-3-yl)pyrimidin-4-amine |
| 36 | 2-[7-(2-chloro-3,6-difluorobenzyl)imidazo[1,5-b]pyridazin-5-yl]-5-[5-(trifluoromethyl)pyridin-3-yl]pyrimidin-4-amine |
| 37 | 2-[7-(2-chloro-3,6-difluorobenzyl)imidazo[1,5-b]pyridazin-5-yl]-5-(4-methylpyridin-3-yl)pyrimidin-4-amine |
| 38 | 2-[7-(2-chloro-3,6-difluorobenzyl)imidazo[1,5-b]pyridazin-5-yl]-5-(1-methyl-1H-pyrazol-4-yl)pyrimidin-4-amine |
| 39 | 2-[7-(2-chloro-3,6-difluorobenzyl)imidazo[1,5-b]pyridazin-5-yl]-5-[1,5-dimethyl-3-(trifluoromethyl)-1H-pyrazol-4-yl]pyrimidin-4-amine |
| 40 | 2-[7-(2,3,5-trifluorobenzyl)imidazo[1,5-b]pyridazin-5-yl]-5-(1,3,5-trimethyl-1H-pyrazol-4-yl)pyrimidin-4-amine |

| EXAMPLE | IUPAC NAME |
|---|---|
| 41 | 5-[1,5-dimethyl-3-(trifluoromethyl)-1H-pyrazol-4-yl]-2-[7-(2,3,5-trifluorobenzyl)imidazo[1,5-b]pyridazin-5-yl]pyrimidin-4-amine |
| 42 | 2-[7-(3-chloro-2,6-difluorobenzyl)imidazo[1,5-b]pyridazin-5-yl]-5-(1,3,5-trimethyl-1H-pyrazol-4-yl)pyrimidin-4-amine |
| 43 | 2-[7-(2,3,5-trifluorobenzyl)imidazo[1,5-b]pyridazin-5-yl]-5-[2-(trifluoromethyl)pyridin-4-yl]pyrimidin-4-amine |
| 44 | 2-[7-(2,3,5-trifluorobenzyl)imidazo[1,5-b]pyridazin-5-yl]-5-[5-(trifluoromethyl)pyridin-3-yl]pyrimidin-4-amine |
| 45 | 5-[3-(methylsulfonyl)phenyl]-2-[7-(2,3,5-trifluorobenzyl)imidazo[1,5-b]pyridazin-5-yl]pyrimidin-4-amine |
| 46 | 2-[7-(2-chloro-3,5-difluorobenzyl)imidazo[1,5-b]pyridazin-5-yl]-5-[3-(methylsulfonyl)phenyl]pyrimidin-4-amine |
| 47 | 5-[2-(methylsulfonyl)phenyl]-2-[7-(2,3,5-trifluorobenzyl)imidazo[1,5-b]pyridazin-5-yl]pyrimidin-4-amine |
| 48 | 5-[4-(methylsulfonyl)phenyl]-2-[7-(2,3,5-trifluorobenzyl)imidazo[1,5-b]pyridazin-5-yl]pyrimidin-4-amine |
| 49 | 5-(3-methoxyphenyl)-2-[7-(2,3,5-trifluorobenzyl)imidazo[1,5-b]pyridazin-5-yl]pyrimidin-4-amine |
| 50 | 5-(2-methoxypyridin-3-yl)-2-[7-(2,3,4-trifluorobenzyl)imidazo[1,5-b]pyridazin-5-yl]pyrimidin-4-amine |
| 51 | 5-(4-methoxypyridin-3-yl)-2-[7-(2,3,4-trifluorobenzyl)imidazo[1,5-b]pyridazin-5-yl]pyrimidin-4-amine |
| 52 | 2-[7-(2,3,4-trifluorobenzyl)imidazo[1,5-b]pyridazin-5-yl]-5-[5-(trifluoromethyl)pyridin-3-yl]pyrimidin-4-amine |
| 53 | 5-pyridin-4-yl-2-[7-(2,3,4-trifluorobenzyl)imidazo[1,5-b]pyridazin-5-yl]pyrimidin-4-amine |
| 54 | 5-(1-methyl-1H-pyrazol-5-yl)-2-[7-(2,3,6-trifluorobenzyl)imidazo[1,5-b]pyridazin-5-yl]pyrimidin-4-amine |
| 55 | 5-[3-(methylsulfonyl)phenyl]-2-[7-(2,3,4-trifluorobenzyl)imidazo[1,5-b]pyridazin-5-yl]pyrimidin-4-amine |
| 56 | 2-[6-fluoro-3-(2,3,6-trifluorobenzyl)imidazo[1,5-a]pyridin-1-yl]-5-pyridin-3-ylpyrimidin-4-amine |
| 57 | 2-[6-fluoro-3-(2,3,6-trifluorobenzyl)imidazo[1,5-a]pyridin-1-yl]-5-quinolin-5-ylpyrimidin-4-amine |
| 58 | 2-[6-fluoro-3-(2,3,6-trifluorobenzyl)imidazo[1,5-a]pyridin-1-yl]-5-pyridin-4-ylpyrimidin-4-amine |
| 59 | 2-[6-fluoro-3-(2,3,6-trifluorobenzyl)imidazo[1,5-a]pyridin-1-yl]-5-(1,3,5-trimethyl-1H-pyrazol-4-yl)pyrimidin-4-amine |
| 60 | 2-[6-fluoro-3-(2,3,6-trifluorobenzyl)imidazo[1,5-a]pyridin-1-yl]-5-[5-(trifluoromethyl)pyridin-3-yl]pyrimidin-4-amine |
| 61 | 5-(5-fluoropyridin-3-yl)-2-[6-fluoro-3-(2,3,6-trifluorobenzyl)imidazo[1,5-a]pyridin-1-yl]pyrimidin-4-amine |
| 62 | 2-[6-fluoro-3-(2,3,6-trifluorobenzyl)imidazo[1,5-a]pyridin-1-yl]-5-(2-methoxypyridin-3-yl)pyrimidin-4-amine |
| 63 | 2-[6-fluoro-3-(2,3,6-trifluorobenzyl)imidazo[1,5-a]pyridin-1-yl]-5-(4-methylpyridin-3-yl)pyrimidin-4-amine |
| 64 | 2-[6-fluoro-3-(2,3,6-trifluorobenzyl)imidazo[1,5-a]pyridin-1-yl]-5-(2-methylpyridin-4-yl)pyrimidin-4-amine |
| 65 | 2-[6-fluoro-3-(2,3,6-trifluorobenzyl)imidazo[1,5-a]pyridin-1-yl]-5-(4-methoxypyridin-3-yl)pyrimidin-4-amine |
| 66 | 2-[6-fluoro-3-(2,3,6-trifluorobenzyl)imidazo[1,5-a]pyridin-1-yl]-5,5'-bipyrimidin-4-amine |
| 67 | 2-[6-fluoro-3-(2,3,6-trifluorobenzyl)imidazo[1,5-a]pyridin-1-yl]-5-(1-methyl-1H-pyrazol-4-yl)pyrimidin-4-amine |
| 68 | 2-[6-fluoro-3-(2,3,6-trifluorobenzyl)imidazo[1,5-a]pyridin-1-yl]-5-(1-methyl-1H-pyrazol-5-yl)pyrimidin-4-amine |
| 69 | 5-[1,5-dimethyl-3-(trifluoromethyl)-1H-pyrazol-4-yl]-2-[6-fluoro-3-(2,3,6-trifluorobenzyl)imidazo[1,5-a]pyridin-1-yl]pyrimidin-4-amine |
| 70 | 2-[6-fluoro-3-(2,3,6-trifluorobenzyl)imidazo[1,5-a]pyridin-1-yl]-5-[2-(trifluoromethyl)pyridin-4-yl]pyrimidin-4-amine |
| 71 | 5-(3-fluoropyridin-4-yl)-2-[6-fluoro-3-(2,3,6-trifluorobenzyl)imidazo[1,5-a]pyridin-1-yl]pyrimidin-4-amine |
| 72 | 2-[6-fluoro-3-(2,3,6-trifluorobenzyl)imidazo[1,5-a]pyridin-1-yl]-5-[2-(trifluoromethyl)quinolin-4-yl]pyrimidin-4-amine |
| 73 | 5-(6-fluoroquinolin-4-yl)-2-[6-fluoro-3-(2,3,6-trifluorobenzyl)imidazo[1,5-a]pyridin-1-yl]pyrimidin-4-amine |
| 74 | 2-[6-fluoro-3-(2,3,6-trifluorobenzyl)imidazo[1,5-a]pyridin-1-yl]-5-quinolin-4-ylpyrimidin-4-amine |
| 75 | 2-[6-fluoro-3-(2,3,6-trifluorobenzyl)imidazo[1,5-a]pyridin-1-yl]-5-[1-methyl-3-(trifluoromethyl)-1H-pyrazol-4-yl]pyrimidin-4-amine |
| 76 | 5-[5-(methoxymethyl)-1,3-dimethyl-1H-pyrazol-4-yl]-2-[7-(2,3,6-trifluorobenzyl)imidazo[1,5-b]pyridazin-5-yl]pyrimidin-4-amine |
| 77 | 2-[6-fluoro-3-(2,3,6-trifluorobenzyl)imidazo[1,5-a]pyridin-1-yl]-5-(1-methyl-1H-pyrrolo[2,3-b]pyridin-4-yl)pyrimidin-4-amine |
| 78 | 2-[6-fluoro-3-(2,3,6-trifluorobenzyl)imidazo[1,5-a]pyridin-1-yl]-5-(3-methylpyridin-4-yl)pyrimidin-4-amine |

| EXAMPLE | IUPAC NAME |
|---|---|
| 79 | 2-[6-fluoro-3-(2,3,6-trifluorobenzyl)imidazo[1,5-a]pyridin-1-yl]-5-(2-methoxypyridin-4-yl)pyrimidin-4-amine |
| 80 | 5-(3,5-dimethylisoxazol-4-yl)-2-[6-fluoro-3-(2,3,6-trifluorobenzyl)imidazo[1,5-a]pyridin-1-yl]pyrimidin-4-amine |
| 81 | 2-[6-fluoro-3-(2,3,6-trifluorobenzyl)imidazo[1,5-a]pyridin-1-yl]-5-(1-methyl-1H-imidazol-5-yl)pyrimidin-4-amine |
| 82 | 2-[6-fluoro-3-(2,3,6-trifluorobenzyl)imidazo[1,5-a]pyridin-1-yl]-5-[3-(methylsulfonyl)phenyl]pyrimidin-4-amine |
| 83 | 2-[5-chloro-3-(2,3,6-trifluorobenzyl)-1H-indazol-1-yl]-5-(1-methyl-1H-pyrazol-4-yl)pyrimidine-4,6-diamine |
| 84 | 2-[5-chloro-3-(2,3,6-trifluorobenzyl)-1H-indazol-1-yl]-2'-methyl-5,5'-bipyrimidine-4,6-diamine |
| 85 | 2-[5-chloro-3-(2,3,6-trifluorobenzyl)-1H-indazol-1-yl]-5-pyridin-4-ylpyrimidine-4,6-diamine |
| 86 | 2-[5-chloro-3-(2,3,6-trifluorobenzyl)-1H-indazol-1-yl]-5-(1-isobutyl-1H-pyrazol-4-yl)pyrimidine-4,6-diamine |
| 87 | 2-[5-chloro-3-(2,3,6-trifluorobenzyl)-1H-indazol-1-yl]-5-[1-(3-methylbutyl)-1H-pyrazol-4-yl]pyrimidine-4,6-diamine |
| 88 | 5-(1-tert-butyl-3-methyl-1H-pyrazol-4-yl)-2-[5-chloro-3-(2,3,6-trifluorobenzyl)-1H-indazol-1-yl]pyrimidine-4,6-diamine |
| 89 | 2-[5-chloro-3-(2,3,6-trifluorobenzyl)-1H-indazol-1-yl]-5-[1-(cyclopropylmethyl)-3-methyl-1H-pyrazol-4-yl]pyrimidine-4,6-diamine |
| 90 | 2-[5-chloro-3-(2,3,6-trifluorobenzyl)-1H-indazol-1-yl]-5-[5-(methoxymethyl)-1,3-dimethyl-1H-pyrazol-4-yl]pyrimidine-4,6-diamine |
| 91 | 2-[5-chloro-3-(2,3,6-trifluorobenzyl)-1H-indazol-1-yl]-5-(1,3,5-trimethyl-1H-pyrazol-4-yl)pyrimidine-4,6-diamine |
| 92 | 2-[5-chloro-3-(2,3,6-trifluorobenzyl)-1H-indazol-1-yl]-5-pyridin-3-ylpyrimidine-4,6-diamine |
| 93 | 2-[5-chloro-3-(2,3,6-trifluorobenzyl)-1H-indazol-1-yl]-5-(6-fluoropyridin-3-yl)pyrimidine-4,6-diamine |
| 94 | 2-[5-chloro-3-(2,3,6-trifluorobenzyl)-1H-indazol-1-yl]-5-[3-(methylsulfonyl)phenyl]pyrimidine-4,6-diamine |
| 95 | 2-[5-chloro-3-(2,3,6-trifluorobenzyl)-1H-indazol-1-yl]-5-(2-methylpyridin-4-yl)pyrimidine-4,6-diamine |
| 96 | 2-[5-chloro-3-(2,3,6-trifluorobenzyl)-1H-indazol-1-yl]-5-(5-fluoropyridin-3-yl)pyrimidine-4,6-diamine |
| 97 | 2-[5-chloro-3-(2,3,6-trifluorobenzyl)-1H-indazol-1-yl]-5-[1-methyl-5-(trifluoromethyl)-1H-pyrazol-4-yl]pyrimidine-4,6-diamine |
| 98 | 2-[5-chloro-3-(2,3,6-trifluorobenzyl)-1H-indazol-1-yl]-5-(5-methoxypyridin-3-yl)pyrimidine-4,6-diamine |
| 99 | 2-[5-chloro-3-(2,3,6-trifluorobenzyl)-1H-indazol-1-yl]-5-(3,5-dimethylisoxazol-4-yl)pyrimidine-4,6-diamine |
| 100 | 2-[5-chloro-3-(2,3,6-trifluorobenzyl)-1H-indazol-1-yl]-5-(2-methylpyridin-3-yl)pyrimidine-4,6-diamine |
| 101 | 2-[5-chloro-3-(2,3,6-trifluorobenzyl)-1H-indazol-1-yl]-5-(6-methylpyridin-3-yl)pyrimidine-4,6-diamine |
| 102 | 2-[5-chloro-3-(2,3,6-trifluorobenzyl)-1H-indazol-1-yl]-5-(5-methylpyridin-3-yl)pyrimidine-4,6-diamine |
| 103 | 2-[5-chloro-3-(2,3,6-trifluorobenzyl)-1H-indazol-1-yl]-5-(1-methyl-1H-pyrazol-5-yl)pyrimidine-4,6-diamine |
| 104 | 2-[5-chloro-3-(2,3,6-trifluorobenzyl)-1H-indazol-1-yl]-5-(6-methoxypyridin-3-yl)pyrimidine-4,6-diamine |
| 105 | 2-[5-chloro-3-(2,3,6-trifluorobenzyl)-1H-indazol-1-yl]-5-(2-methoxypyridin-4-yl)pyrimidine-4,6-diamine |
| 106 | 5-(2-aminopyridin-4-yl)-2-[5-chloro-3-(2,3,6-trifluorobenzyl)-1H-indazol-1-yl]pyrimidine-4,6-diamine |
| 107 | 2-[5-chloro-3-(2,3,6-trifluorobenzyl)-1H-indazol-1-yl]-5-(3,5-dimethyl-1H-pyrazol-4-yl)pyrimidine-4,6-diamine |
| 108 | methyl (4-{4,6-diamino-2-[5-chloro-3-(2,3,6-trifluorobenzyl)-1H-indazol-1-yl]pyrimidin-5-yl}pyridin-2-yl)carbamate |
| 109 | 2-[5-chloro-3-(2,3,6-trifluorobenzyl)-1H-indazol-1-yl]-5-(6-methoxypyridin-2-yl)pyrimidine-4,6-diamine |
| 110 | methyl (5-{4,6-diamino-2-[5-chloro-3-(2,3,6-trifluorobenzyl)-1H-indazol-1-yl]pyrimidin-5-yl}pyridin-2-yl)carbamate |
| 111 | 2-[5-chloro-3-(2,3,6-trifluorobenzyl)-1H-indazol-1-yl]-5-(2-methoxypyridin-3-yl)pyrimidine-4,6-diamine |
| 112 | 2-[5-chloro-3-(2,3,6-trifluorobenzyl)-1H-indazol-1-yl]-5-(3-fluoro-2-morpholin-4-ylpyridin-4-yl)pyrimidine-4,6-diamine |
| 113 | 2-[5-chloro-3-(2,3,6-trifluorobenzyl)-1H-indazol-1-yl]-5-pyrazin-2-ylpyrimidine-4,6-diamine |
| 114 | N-(5-{4,6-diamino-2-[5-chloro-3-(2,3,6-trifluorobenzyl)-1H-indazol-1-yl]pyrimidin-5-yl}pyridin-2-yl)acetamide |
| 115 | 2-[5-fluoro-3-(2,3,6-trifluorobenzyl)-1H-indazol-1-yl]-5-(2-methoxypyridin-4-yl)pyrimidine-4,6-diamine |
| 116 | 2-[5-fluoro-3-(2,3,6-trifluorobenzyl)-1H-indazol-1-yl]-5-[5-(trifluoromethyl)pyridin-3-yl]pyrimidine-4,6-diamine |

| EXAMPLE | IUPAC NAME |
|---|---|
| 117 | 2-[5-fluoro-3-(2,3,6-trifluorobenzyl)-1H-indazol-1-yl]-5-pyridin-3-ylpyrimidine-4,6-diamine |
| 118 | 5-(6-fluoropyridin-3-yl)-2-[5-fluoro-3-(2,3,6-trifluorobenzyl)-1H-indazol-1-yl]pyrimidine-4,6-diamine |
| 119 | 5-(6-aminopyridin-3-yl)-2-[5-fluoro-3-(2,3,6-trifluorobenzyl)-1H-indazol-1-yl]pyrimidine-4,6-diamine |
| 120 | 2-[5-fluoro-3-(2,3,6-trifluorobenzyl)-1H-indazol-1-yl]-5-[3-(methylsulfonyl)phenyl]pyrimidine-4,6-diamine |
| 121 | 2-[5-fluoro-3-(2,3,6-trifluorobenzyl)-1H-indazol-1-yl]-5-quinolin-5-ylpyrimidine-4,6-diamine |
| 122 | 2-[5-fluoro-3-(2,3,6-trifluorobenzyl)-1H-indazol-1-yl]-5-(2-methylpyridin-4-yl)pyrimidine-4,6-diamine |
| 123 | 3-{4,6-diamino-2-[5-fluoro-3-(2,3,6-trifluorobenzyl)-1H-indazol-1-yl]pyrimidin-5-yl}quinolin-2-ol |
| 124 | 5-(5-fluoropyridin-3-yl)-2-[5-fluoro-3-(2,3,6-trifluorobenzyl)-1H-indazol-1-yl]pyrimidine-4,6-diamine |
| 125 | 5-(2-fluoroquinolin-3-yl)-2-[5-fluoro-3-(2,3,6-trifluorobenzyl)-1H-indazol-1-yl]pyrimidine-4,6-diamine |
| 126 | 2-[5-fluoro-3-(2,3,6-trifluorobenzyl)-1H-indazol-1-yl]-5-pyridin-4-ylpyrimidine-4,6-diamine |
| 127 | 2-[5-fluoro-3-(2,3,6-trifluorobenzyl)-1H-indazol-1-yl]-5-(1,3,5-trimethyl-1H-pyrazol-4-yl)pyrimidine-4,6-diamine |
| 128 | 2-[5-fluoro-3-(2,3,6-trifluorobenzyl)-1H-indazol-1-yl]-5-[1-methyl-5-(trifluoromethyl)-1H-pyrazol-4-yl]pyrimidine-4,6-diamine |
| 129 | 2-[5-fluoro-3-(2,3,6-trifluorobenzyl)-1H-indazol-1-yl]-5-[1-methyl-3-(trifluoromethyl)-1H-pyrazol-5-yl]pyrimidine-4,6-diamine |
| 130 | 5-(3,5-dimethylisoxazol-4-yl)-2-[5-fluoro-3-(2,3,6-trifluorobenzyl)-1H-indazol-1-yl]pyrimidine-4,6-diamine |
| 131 | 2-[5-fluoro-3-(2,3,6-trifluorobenzyl)-1H-indazol-1-yl]-5-(2-methoxypyridin-4-yl)pyrimidine-4,6-diamine |
| 132 | 2-[5-fluoro-3-(2,3,6-trifluorobenzyl)-1H-indazol-1-yl]-2',4'-dimethoxy-5,5'-bipyrimidine-4,6-diamine |
| 133 | 2-[5-fluoro-3-(2,3,6-trifluorobenzyl)-1H-indazol-1-yl]-5-(2-methoxypyridin-3-yl)pyrimidine-4,6-diamine |
| 134 | 2-[5-fluoro-3-(2,3,6-trifluorobenzyl)-1H-indazol-1-yl]-5-(5-methoxypyridin-3-yl)pyrimidine-4,6-diamine |
| 135 | 2-[5-fluoro-3-(2,3,6-trifluorobenzyl)-1H-indazol-1-yl]-2'-methyl-5,5'-bipyrimidine-4,6-diamine |
| 136 | 2-[5-fluoro-3-(2,3,6-trifluorobenzyl)-1H-indazol-1-yl]-2'-methoxy-5,5'-bipyrimidine-4,6-diamine |
| 137 | 2-[5-fluoro-3-(2,3,6-trifluorobenzyl)-1H-indazol-1-yl]-5-(6-methoxypyridin-2-yl)pyrimidine-4,6-diamine |
| 138 | 5-(2,6-dimethoxypyridin-3-yl)-2-[5-fluoro-3-(2,3,6-trifluorobenzyl)-1H-indazol-1-yl]pyrimidine-4,6-diamine |
| 139 | 2-[5-fluoro-3-(2,3,6-trifluorobenzyl)-1H-indazol-1-yl]-5-(4-methoxypyridin-3-yl)pyrimidine-4,6-diamine |
| 140 | 2-[5-fluoro-3-(2,3,6-trifluorobenzyl)-1H-indazol-1-yl]-5,5'-bipyrimidine-4,6-diamine |
| 141 | 5-(4-fluoropyridin-3-yl)-2-[5-fluoro-3-(2,3,6-trifluorobenzyl)-1H-indazol-1-yl]pyrimidine-4,6-diamine |
| 142 | 2-[5-fluoro-3-(2,3,6-trifluorobenzyl)-1H-indazol-1-yl]-5-(1,3-thiazol-2-yl)pyrimidine-4,6-diamine |
| 143 | 2-[5-fluoro-3-(2,3,6-trifluorobenzyl)-1H-indazol-1-yl]-5-(4-methyl-2-phenyl-1,3-thiazol-5-yl)pyrimidine-4,6-diamine |
| 144 | N-{4,6-diamino-2-[5-fluoro-3-(2,3,6-trifluorobenzyl)-1H-indazol-1-yl]pyrimidin-5-yl}-2-methylpropanamide |
| 145 | 2-[5-fluoro-3-(2,3,6-trifluorobenzyl)-1H-indazol-1-yl]-5-(1,3-oxazol-2-yl)pyrimidine-4,6-diamine |
| 146 | 5-(2-methylpyridin-4-yl)-2-[3-(2,3,6-trifluorobenzyl)-1H-indazol-1-yl]pyrimidine-4,6-diamine |
| 147 | 5-(6-fluoropyridin-3-yl)-2-[3-(2,3,6-trifluorobenzyl)-1H-indazol-1-yl]pyrimidine-4,6-diamine |
| 148 | 2-[3-(2,3,6-trifluorobenzyl)-1H-indazol-1-yl]-5-(1,3,5-trimethyl-1H-pyrazol-4-yl)pyrimidine-4,6-diamine |
| 149 | 5-(5-fluoropyridin-3-yl)-2-[3-(2,3,6-trifluorobenzyl)-1H-indazol-1-yl]pyrimidine-4,6-diamine |
| 150 | 5-(1-methyl-1H-pyrazol-4-yl)-2-[3-(2,3,6-trifluorobenzyl)-1H-indazol-1-yl]pyrimidine-4,6-diamine |
| 151 | 5-(2-methylpyridin-4-yl)-2-[3-(2,3,6-trifluorobenzyl)-1H-indazol-1-yl]pyrimidine-4,6-diamine |
| 152 | 5-pyridin-4-yl-2-[3-(2,3,6-trifluorobenzyl)-1H-indazol-1-yl]pyrimidine-4,6-diamine |
| 153 | 5-pyridin-3-yl-2-[3-(2,3,6-trifluorobenzyl)-1H-indazol-1-yl]pyrimidine-4,6-diamine |
| 154 | 5-[1-methyl-5-(trifluoromethyl)-1H-pyrazol-4-yl]-2-[3-(2,3,6-trifluorobenzyl)-1H-indazol-1-yl]pyrimidine-4,6-diamine |

| EXAMPLE | IUPAC NAME |
|---|---|
| 155 | 5-(2-methoxypyridin-4-yl)-2-[3-(2,3,6-trifluorobenzyl)-1H-indazol-1-yl]pyrimidine-4,6-diamine |
| 156 | 5-(3,5-dimethylisoxazol-4-yl)-2-[3-(2,3,6-trifluorobenzyl)-1H-indazol-1-yl]pyrimidine-4,6-diamine |
| 157 | 5-(2-methylpyridin-3-yl)-2-[3-(2,3,6-trifluorobenzyl)-1H-indazol-1-yl]pyrimidine-4,6-diamine |
| 158 | 5-(6-methylpyridin-3-yl)-2-[3-(2,3,6-trifluorobenzyl)-1H-indazol-1-yl]pyrimidine-4,6-diamine |
| 159 | 2'-methyl-2-[3-(2,3,6-trifluorobenzyl)-1H-indazol-1-yl]-5,5'-bipyrimidine-4,6-diamine |
| 160 | 5-(3-fluoropyridin-4-yl)-2-[3-(2,3,6-trifluorobenzyl)-1H-indazol-1-yl]pyrimidine-4,6-diamine |
| 161 | 5-[6-(dimethylamino)pyridin-3-yl]-2-[3-(2,3,6-trifluorobenzyl)-1H-indazol-1-yl]pyrimidine-4,6-diamine |
| 162 | 5-(2-methoxypyridin-3-yl)-2-[3-(2,3,6-trifluorobenzyl)-1H-indazol-1-yl]pyrimidine-4,6-diamine |
| 163 | 5-(6-methoxypyridin-3-yl)-2-[3-(2,3,6-trifluorobenzyl)-1H-indazol-1-yl]pyrimidine-4,6-diamine |
| 164 | 5-(4-methyl-2-phenyl-1,3-thiazol-5-yl)-2-[3-(2,3,6-trifluorobenzyl)-1H-indazol-1-yl]pyrimidine-4,6-diamine |
| 165 | 5-pyrazin-2-yl-2-[3-(2,3,6-trifluorobenzyl)-1H-indazol-1-yl]pyrimidine-4,6-diamine |
| 166 | 5-(4-methoxypyridin-3-yl)-2-[3-(2,3,6-trifluorobenzyl)-1H-indazol-1-yl]pyrimidine-4,6-diamine |
| 167 | 5-(2,6-dimethoxypyridin-3-yl)-2-[3-(2,3,6-trifluorobenzyl)-1H-indazol-1-yl]pyrimidine-4,6-diamine |
| 168 | 5-(6-methoxypyridin-2-yl)-2-[3-(2,3,6-trifluorobenzyl)-1H-indazol-1-yl]pyrimidine-4,6-diamine |
| 169 | 5-pyridin-2-yl-2-[3-(2,3,6-trifluorobenzyl)-1H-indazol-1-yl]pyrimidine-4,6-diamine |
| 170 | 2-[5-methoxy-3-(2,3,6-trifluorobenzyl)-1H-indazol-1-yl]-5-(1-methyl-1H-pyrazol-4-yl)pyrimidine-4,6-diamine |
| 171 | 2-[5-methoxy-3-(2,3,6-trifluorobenzyl)-1H-indazol-1-yl]-5-pyridin-3-ylpyrimidine-4,6-diamine |
| 172 | 2-[5-methoxy-3-(2,3,6-trifluorobenzyl)-1H-indazol-1-yl]-5-[5-(trifluoromethyl)pyridin-3-yl]pyrimidine-4,6-diamine |
| 173 | 2-[5-methoxy-3-(2,3,6-trifluorobenzyl)-1H-indazol-1-yl]-5-(1,3,5-trimethyl-1H-pyrazol-4-yl)pyrimidine-4,6-diamine |
| 174 | 5-pyridin-4-yl-2-[3-(2,3,6-trifluorobenzyl)-1H-pyrazolo[4,3-b]pyridin-1-yl]pyrimidine-4,6-diamine |
| 175 | 5-(1-methyl-1H-pyrazol-4-yl)-2-[3-(2,3,6-trifluorobenzyl)-1H-pyrazolo[4,3-b]pyridin-1-yl]pyrimidine-4,6-diamine |
| 176 | methyl {4,6-diamino-2-[5-chloro-3-(2,3,6-trifluorobenzyl)-1H-indazol-1-yl]pyrimidin-5-yl}carbamate |
| 177 | methyl {4,6-diamino-2-[5-chloro-3-(2,3,6-trifluorobenzyl)-1H-indazol-1-yl]pyrimidin-5-yl}methylcarbamate |
| 178 | N-{4,6-diamino-2-[5-chloro-3-(2,3,6-trifluorobenzyl)-1H-indazol-1-yl]pyrimidin-5-yl}cyclopropanecarboxamide |
| 179 | S-methyl {4,6-diamino-2-[5-chloro-3-(2,3,6-trifluorobenzyl)-1H-indazol-1-yl]pyrimidin-5-yl}thiocarbamate |
| 180 | S-methyl {4,6-diamino-2-[5-fluoro-3-(2,3,6-trifluorobenzyl)-1H-indazol-1-yl]pyrimidin-5-yl}thiocarbamate |
| 181 | methyl {4,6-diamino-2-[5-fluoro-3-(2,3,6-trifluorobenzyl)-1H-indazol-1-yl]pyrimidin-5-yl}methylcarbamate |
| 182 | methyl {4,6-diamino-2-[3-(2,3,6-trifluorobenzyl)-1H-indazol-1-yl]pyrimidin-5-yl}carbamate |
| 183 | S-methyl {4,6-diamino-2-[3-(2,3,6-trifluorobenzyl)-1H-indazol-1-yl]pyrimidin-5-yl}thiocarbamate |
| 184 | methyl {4,6-diamino-2-[3-(2,3,6-trifluorobenzyl)-1H-indazol-1-yl]pyrimidin-5-yl}methylcarbamate |
| 185 | ethyl {4,6-diamino-2-[3-(2,3,6-trifluorobenzyl)-1H-indazol-1-yl]pyrimidin-5-yl}carbamate |
| 186 | methyl {4,6-diamino-2-[5-chloro-3-(2,3,5-trifluorobenzyl)-1H-indazol-1-yl]pyrimidin-5-yl}carbamate |
| 187 | S-methyl {4,6-diamino-2-[5-chloro-3-(2,3,5-trifluorobenzyl)-1H-indazol-1-yl]pyrimidin-5-yl}thiocarbamate |
| 188 | methyl {4,6-diamino-2-[5-chloro-3-(2,3,5-trifluorobenzyl)-1H-indazol-1-yl]pyrimidin-5-yl}methylcarbamate |
| 189 | methyl {4,6-diamino-2-[3-(2,3,5-trifluorobenzyl)-1H-indazol-1-yl]pyrimidin-5-yl}carbamate |
| 190 | methyl {4,6-diamino-2-[3-(2,3,5-trifluorobenzyl)-1H-indazol-1-yl]pyrimidin-5-yl}methylcarbamate |
| 191 | S-methyl {4,6-diamino-2-[3-(2,3,5-trifluorobenzyl)-1H-indazol-1-yl]pyrimidin-5-yl}methylthiocarbamate |
| 192 | ethyl {4,6-diamino-2-[3-(2,3,5-trifluorobenzyl)-1H-indazol-1-yl]pyrimidin-5-yl}carbamate |

| EXAMPLE | IUPAC NAME |
|---|---|
| 193 | ethyl {4,6-diamino-2-[3-(2,3,5-trifluorobenzyl)-1H-indazol-1-yl]pyrimidin-5-yl}methylcarbamate |
| 194 | methyl {4,6-diamino-2-[5-phenyl-3-(2,3,6-trifluorobenzyl)-1H-indazol-1-yl]pyrimidin-5-yl}methylcarbamate |
| 195 | methyl {4,6-diamino-2-[5-fluoro-3-(2,3,5-trifluorobenzyl)-1H-indazol-1-yl]pyrimidin-5-yl}carbamate |
| 196 | methyl {4,6-diamino-2-[5-fluoro-3-(2,3,5-trifluorobenzyl)-1H-indazol-1-yl]pyrimidin-5-yl}methylcarbamate |
| 197 | ethyl {4,6-diamino-2-[5-chloro-3-(2,3,6-trifluorobenzyl)-1H-indazol-1-yl]pyrimidin-5-yl}carbamate |
| 198 | ethyl {4,6-diamino-2-[5-chloro-3-(2,3,5-trifluorobenzyl)-1H-indazol-1-yl]pyrimidin-5-yl}carbamate |
| 199 | methyl {4,6-diamino-2-[5-chloro-3-(2,3,6-trifluorobenzyl)-1H-pyrazolo[4,3-b]pyridin-1-yl]pyrimidin-5-yl}carbamate |
| 200 | methyl {4,6-diamino-2-[5-chloro-3-(2,3,6-trifluorobenzyl)-1H-pyrazolo[4,3-b]pyridin-1-yl]pyrimidin-5-yl}methylcarbamate |
| 201 | methyl {4,6-diamino-2-[3-(2,3,6-trifluorobenzyl)-1H-pyrazolo[4,3-b]pyridin-1-yl]pyrimidin-5-yl}carbamate |
| 202 | methyl {4,6-diamino-2-[3-(3-chloro-2,5-difluorobenzyl)-5-fluoro-1H-indazol-1-yl]pyrimidin-5-yl}carbamate |
| 203 | methyl {4,6-diamino-2-[3-(2-chloro-3,6-difluorobenzyl)-5-fluoro-1H-indazol-1-yl]pyrimidin-5-yl}carbamate |
| 204 | methyl {4,6-diamino-2-[3-(2,6-difluoro-3-methylbenzyl)-5-fluoro-1H-indazol-1-yl]pyrimidin-5-yl}carbamate |
| 205 | S-methyl {4,6-diamino-2-[5-fluoro-3-(2,3,6-trichlorobenzyl)-1H-indazol-1-yl]pyrimidin-5-yl}thiocarbamate |
| 206 | N-{4,6-diamino-2-[5-fluoro-3-(2,3,6-trifluorobenzyl)-1H-indazol-1-yl]pyrimidin-5-yl}cyclopropanecarboxamide |
| 207 | N-{4,6-diamino-2-[3-(2,3,6-trifluorobenzyl)-1H-indazol-1-yl]pyrimidin-5-yl}cyclopropanecarboxamide |
| 208 | 2-[3-(2-cyclopentylethyl)-1H-indazol-1-yl]-5-pyridin-3-ylpyrimidine-4,6-diamine |
| 209 | 2-[3-(2-cyclopentylethyl)-1H-indazol-1-yl]-5-(1-methyl-1H-pyrazol-4-yl)pyrimidine-4,6-diamine |
| 210 | 2-[3-(2-cyclopentylethyl)-1H-indazol-1-yl]-5-(2-methylpyridin-4-yl)pyrimidine-4,6-diamine |
| 211 | 2-[3-(2-cyclopentylethyl)-1H-indazol-1-yl]-5-pyridin-4-ylpyrimidine-4,6-diamine |
| 212 | 2-[3-(2-cyclopentylethyl)-1H-indazol-1-yl]-5-(1,3,5-trimethyl-1H-pyrazol-4-yl)pyrimidine-4,6-diamine |
| 213 | 2-[3-(2-cyclopentylethyl)-1H-indazol-1-yl]-5-[5-(trifluoromethyl)pyridin-3-yl]pyrimidine-4,6-diamine |
| 214 | 2-[3-(2-cyclopentylethyl)-1H-indazol-1-yl]-5-[1-methyl-3-(trifluoromethyl)-1H-pyrazol-4-yl]pyrimidine-4,6-diamine |
| 215 | 2-[5-chloro-3-(2-cyclopentylethyl)-1H-indazol-1-yl]-5-pyridin-3-ylpyrimidine-4,6-diamine |
| 216 | 2-[5-chloro-3-(2-cyclopentylethyl)-1H-indazol-1-yl]-5-(2-methylpyridin-4-yl)pyrimidine-4,6-diamine |
| 217 | 2-[5-chloro-3-(2-cyclopentylethyl)-1H-indazol-1-yl]-5-(1-methyl-1H-pyrazol-4-yl)pyrimidine-4,6-diamine |
| 218 | 2-[5-chloro-3-(2-cyclopentylethyl)-1H-indazol-1-yl]-5-(1,3,5-trimethyl-1H-pyrazol-4-yl)pyrimidine-4,6-diamine |
| 219 | 2-{3-(2-cyclopentylethyl)-5-[5-(trifluoromethyl)pyridin-3-yl]-1H-indazol-1-yl}-5-[5-(trifluoromethyl)pyridin-3-yl]pyrimidine-4,6-diamine |
| 220 | 2-[3-(2-cyclopentylethyl)-5-fluoro-1H-indazol-1-yl]-5-pyridin-3-ylpyrimidine-4,6-diamine |
| 221 | 2-[3-(2-cyclopentylethyl)-5-fluoro-1H-indazol-1-yl]-5-(2-methylpyridin-4-yl)pyrimidine-4,6-diamine |
| 222 | 2-[3-(2-cyclopentylethyl)-5-fluoro-1H-indazol-1-yl]-5-(1-methyl-1H-pyrazol-4-yl)pyrimidine-4,6-diamine |
| 223 | 2-[3-(2-cyclopentylethyl)-5-fluoro-1H-indazol-1-yl]-5-(1,3,5-trimethyl-1H-pyrazol-4-yl)pyrimidine-4,6-diamine |
| 224 | 2-(5-chloro-3-pentyl-1H-indazol-1-yl)-5-(1-methyl-1H-pyrazol-4-yl)pyrimidine-4,6-diamine |
| 225 | 2-(5-chloro-3-pentyl-1H-indazol-1-yl)-5-(2-methylpyridin-4-yl)pyrimidine-4,6-diamine |
| 226 | 2-(5-chloro-3-pentyl-1H-indazol-1-yl)-5-(1,3,5-trimethyl-1H-pyrazol-4-yl)pyrimidine-4,6-diamine |
| 227 | 2-(3-pentyl-1H-indazol-1-yl)-5-(1,3,5-trimethyl-1H-pyrazol-4-yl)pyrimidine-4,6-diamine | or a pharmaceutically acceptable salt thereof.

In a further embodiment, a compound of the instant invention is:

| | |
|---|---|
| 76 | 5-[5-(methoxymethyl)-1,3-dimethyl-1H-pyrazol-4-yl]-2-[7-(2,3,6-trifluorobenzyl)imidazo[1,5-b]pyridazin-5-yl]pyrimidin-4-amine |
| 83 | 2-[5-chloro-3-(2,3,6-trifluorobenzyl)-1H-indazol-1-yl]-5-(1-methyl-1H-pyrazol-4-yl)pyrimidine-4,6-diamine |
| 91 | 2-[5-chloro-3-(2,3,6-trifluorobenzyl)-1H-indazol-1-yl]-5-(1,3,5-trimethyl-1H-pyrazol-4-yl)pyrimidine-4,6-diamine |
| 92 | 2-[5-chloro-3-(2,3,6-trifluorobenzyl)-1H-indazol-1-yl]-5-pyridin-3-ylpyrimidine-4,6-diamine |
| 93 | 2-[5-chloro-3-(2,3,6-trifluorobenzyl)-1H-indazol-1-yl]-5-(6-fluoropyridin-3-yl)pyrimidine-4,6-diamine |
| 96 | 2-[5-chloro-3-(2,3,6-trifluorobenzyl)-1H-indazol-1-yl]-5-(5-fluoropyridin-3-yl)pyrimidine-4,6-diamine |
| 99 | 2-[5-chloro-3-(2,3,6-trifluorobenzyl)-1H-indazol-1-yl]-5-(3,5-dimethylisoxazol-4-yl)pyrimidine-4,6-diamine |
| 100 | 2-[5-chloro-3-(2,3,6-trifluorobenzyl)-1H-indazol-1-yl]-5-(2-methylpyridin-3-yl)pyrimidine-4,6-diamine |
| 105 | 2-[5-chloro-3-(2,3,6-trifluorobenzyl)-1H-indazol-1-yl]-5-(2-methoxypyridin-4-yl)pyrimidine-4,6-diamine |
| 118 | 5-(6-fluoropyridin-3-yl)-2-[5-fluoro-3-(2,3,6-trifluorobenzyl)-1H-indazol-1-yl]pyrimidine-4,6-diamine |
| 122 | 2-[5-fluoro-3-(2,3,6-trifluorobenzyl)-1H-indazol-1-yl]-5-(2-methylpyridin-4-yl)pyrimidine-4,6-diamine |
| 124 | 5-(5-fluoropyridin-3-yl)-2-[5-fluoro-3-(2,3,6-trifluorobenzyl)-1H-indazol-1-yl]pyrimidine-4,6-diamine |
| 126 | 2-[5-fluoro-3-(2,3,6-trifluorobenzyl)-1H-indazol-1-yl]-5-pyridin-4-ylpyrimidine-4,6-diamine |
| 148 | 2-[3-(2,3,6-trifluorobenzyl)-1H-indazol-1-yl]-5-(1,3,5-trimethyl-1H-pyrazol-4-yl)pyrimidine-4,6-diamine |
| 149 | 5-(5-fluoropyridin-3-yl)-2-[3-(2,3,6-trifluorobenzyl)-1H-indazol-1-yl]pyrimidine-4,6-diamine |
| 150 | 5-(1-methyl-1H-pyrazol-4-yl)-2-[3-(2,3,6-trifluorobenzyl)-1H-indazol-1-yl]pyrimidine-4,6-diamine |
| 151 | 5-(2-methylpyridin-4-yl)-2-[3-(2,3,6-trifluorobenzyl)-1H-indazol-1-yl]pyrimidine-4,6-diamine |
| 152 | 5-pyridin-4-yl-2-[3-(2,3,6-trifluorobenzyl)-1H-indazol-1-yl]pyrimidine-4,6-diamine |
| 153 | 5-pyridin-3-yl-2-[3-(2,3,6-trifluorobenzyl)-1H-indazol-1-yl]pyrimidine-4,6-diamine |
| 154 | 5-[1-methyl-5-(trifluoromethyl)-1H-pyrazol-4-yl]-2-[3-(2,3,6-trifluorobenzyl)-1H-indazol-1-yl]pyrimidine-4,6-diamine |
| 157 | 5-(2-methylpyridin-3-yl)-2-[3-(2,3,6-trifluorobenzyl)-1H-indazol-1-yl]pyrimidine-4,6-diamine |
| 162 | 5-(2-methoxypyridin-3-yl)-2-[3-(2,3,6-trifluorobenzyl)-1H-indazol-1-yl]pyrimidine-4,6-diamine |
| 163 | 5-(6-methoxypyridin-3-yl)-2-[3-(2,3,6-trifluorobenzyl)-1H-indazol-1-yl]pyrimidine-4,6-diamine |
| 176 | methyl {4,6-diamino-2-[5-chloro-3-(2,3,6-trifluorobenzyl)-1H-indazol-1-yl]pyrimidin-5-yl}carbamate |
| 177 | methyl {4,6-diamino-2-[5-chloro-3-(2,3,6-trifluorobenzyl)-1H-indazol-1-yl]pyrimidin-5-yl}methylcarbamate |
| 181 | methyl {4,6-diamino-2-[5-fluoro-3-(2,3,6-trifluorobenzyl)-1H-indazol-1-yl]pyrimidin-5-yl}methylcarbamate |
| 184 | methyl {4,6-diamino-2-[3-(2,3,6-trifluorobenzyl)-1H-indazol-1-yl]pyrimidin-5-yl}methylcarbamate |
| 197 | ethyl {4,6-diamino-2-[5-chloro-3-(2,3,6-trifluorobenzyl)-1H-indazol-1-yl]pyrimidin-5-yl}carbamate | and the pharmaceutically acceptable salts thereof.

As used herein except where noted, "alkyl" is intended to include both branched- and straight-chain saturated aliphatic hydrocarbon groups having the specified number of carbon atoms. The term "cycloalkyl" means carbocycles containing no heteroatoms. Examples of cycloalkyl include cyclopropyl, cyclobutyl, cyclopentyl, cyclohexyl, cycloheptyl, decahydronaphthyl and the like. Commonly used abbreviations for alkyl groups are used throughout the specification, e.g. methyl may be represented by conventional abbreviations including "Me" or $CH_3$ or a symbol that is an extended bond without defined terminal group, e.g.

"", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl, "$C_{1-4}$ alkyl" means n-, iso-, sec- and t-butyl, n- and isopropyl, ethyl and methyl. If no number is specified, 1-10 carbon atoms are intended for linear or branched alkyl groups. The phrase "$C_{1-6}$ alkyl, wherein the alkyl group may be unsubstituted or substituted with 1-3 fluorine atoms" refers to alkyl groups having 0, 1, 2 or 3 fluorine atoms attached to one or more carbon atoms. The group "$CF_3$", for example, is a methyl group having three fluorine atoms attached the same carbon atom.

"Aryl" unless otherwise indicated, means mono- and bicyclic aromatic rings containing 6-12 carbon atoms. Examples of aryl include, but are not limited to, phenyl, naphthyl, indenyl and the like. "Aryl" also includes monocyclic rings fused to an aryl group. Examples include tetrahydronaphthyl, indanyl and the like. Phenyl is preferred "Heteroaryl" means an aromatic or partially aromatic heterocycle that contains at least one ring heteroatom selected from O, S and N. "Heteroaryl" thus includes heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, pyrazinyl indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heteroaryl groups, rings and ring systems containing from 3-15 atoms are included, forming 1-3 rings. Heteroaryl also includes aromatic heterocyclic groups fused to heterocycles that are non-aromatic or partially aromatic, and aromatic heterocyclic groups fused to cycloalkyl rings. Additional examples of heteroaryls include, but are not limited to, indazolyl, thienopyrazolyl, imidazopyridazinyl, pyrazolopyrazolyl, pyrazolopyridinyl, imidazopyridinyl and imidazothiazolyl. Heteroaryl also includes such groups in charged form, e.g., pyridinium.

"Heterocyclyl" or "heterocycle", unless otherwise indicated, means a 5- or 6-membered monocyclic saturated ring containing at least one heteroatom selected from N, S and O, in which the point of attachment may be carbon or nitrogen. Examples of "heterocyclyl" "heterocycle" include, but are not limited to, pyrrolidinyl, piperidinyl, piperazinyl, morpholinyl, imidazolidinyl, 2,3-dihydrofuro(2,3-b)pyridyl, benzoxazinyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). Heterocyclyl moreover includes such moieties in charged form, e.g., piperidinium.

"Halogen" or "halo", unless otherwise indicated, includes fluorine, chlorine, bromine and iodine. In one embodiment, halo is fluoro (—F) or chloro (—Cl).

By "oxo" is meant the functional group "=O" which is an oxygen atom connected to the molecule via a double bond, such as, for example, (1) "C=(O)", that is a carbonyl group; (2) "S=(O)", that is, a sulfoxide group; and (3) "N=(O)", that is, an N-oxide group, such as pyridyl-N-oxide.

Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

When any variable (e.g., $R^1$, $R^a$, etc.) occurs more than one time in any constituent or in Formula I or other generic Formulas herein, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

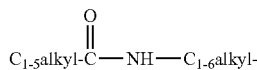

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Where a substituent or variable has multiple definitions, it is understood that the substituent or variable is defined as being selected from the group consisting of the indicated definitions.

The term "patient" includes animals, preferably mammals and especially humans, who use the instant active agents for the prohhylaxis or treatment of a medical condition.

Reference to the compounds of structural Formula I includes the compounds of other generic structural Formulas that fall within the scope of Formula I, including but not limited to Formulas II, III and IV.

Compounds of structural Formula I may contain one or more asymmetric centers and can thus occur as racemates and racemic mixtures, single enantiomers, diastereoisomeric mixtures and individual diastereoisomers. The present invention is meant to comprehend all such isomeric forms of the compounds of structural Formula I.

The present invention includes all stereoisomeric forms of the compounds of the Formula I. Centers of asymmetry that are present in the compounds of Formula I can all independently of one another have S configuration or R configuration. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of Formula I or at the stage of an intermediate during the synthesis.

Compounds of structural Formula I may be separated into their individual diastereoisomers by, for example, fractional crystallization from a suitable solvent, for example methanol or ethyl acetate or a mixture thereof, or via chiral chromatography using an optically active stationary phase. If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any stereoisomer or isomers of a compound of structural Formula I may be obtained by stereospecific synthesis using optically pure starting materials or reagents of known absolute configuration. Absolute stereochemistry may be determined by X-ray crystallography of crystalline products or crystalline intermediates which are derivatized, if necessary, with a reagent containing an asymmetric center of known absolute configuration.

For compounds of Formula I described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formula I of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural Formula I. For example, different isotopic forms of hydrogen (H) include protium ($^1$H) and deuterium ($^2$H, also denoted as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, including but not limited to the ethyl acetate solvate, and in particular, the hydrates of the compounds of structural Formula I are included in the present invention as well.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts. The terms "physiologically acceptable salt(s)" and "pharmaceutically acceptable salt(s)" are intended to have the same meaning and are used interchangeably herein.

The present invention also relates to processes for the preparation of the compounds of Formula I which are described in the following and by which the compounds of the invention are obtainable. Exemplifying the invention is the use of the compounds disclosed in the Examples and herein.

The compounds of Formula I according to the invention effect an increase of cGMP concentration via the activation of the soluble guanylate cyclase (sGC), and they are therefore useful agents for the therapy and prophylaxis of disorders which are associated with a low or decreased cGMP level or which are caused thereby, or for whose therapy or prophylaxis an increase of the present cGMP level is desired. The activation of the sGC by the compounds of the Formula I can be examined, for example, in the activity assay described below.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hypertension, and a prophylactically effective amount, e.g., for prevention of myocardial infarction.

Disorders and pathological conditions which are associated with a low cGMP level or in which an increase of the cGMP level is desired and for whose therapy and prophylaxis it is possible to use compounds of the Formula I are, for example, cardiovascular diseases, such as endothelial dysfunction, diastolic dysfunction, atherosclerosis, hypertension, heart failure, pulmonary hypertension which includes pulmonary arterial hypertension (PAH), stable and unstable angina pectoris, thromboses, restenoses, myocardial infarction, strokes, cardiac insufficiency or pulmonary hypertonia, or, for example, erectile dysfunction, asthma bronchiale, chronic kidney insufficiency and diabetes. Compounds of the Formula I can additionally be used in the therapy of cirrhosis of the liver and also for improving a restricted memory performance or ability to learn.

The invention also relates to the use of compounds of the invention for the preparation of a medicament for the treatment and/or prophylaxis of the above-mentioned diseases.

The compounds of the Formula I and their pharmaceutically acceptable salts can be administered to animals, preferably to mammals, and in particular to humans, as pharmaceuticals by themselves, in mixtures with one another or in the form of pharmaceutical preparations. A subject of the present invention therefore also are the compounds of the Formula I and their pharmaceutically acceptable salts for use as pharmaceuticals, their use for activating soluble guanylate cyclase, for normalizing a disturbed cGMP balance and in particular their use in the therapy and prophylaxis of the abovementioned syndromes as well as their use for preparing medicaments for these purposes.

Furthermore, a subject of the present invention are pharmaceutical preparations (or pharmaceutical compositions) which comprise as active component an effective dose of at least one compound of the Formula I and/or a pharmaceutically acceptable salt thereof and a customary pharmaceutically acceptable carrier, i.e., one or more pharmaceutically acceptable carrier substances and/or additives.

Thus, a subject of the invention are, for example, said compound and its pharmaceutically acceptable salts for use as a pharmaceutical, pharmaceutical preparations which comprise as active component an effective dose of said compound and/or a pharmaceutically acceptable salt thereof and a customary pharmaceutically acceptable carrier, and the uses of said compound and/or a pharmaceutically acceptable salt thereof in the therapy or prophylaxis of the abovementioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of Formula I and/or its pharmaceutically acceptable salts in the pharmaceutical preparations normally is from 0.2 to 200 mg, preferably from 1 to 200 mg, per dose, but depending on the type of the pharmaceutical preparation it can also be higher. The pharmaceutical preparations usually comprise 0.5 to 90 percent by weight of the compounds of Formula I and/or their pharmaceutically acceptable salts. The preparation of the pharmaceutical preparations can be carried out in a manner known per se. For this purpose, one or more compounds of Formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formula I or of a pharmaceutically acceptable salt thereof to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose. A single daily dose is preferred.

Compositions containing a compound of Formula I described herein will provide immediate release of the drug after administration as that term is understood in the art, but the compositions can be formulated to modify the release rate to achieve controlled, extended or delayed release and the like (collectively referred to herein as controlled release). Controlled release dosage forms can be prepared by methods known to those skilled in the art, for example, by granule or tablet enteric coatings or by admixture of a controlled release matrix component in the composition. For example, a fixed-dose combination composition containing a compound of Formula I admixed with one or more additional pharmaceutically active agents may have an immediate release or controlled release tablet dissolution profile.

The compounds of the Formula I activate soluble guanylate cyclase. On account of this property, apart from use as pharmaceutically active compounds in human medicine and veterinary medicine, they can also be employed as a scientific tool or as an aid for biochemical investigations in which such an effect on soluble guanylate cyclase is intended, and also for diagnostic purposes, for example in the in vitro diagnosis of cell samples or tissue samples. The compounds of Formula I and salts thereof can furthermore be employed, as already mentioned above, as intermediates for the preparation of other pharmaceutically active compounds.

One or more additional pharmacologically active agents may be administered in combination with a compound of Formula I. An additional active agent (or agents) is intended to mean a pharmaceutically active agent (or agents) different from the compound of Formula I. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan, valsartan, candesartan, olmesartan, telmesartan) neutral endopeptidase inhibitors (e.g., thiorphan and phosphoramidon), aldosterone antagonists, renin inhibitors (e.g. urea derivatives of di- and tripeptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, atorvastatin, rosuvastatin, pravastatin ezetimibe), niacin in immediate-release or controlled release forms, and particularly in niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide.

Examples of other active ingredients that may be administered in combination with a compound of Formula I, and either administered separately or in the same pharmaceutical composition, include, but are not limited to: (a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, LY-818, and compounds disclosed in WO02/08188, WO2004/020408, and WO2004/020409; (b) biguanides, such as metformin and phenformin; (c) protein tyrosine phosphatase-1B (PIP-1B) inhibitors; (d) dipeptidyl peptidase-IV (DPP-4) inhibitors, such as sitagliptin, saxagliptin, vildagliptin, and alogliptin; (e) insulin or insulin mimetics; (f) sulfonylureas such as tolbutamide, glimepiride, glipizide, and related materials; (g) α-glucosidase inhibitors (such as acarbose); (h) agents which improve a patient's lipid profile, such as (1) HMG-CoA reductase inhibitors (lovastatin, simvastatin, rosuvastatin, pravastatin, fluvastatin, atorvastatin, rivastatin, itavastatin, ZD-4522 and other statins), (2) bile acid sequestrants (cholestyramine, colestipol, and dialkylaminoalkyl derivatives of a cross-linked dextran), (3) niacin receptor agonists, nicotinyl alcohol, nicotinic acid, or a salt thereof, (4) PPARα agonists, such as fenofibric acid derivatives (gemfibrozil, clofibrate, fenofibrate and bezafibrate), (5) cholesterol absorption inhibitors, such as ezetimibe, (6) acyl CoA:cholesterol acyltransferase (ACAT) inhibitors, such as avasimibe, (7) CETP inhibitors, such as torcetrapib, and (8) phenolic antioxidants, such as probucol; (i) PPARα/γ dual agonists, such as muraglitazar, tesaglitazar, farglitazar, and JT-501; (j) PPARδ agonists, such as those disclosed in WO97/28149; (k) anti-obesity compounds, such as fenfluramine, dexfenfluramine, phentiramine, subitramine, orlistat, neuropeptide Y Y5 inhibitors, MC4R agonists, cannabinoid receptor 1 (CB-1) antagonists/inverse agonists (e.g., rimonabant and taranabant), and $\beta_3$ adrenergic receptor agonists; (l) ileal bile acid transporter inhibitors; (m) agents intended for use in inflammatory conditions, such as aspirin, non-steroidal anti-inflammatory drugs, glucocorticoids, azulfidine, and cyclooxygenase-2 (Cox-2) selective inhibitors; (n) glucagon receptor antagonists; (o) GLP-1; (p) GIP-1; (q) GLP-1 analogs and derivatives, such as exendins, (e.g., exenatide and liruglatide), and (r) 11β-hydroxysteroid dehydrogenase-1 (HSD-1) inhibitors.

The compounds of Formula I can be synthesized in accordance with the general schemes provided below where the substituents (i.e. $R^1$, $R^2$, X, etc.) are defined as above (unless otherwise indicated), taking into account the specific examples that are provided.

The following examples are provided so that the invention might be more fully understood. Unless otherwise indicated, the starting materials are commercially available. They should not be construed as limiting the invention in any way.

In one embodiment of the present invention compounds with the structure I. (A-D) may be prepared by the sequence depicted in Scheme 1.

SCHEME 1

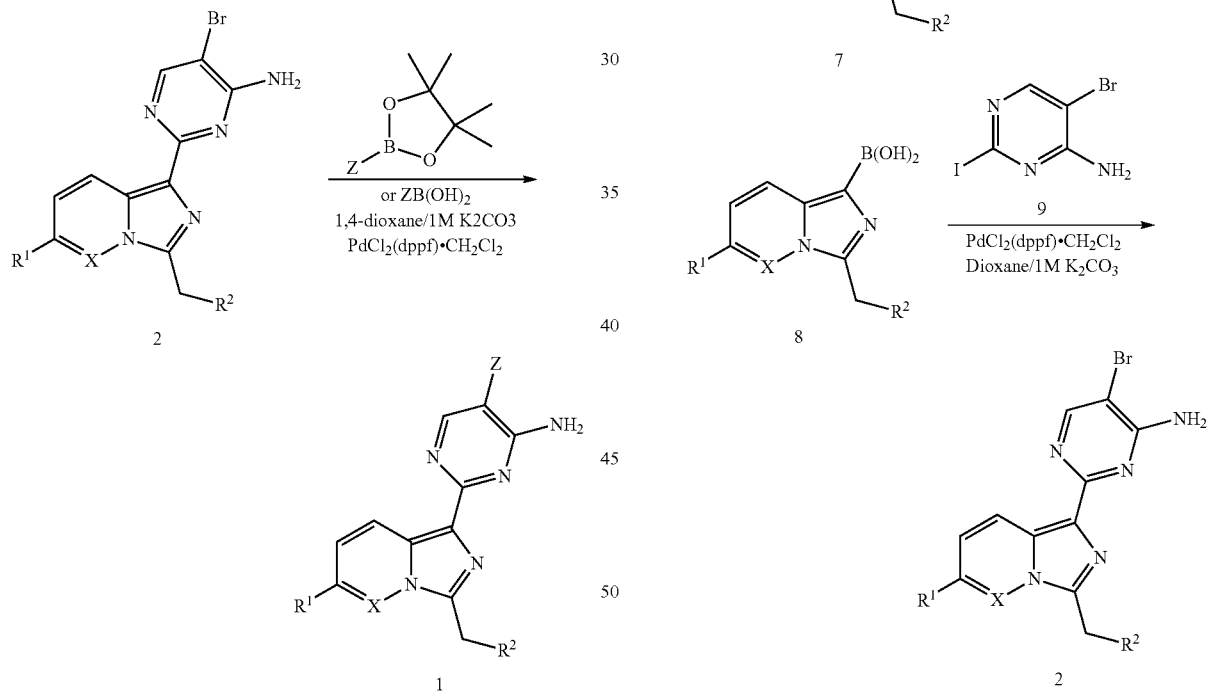

A: $R^1$ = H, X = N
B: $R^1$ = H, X = CH
C: $R^1$ = F, X = CH
D: $R^1$ = Cl, X = CH

The bromide 2 can be converted to the desired product 1 by cross-coupling to a suitable boronic acid or boronate ester under standard Suzuki reaction conditions in the presence of a suitable catalyst such as dichlorobis[1,1'-bis(diphenylphosphino)ferrocene]palladium (II) dichloromethane adduct, 1,1'-Bis(di-tert-butykphosphino)ferrocene palladium dichloride and a suitable solvent such as 1,4-dioxane and a base such as 1M potassium carbonate.

SCHEME 2

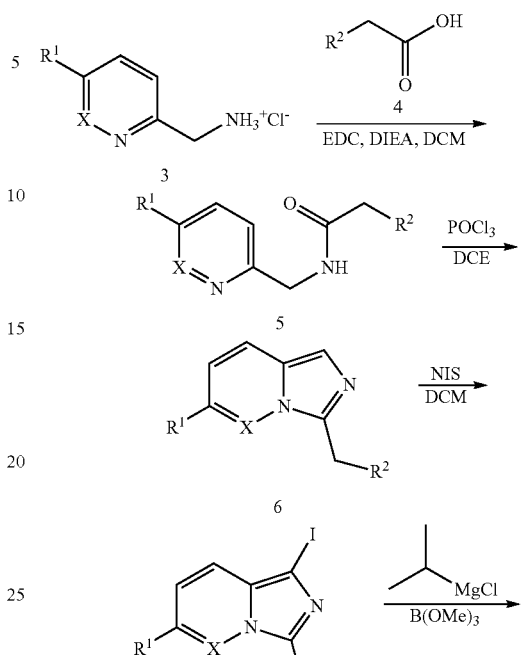

Scheme 2 outlines the preparation of the bromide intermediate 2 (A-D). The amino methyl compound 3 can be coupled with the carboxylic acid 4 using a coupling reagent such as EDC and an organic base such as DIEA or TEA in a solvent like DCM to afford the amide 5. This can be converted to the imidazopyridine 6 with phosphorous oxy-chloride in a chlorinated solvent such as DCE under refluxing conditions. Iodination of 6 to afford 7 can be accomplished with NIS in solvents like DCM or acetonitrile at ambient temperature or under reflux conditions. The iodide 7 can be converted to the boronic acid 8 using standard conditions of magnesium halogen exchange with a suitable Grignard reagent such as isopropyl magnesium chloride in a suitable solvent such as THF followed by treatment with a trialkoxy borate such as trimethyl borate. Hydrolysis of the boronate ester to the desired boronic acid 8 can be accomplished with 2N HCl. The boronic acid 8 can be coupled to the iodide 9 (see Scheme 5 for preparation) via a Suzuki reaction in the presence of a catalyst such as dichlorobis[1,1'-bis(diphenylphosphino)ferrocene] palladium (II) dichloromethane adduct, 1,1'-Bis(di-tert-butylphosphino)ferrocene palladium dichloride and a suitable solvent such as 1,4-dioxane and a base such as 1M $K_2CO_3$ to afford the desired product 2.

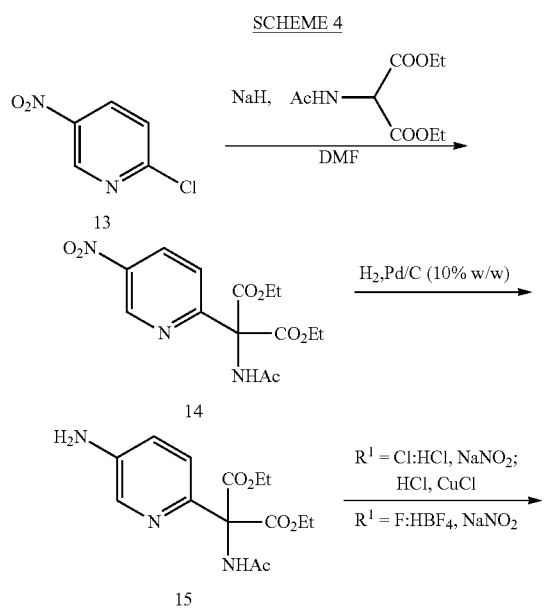

The amino methyl compound 3A may be prepared as outlined in Scheme 3. Pyridazine 10 can be converted to 2-cyano pyridazine 12 using the chemistry described by Dostal, W. and Heinisch, G. *Heterocycles* 1986, 793. Reduction of the nitrile 12 can be accomplished under high pressure hydrogenation conditions using a suitable catalyst such as palladium on carbon in an alcoholic solvent such as methanol or ethanol and a suitable acid such as hydrochloric acid to afford the 2-amino methylpyridazine hydrochloride 3A,

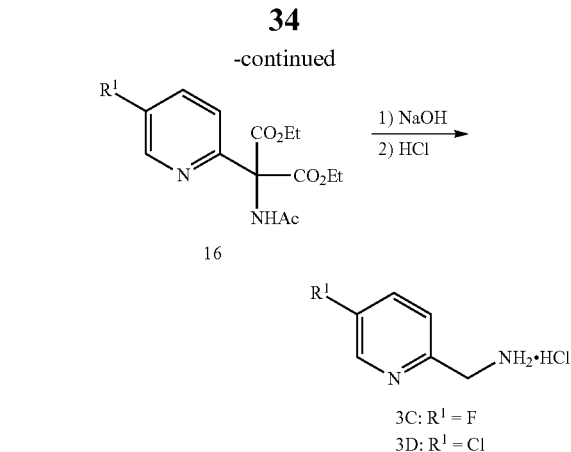

The amino methyl compounds 3C and 3D may be prepared as outlined in Scheme 4. Addition of diethyl acetamidomalonate to 2-chloro-5-nitropyridine 13 affords compound 14. Reduction of 14 with hydrogen and palladium on carbon gives the amine 15. Sandmeyer reaction of 15 using the indicated conditions gives the halo (chloro or fluoro) pyridine 16. Saponification of 16 with base followed by treatment with hydrochloric acid gives amino methyl compounds 3C and 3D.

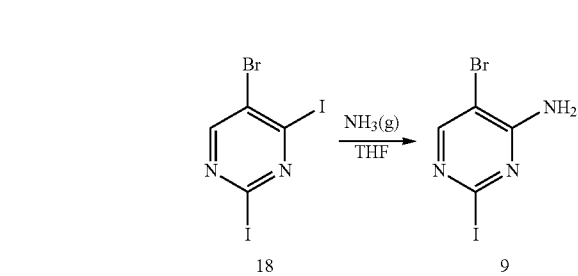

Scheme 2 outlines the synthesis of the intermediate 9. Thus, commercially available 2,4-dichloro-4-bromo pyrimidine 17 can be converted to the di-iodide 185 in the presence of excess hydroiodic acid in a suitable solvent such as DCM using the conditions described by Goodby, J. W. et. al. *J. Chem. Soc. Chem. Commun* 1996 (24) 2719. The iodide 18 can be converted to the 4-amino-pyrimidine 9 by bubbling ammonia gas in a solvent such as THF to afford the desired product.

In one embodiment of the present invention compounds with the structure 19 may be prepared by the sequence depicted in Scheme 6.

SCHEME 6

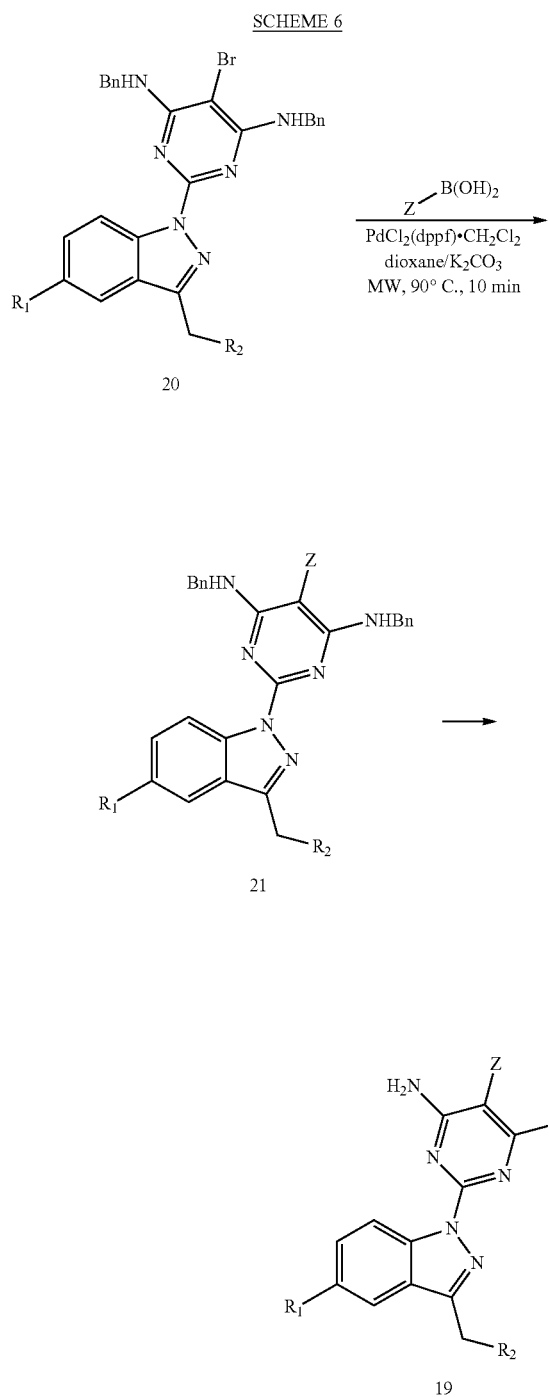

SCHEME 7

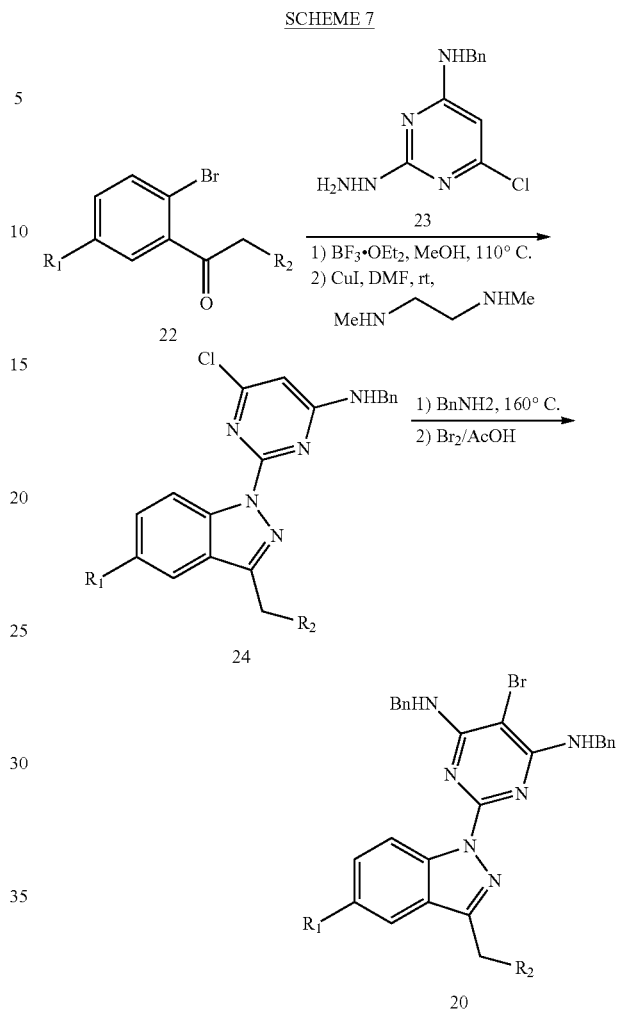

The bromide 20 can be converted to the desired product 21 by cross-coupling to a suitable boronic acid under standard Suzuki reactions conditions in the presence of a catalyst such as dichlorobis[1,1'-bis(diphenylphosphino)ferrocene]palladium (II) dichloromethane adduct, 1,1'-Bis(di-tert-butylphosphino)ferrocene palladium dichloride and a suitable solvent such as 1,4-dioxane and a base such as 1M $K_2CO_3$. Removal of the benzyl groups can be accomplished by treatment with a suitable acid such as concentrated sulfuric acid or trifluoromethane sulfonic acid to afford the desired product 19.

The preparation of the bromide intermediate 20 is outlined in Scheme 7. Treatment of the ketone 22 with the hydrazine 23 (see Scheme 9 for preparation) in the presence of a Lewis acid such as $BF_3.OEt_2$ in an alcoholic solvent like methanol or ethanol affords the hydrazone which upon treatment with copper (I) iodide and a suitable ligand such as ethylene dimethyl amine or 1,2-dicylohexyl amine affords the indazole 24. Conversion of 24 to 20 can be accomplished by treatment with benzylamine at high temperature followed by bromination using methods by those skilled in the art. One such method involves the reaction of the pyrimidine with bromine in acetic acid to afford 20.

The ketone 22 may be prepared using methods familiar to those skilled in the art. One method is depicted in Scheme 8.

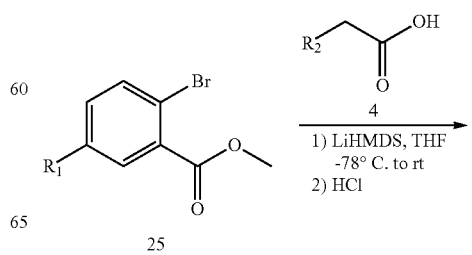

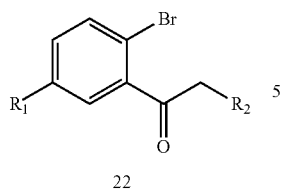

22

The di-anion of a suitable acetic acid can be generated by treatment with excess of a suitable base such as LiHMDS or NaHMDS. Treatment of the di-anion with 2-bromo methyl benzoate 25 followed by acid hydrolysis affords the ketone 22.

SCHEME 9

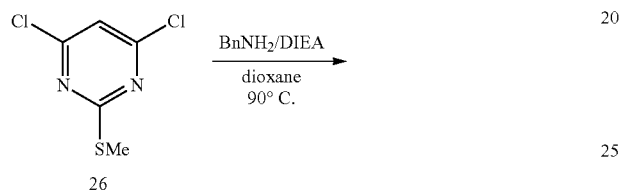

SCHEME 10

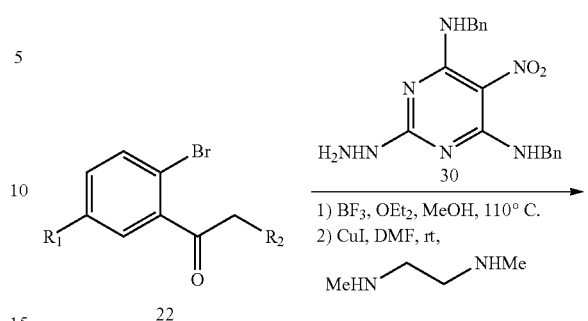

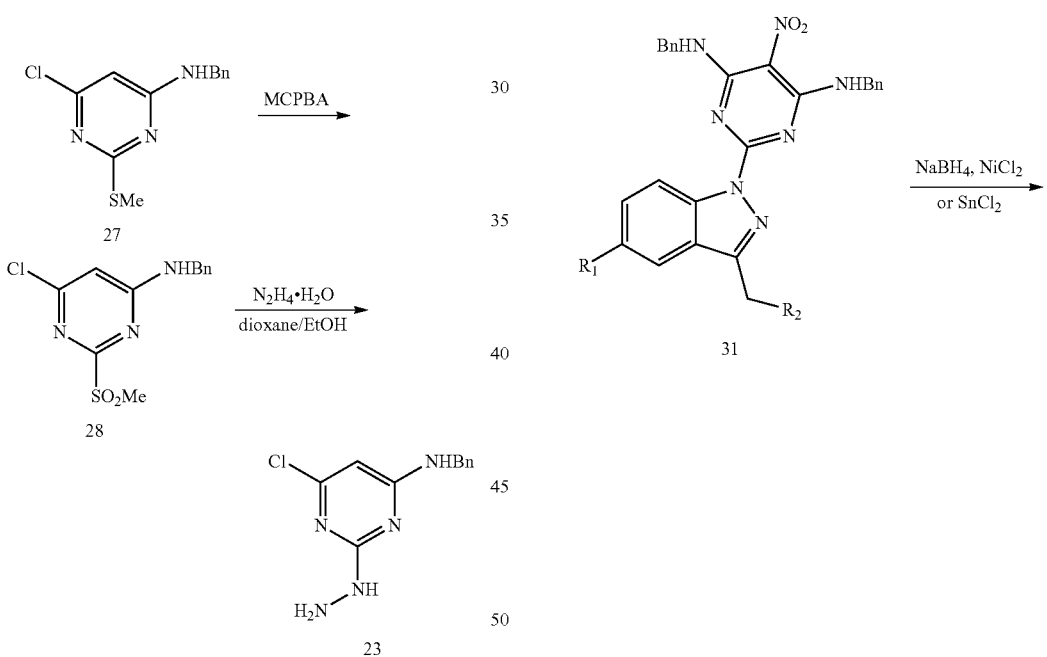

The preparation of the hydrazine intermediate 23 is outlined in Scheme 9. Treatment of 26 with a suitable amine such as benzyl amine in the presence of base like DIEA or TEA and a solvent such as 1,4-dioxane affords the mono benzylated pyrimidine 27. Oxidation of the methyl sulfide to the sulfone 28 can be accomplished using excess of a suitable oxidizing agent such mCPBA in a solvent like DCM. Finally, displacement of the sulfone 28 with hydrazine hydrate in an alcoholic solvent such as ethanol or methanol affords the desired product 23.

In one embodiment of the present invention compounds with the structure 29 may be prepared by the sequence depicted in Scheme 10.

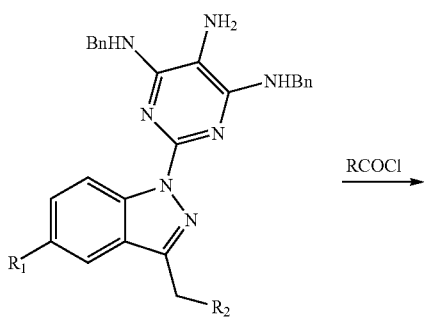

32

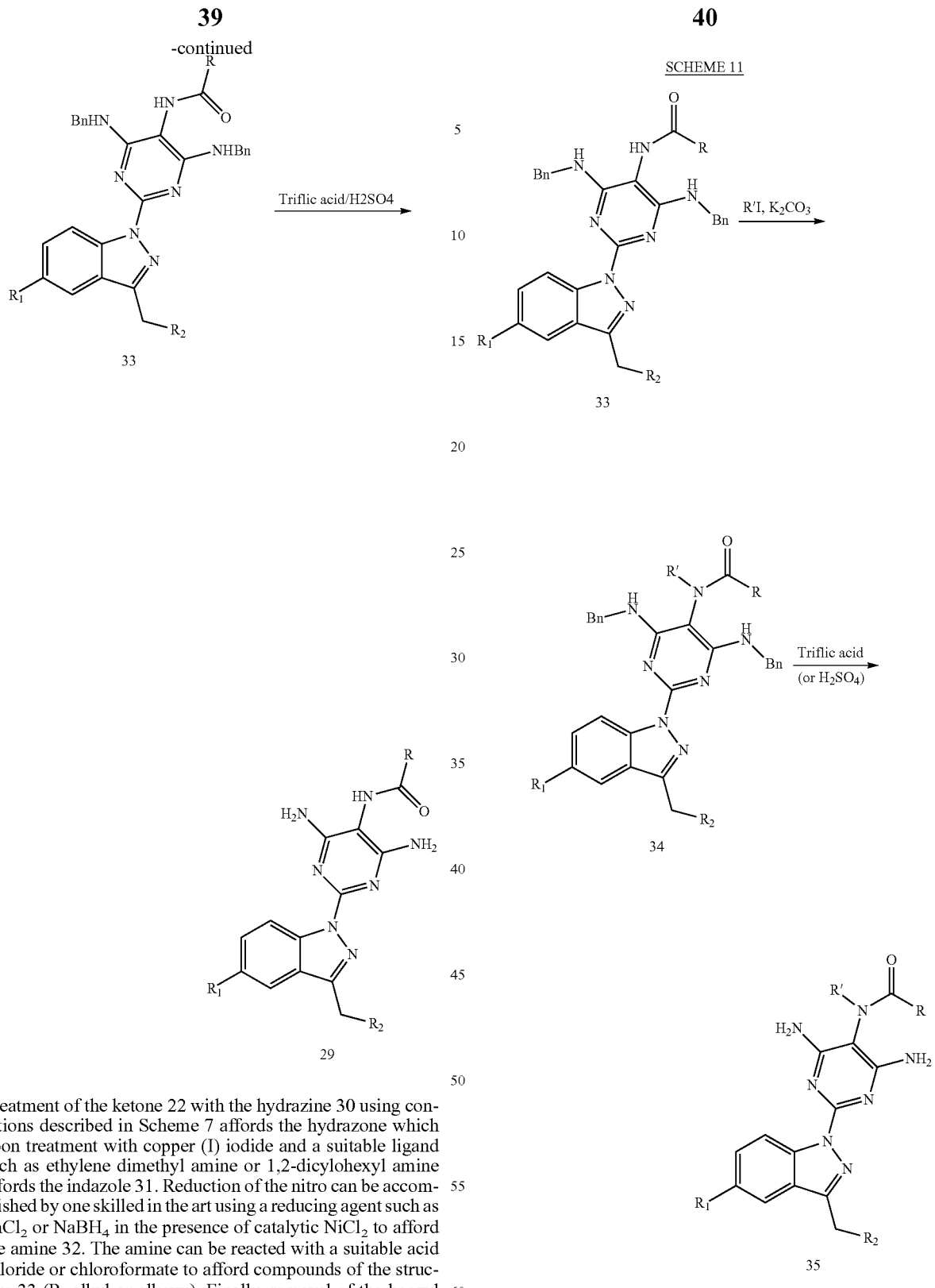

SCHEME 11

Treatment of the ketone 22 with the hydrazine 30 using conditions described in Scheme 7 affords the hydrazone which upon treatment with copper (I) iodide and a suitable ligand such as ethylene dimethyl amine or 1,2-dicylohexyl amine affords the indazole 31. Reduction of the nitro can be accomplished by one skilled in the art using a reducing agent such as $SnCl_2$ or $NaBH_4$ in the presence of catalytic $NiCl_2$ to afford the amine 32. The amine can be reacted with a suitable acid chloride or chloroformate to afford compounds of the structure 33 (R=alkyl or alkoxy). Finally, removal of the benzyl groups can be accomplished by treatment with a suitable acid such as concentrated sulfuric acid or trifluoromethane sulfonic acid (also known as triflic acid) to give the desired products of structure 29.

In one embodiment of the present invention compounds with the structure 35 may be prepared by the sequence depicted in Scheme 11.

Conversion of intermediate 33 to 34 can be accomplished by treatment with a suitable alkyl iodide such as methyl iodide in the presence of an inorganic base such as potassium carbonate in a solvent such as acetone at 50° C. Removal of the benzyl groups can be accomplished by treatment as described in Scheme 10 to afford the desired products of structure 35.

SCHEME 12

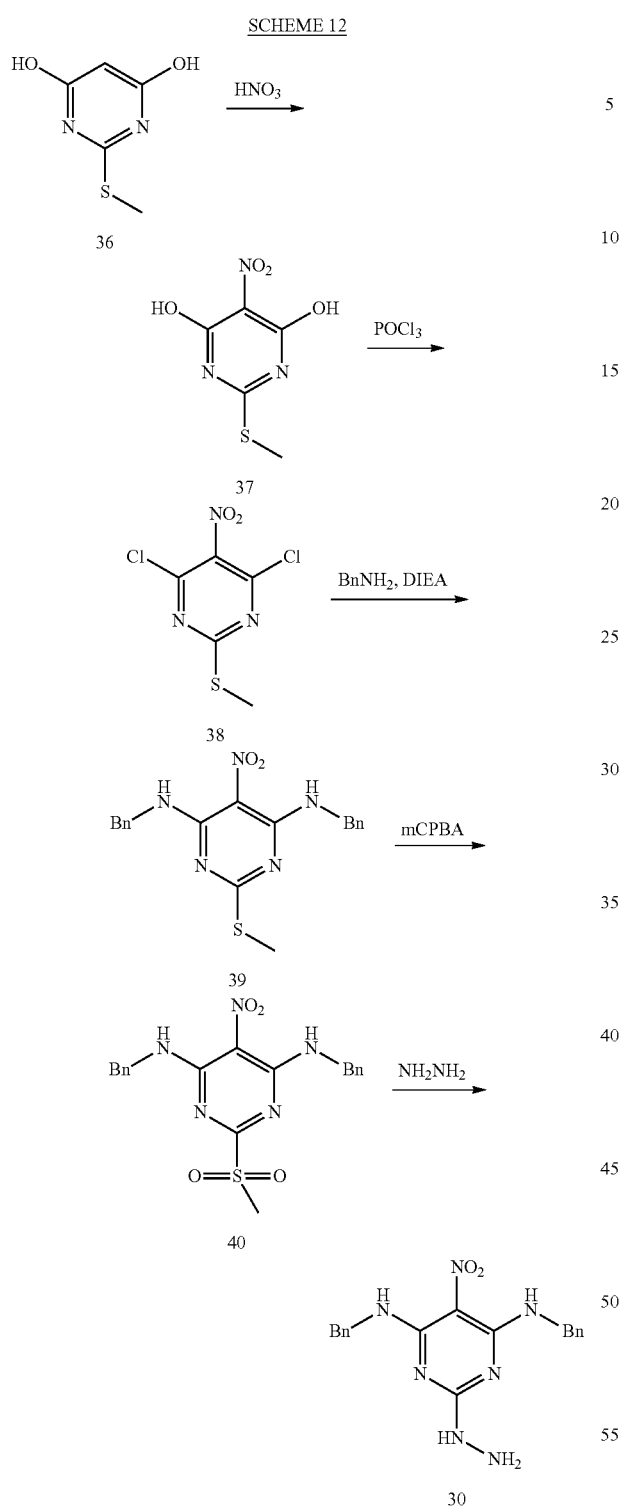

be accomplished using excess of a suitable oxidizing agent such mCPBA in a solvent like DCM. Displacement of the sulfone 40 with hydrazine hydrate in an alcoholic solvent such as ethanol or methanol affords the desired product 30.

In one embodiment of the present invention compounds with the structure 47 may be prepared by the sequence depicted in Scheme 13.

SCHEME 13

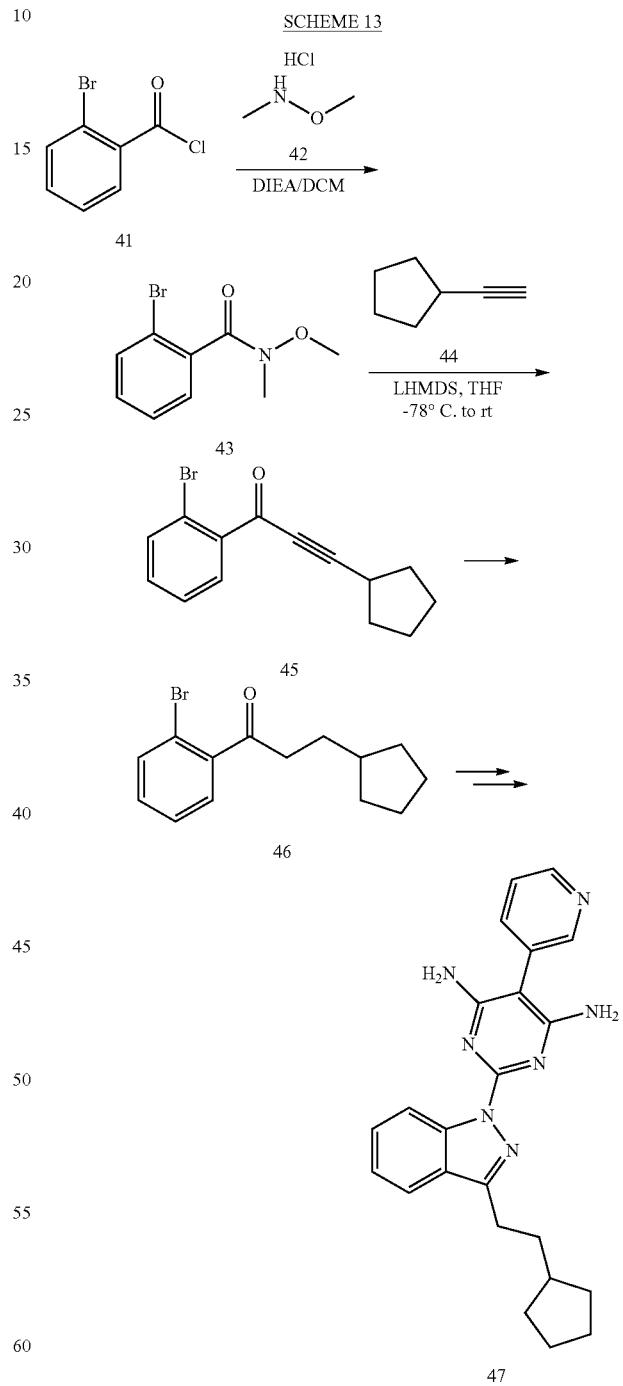

Scheme 12 outlines the preparation of the hydrazine intermediate 30. Thus, the commercially available pyrimidine 36 can be converted to the 5-nitro pyrimidine 37 using standard conditions with nitric acid. Conversion to 38 can be accomplished by treatment with phosphorous oxy-chloride. The intermediate 38 can be converted 39 by treatment with excess benzyl amine in the presence of a suitable organic base such as DIEA. Oxidation of the methyl sulfide to the sulfone 40 can Thus, treatment of a suitable acid chloride such as 2-bromo benzoyl chloride 41 with N,O-dimethyl hydroxyl amine hydrochloride affords the amide 43 which can converted to the ketoalkyne 45 by reacting with a suitably substituted acetylene such as cyclopentyl acetylene 44 in the presence of a strong base such as LiHMDS or LDA. Reduction of the triple bond can be accomplished by one skilled in the art using standard catalytic hydrogenation methods. One such method involves the use of platinum (IV) oxide as a catalyst in a non-alcoholic solvent such as ethyl acetate to afford 46. The ketone 46 is elaborated to the compound 47 using the methods described in Scheme 6.

The following examples are provided to more fully illustrate the present invention, and shall not be construed as limiting the scope in any manner. Unless stated otherwise:

(i) all operations were carried out at room or ambient temperature (RT), that is, at a temperature in the range 18-25° C.;

(ii) evaporation of solvent was carried out using a rotary evaporator under reduced pressure (4.5-30 mmHg) with a bath temperature of up to 50° C.;

(iii) the course of reactions was followed by thin layer chromatography (TLC) and/or tandem high performance liquid chromatography (HPLC) followed by mass spectroscopy (MS), herein termed LCMS, and any reaction times are given for illustration only;

(iv) yields, if given, are for illustration only;

(v) the structure of all final compounds was assured by at least one of the following techniques: MS or proton nuclear magnetic resonance ($^1$H NMR) spectrometry, and the purity was assured by at least one of the following techniques: TLC or HPLC;

(vi) $^1$H NMR spectra were recorded on either a Varian Unity or a Varian Inova instrument at 500 or 600 MHz using the indicated solvent; when line-listed, NMR data is in the form of delta values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad; etc.;

(vii) MS data were recorded on a Waters Micromass unit, interfaced with a Hewlett-Packard (Agilent 1100) HPLC instrument, and operating on MassLynx/OpenLynx software; electrospray ionization was used with positive (ES+) or negative ion (ES−) detection; Waters XTerra MS C18-3.5 um-50× 3.0 mmID and diode array detection; the various methods used for analytical HPLC mass spectrometery conditions are listed below: Analytical HPLC mass spectrometry conditions:

Method A: Column: Waters Xterra MS C-18, 3.5μ, 3.0×50 mm
Temperature: 50° C.
Eluent: 10:90 to 98:2 v/v acetonitrile/water+0.05% TFA (or HCOOH) over 3.75 min.
Flow Rate: 1.0 mL/min, Injection 10
Detection: PDA, 200-600 nm
MS: mass range 150-750 amu; positive ion electrospray ionization Method B: Column: Waters Xterra IS C-18, 3.5μ, 2.1×20 mm
Temperature: 50° C.
Eluent: 10:90 to 98:2 v/v acetonitrile/water+0.05% TFA (or HCOOH) over 1.25 min.
Flow Rate: 1.5 mL/min, Injection 5
Detection: PDA, 200-600 nm
MS: mass range 150-750 amu; positive ion electrospray ionization Method C: Column: Waters Xterra IS C-18, 3.5μ, 2.1×20 mm
Temperature: 50° C.
Eluent: 10:90 to 98:2 v/v acetonitrile/water+0.05% TFA (or HCOOH) over 3.25 min.
Flow Rate: 1.5 mL/min, Injection 5 μL
Detection: PDA, 200-600 nm
MS: mass range 150-750 amu; positive ion electrospray ionization (viii) automated purification of compounds by preparative reverse phase HPLC was performed on a Gilson system using a YMC-Pack Pro C18 column (150×20 mm i.d.) eluting at 20 mL/min with 0-50% acetonitrile in water (0.1% TFA);

(ix) the purification of compounds by preparative thin layer chromatography (PTLC) was conducted on 20×20 cm glass prep plates coated with silica gel, commercially available from Analtech;

(x) flash column chromatography was carried out on a glass silica gel column using Kieselgel 60, 0.063-0200 mm ($SiO_2$), or a Biotage $SiO_2$ cartridge system including the Biotage Horizon and Biotage SP-1 systems;

(xi) chemical symbols have their usual meanings, and the following abbreviations have also been used: h (hours), min (minutes), v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent(s)), rt=retention time, $IC_{50}$ (molar concentration which results in 50% of maximum possible inhibition), $EC_{50}$ (molar concentration which results in 50% of maximum possible efficacy), uM (micromolar), nM (nanomolar);

(xii) definitions of some acronyms are as follows:

| | |
|---|---|
| AcOH is acetic acid | $BF_3 \cdot OEt_2$ is boron trifluoride diethyl etherate |
| celite is a diatomaceous earth | conc, conc. is concentrated |
| DBU is 1,8-Diazabicyclo[4.3.0]undec-7-ene | DCE is dichloroethane |
| DCM is dichloromethane (methylene chloride) | DIEA is N,N-diisopropyl ethyl amine |
| DMF is dimethyl formamide | DMSO is dimethyl sulfoxide |
| DPPF is 1,1'-bis(diphenylphosphino)ferrocene | EDC is 1-ethyl-3-(3-dimethylaminopropyl) carbodiimide |
| EDCI is 1-(3-Dimethylaminopropyl)-3-ethylcarbodiimide hydrochloride | EtOAc is ethyl acetate |
| EtOH is ethyl alcohol | FRET is Fluorescence Resonance Energy Transfer |
| iPA is isopropyl alcohol | iPrMgCl is isopropyl magnesium chloride |
| LiHMDS is lithium bis(trimethylsilyl) amide | LDA is lithium diisopropyl amide |
| mCPBA is 3-chloroperoxybenzoic acid | MeOH is methanol |
| NaHMDS is sodium bis(trimethylsilyl) amide | NBS is N-bromo-succinimide |
| NCS is N-chloro-succinimide | NIS is N-iodosuccinimide |
| NMP is N-Methyl-2-pyrrolidone | |

| | |
|---|---|
| PdCl$_2$(dppf)•CH$_2$Cl$_2$ is Dichloro 1,1'-bis(diphenylphosphino)ferrocene palladium (II) dichloromethane adduct | Pd$_2$(dba)$_3$ is Tris(dibenzylideneacetone) dipalladium (0); |
| Pd(PPh$_3$)$_4$ is tetrakis triphenylphosphine palladium (0) | TEA is Triethanolamine |
| TFA is trifluoroacetic acid | THF is tetrahydrofuran |
| TRF is Time-Resolved Fluorescence | |

Example 1

5-bromo-2-iodopyrimidin-4-amine

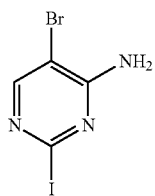

Step A

To a solution of 2,4-dichloro-4-bromo pyrimidine (5 g, 21.9 mmol) cooled to 0° C. was added hydriodic acid (50 mL, 379 mmol). The ice-bath was removed and the resulting mixture was stirred vigorously at room temperature for 18 hours. The reaction mixture was quenched by pouring into saturated bicarbonate solution. The resulting mixture was extracted with ethyl acetate (3×). The organic layer was washed with sodium thiosulfate solution, dried over anhydrous sodium sulfate filtered and concentrated to give a white solid.

Step B

To a solution of the intermediate from step A (1 g, 2.4 mmol) in THF (10 mL) in a pressure tube was bubbled ammonia gas for 20 minutes. The tube was capped and heated at 70° C. for one hour. The reaction mixture was cooled to room temperature and concentrated. The residue was suspended in ethyl acetate and washed with water. The organic layer was washed with brine, dried over anhydrous sodium sulfate filtered and concentrated to give a white solid. LC-MS: m/z=299.9; rt=0.96 min (Method B).

Example 2

2-[7-(2,3,6-trifluorobenzyl)imidazo[1,5-b]pyridazin-5-yl]-5-(1,3,5-trimethyl-1H-pyrazol-4-yl)pyrimidin-4-amine

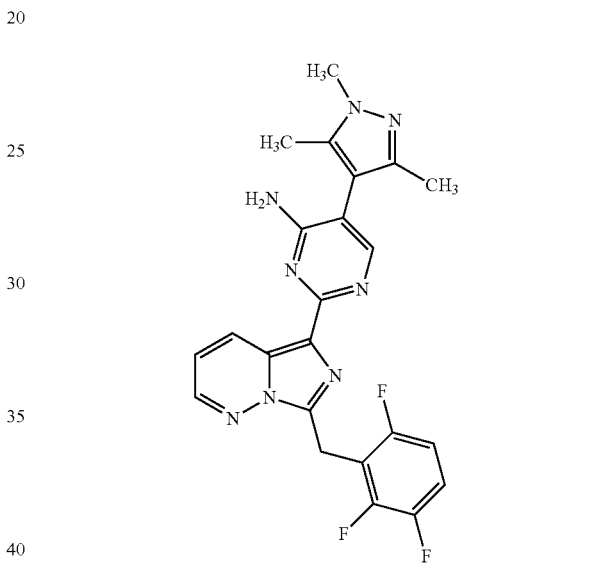

Step A

To a solution of pyridazine (3.63 ml, 49.9 mmol) in DCM (60 ml) was added trimethyl silyl cyanide (11.99 ml, 90 mmol) and aluminum chloride (20 mg, 0.150 mmol). After stirring the reaction mixture at room temperature for 10 minutes, a solution of para-toluene sulfonyl chloride (16.38 ml, 86 mmol) in DCM (100 mL) was added drop-wise via an addition funnel over 30 minutes. The resulting light orange solution was left stirring at room temperature for 18 hours. The reaction mixture was concentrated to give a light brown solid. To this material was added EtOH (100 mL) A white precipitate crashed out which was filtered through a sintered funnel, washed with ethanol (50 mL) and collected. LC-MS: m/z=262 (M+1); rt=1.4 min (Method C).

Step B

To a solution of the intermediate from Step A (10 g, 38.3 mmol) in anhydrous THF (90 ml) was added DBU (7.21 ml, 47.8 mmol) and the resulting solution was stirred at room temperature for 30 minutes. The reaction was quenched by the addition of saturated ammonium chloride solution (40 mL). The resulting mixture diluted with water (30 mL) and extracted with ethyl acetate several times (until aqueous layer had no product). The organic layer was washed with brine, dried over anhydrous sodium sulfate, filtered and concentrated. The residue was purified by flash chromatography on Biotage SPI system using 10-100% ethyl acetate-hexanes gradient to afford a white solid. LC-MS: m/z=106 (M+1); rt=0.45 min (Method A); $^1$H NMR (500 MHz, CDCl$_3$) δ 9.4 (m, 2H), 7.9 (m, 2H), 7.7 (m, 1H).

Step C

To a solution of the intermediate from step B (5.96 g, 56.7 mmol) in MeOH (35 ml) was added 6N HCl (20.89 ml, 125 mmol) followed by Pd/C (0.905 g, 8.51 mmol). The reaction mixture was kept on Parr shaker for 2 hours at 40 psi. The reaction mixture was filtered through celite and washed with 600 mL of MeOH and the filtrate concentrated. The residue was azeotroped several times with toluene A dark brown solid obtained. LC-MS: m/z=110 (M+1); rt=0.36 (Method A).

Step D

To a solution of 2,3,6-trifluorophenyl acetic acid (5.5 g, 29 mmol) and the intermediate from step C (5.0 g, 34 mmol) in DCM (20 ml) was added EDCI (7.9 g, 41.2 mmol) followed by DIEA (17.99 ml, 103 mmol). After stirring the reaction at room temperature for 18 hours, it was diluted with DCM (100 mL), and washed with water (2×). The organic layer was washed with brine, dried over anhydrous sodium sulfate, filtered and concentrated to give a brown solid. LC-MS: m/z=282 (M+1); rt=0.6 min (Method C).

Step E

To a solution of the intermediate from step D (2.6 g, 9.2 mmol) in 1,2-dichloroethane (25 mL) was added POCl$_3$ (5 ml, 53 mmol). The resulting mixture was refluxed for 3 hours. The reaction mixture was cooled to room temperature and concentrated. The residue was partitioned between water and ethyl acetate. The aqueous layer was neutralized with solid sodium bicarbonate and extracted with ethyl acetate (3×). The organic layer was washed with brine, dried over anhydrous sodium sulfate, filtered and concentrated. The residue was purified by flash chromatography on Biotage SP1 using a gradient of 10-100% ethyl acetate-hexanes to give a yellow solid. LC-MS: m/z=264 (M+1); rt=0.4 min (Method C). $^1$H NMR δ (ppm) (DMSO-d$_6$): 8.31 (1H, dd, J=4.26, 1.67 Hz), 8.09 (1H, dd, J=9.21, 1.64 Hz), 7.49-7.36 (2H, m), 7.17-7.10 (1H, m), 6.72 (1H, dd, J=9.23, 4.25 Hz), 4.45 (3H, s).

Step F

To a solution of the intermediate form step E (1.7 g, 6.46 mmol) in anhydrous acetonitrile (25 ml) was added a NiS (1.85 g, 8.22 mmol) and resulting mixture was heated to reflux for 20 minutes. The reaction mixture was cooled to room temperature and concentrated. The residue was suspended in ethyl acetate and washed with saturated sodium bicarbonate solution (2×) and saturated sodium thiosulfate (2×). The organic layer was washed with brine, dried over anhydrous sodium sulfate, filtered and concentrated. The residue was purified by flash chromatography on Biotage SP1 using a gradient of 5-50% ethyl acetate-hexanes to afford a bright yellow solid. LC-MS: m/z=390 (M+1); rt=1.87 min (Method C). $^1$H NMR (ppm) (DMSO-d$_6$): 8.39-8.33 (1H, m), 7.81 (1H, d, J=9.30 Hz), 7.49-7.40 (1H, m), 7.15 (1H, s), 6.83-6.77 (1H, m).

Step G

To a solution of the intermediate from Step F (525 mg, 1.349 mmol) in anhydrous THF (10 ml) at 0° C. was added isopropyl magnesium chloride (1.01 ml, 2.024 mmol, 2M in THF). After 10 minutes, trimethyl borate (759 µl, 6.75 mmol) was added and the reaction warmed to ambient temperature. After 5 minutes 2N HCl (2 eq, 2.6 mL) was added and the reaction stirred for 2 minutes. The reaction mixture was quenched by pouring it into saturated sodium bicarbonate solution. The resulting mixture was extracted with ethyl acetate (3×). The organic layer was washed with brine, dried over anhydrous sodium sulfate, filtered and concentrated.

Step H

To a solution of the intermediate from step G (414 mg, 1.35 mmol) in 1,4-dioxane (20 mL) was added the intermediate from Example 1 Step B (298 mg, 1 mmol) followed by K$_2$CO$_3$ 1M (10 ml). The resulting solution was degassed for 1 minute by bubbling nitrogen. The catalyst PdCl$_2$(dppf)-CH$_2$Cl$_2$ adduct (55.1 mg, 0.067 mmol) was added and the reaction was heated to 110° C. for 1 hour. The reaction mixture was cooled to room temperature and diluted with water (50 mL). A solid precipitated which was filtered and collected. The residue was rinsed with methanol (3×5 ml) and dried under vacuum to afford the desired product as a dark green solid. LC-MS: m/z=437.3 (M+2); rt=1.46 min (Method C).

Step I

To a solution of the intermediate from step H (250 mg, 0.574 mmol) and 1,3,5-trimethyl-4-(4,4,5,5-tetramethyl-1,3-dioxolan-2-yl)-1H-pyrazole (407 mg, 1.723 mmol) in 1,4-dioxane (6 ml), was added K$_2$CO$_3$ (2.87 ml, 2.87 mmol, 1M) and the resulting solution degassed for 2 minuted by bubbling nitrogen. The catalyst PdCl$_2$(dppf).CH$_2$Cl$_2$ (42.0 mg, 0.057 mmol) was added and the reaction heated in the microwave reactor at 140° C. for 15 min. The reaction mixture was cooled to room temperature and purified by reverse phase HPLC (Gilson) to afford the title compound. LC-MS: m/z=465.7 (M+1); rt=1.06 min (Method B); NMR δ (ppm) (DMSO-d$_6$): 8.98 (1H, dd), 8.45 (1H, dd), 7.90 (1H, s), 7.50 (1H, m), 7.19 (1H, t), 4.52 (2H, s), 3.68 (3H, s), 2.07 (3H, s), 1.99 (3H, s).

Example 3

5-[1,5-dimethyl-3-(trifluoromethyl)-1H-pyrazol-4-yl]-2-[7-(2,3,6-trifluorobenzyl)imidazo[1,5-b]pyridazin-5-yl]pyrimidin-4-amine

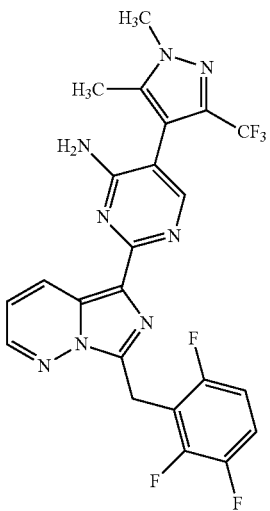 [SMILES: Cc1c(-c2cnc(-c3nc(Cc4c(F)ccc(F)c4F)n4ncccc34)nc2N)c(C(F)(F)F)nn1C]

Step A

To a solution of 5-methyl-3-(trifluoromethyl)-1H-pyrazole (3.5 g, 23 mmol) in anhydrous DMF (50 mL) was added sodium hydride (1.2 g, 30 mmol). After 5 minutes, iodomethane (1.97 mL, 31.5 mmol) was added. The reaction was stirred at room temperature for 1 hour, and quenched with water. The resulting mixture was extracted with ether. The organic layer was dried over anhydrous magnesium sulfate, filtered, and concentrated.

Step B

To a solution of the intermediate from step A (23 mmol) in acetic acid (23 mL) was added bromine (3.73 g, 23.32 mmol). After stirring at room temperature for 1 hour it was quenched by adding sodium sulfite and water. The resulting mixture was concentrated. The residue was diluted with ethyl acetate and washed with saturated sodium carbonate solution, brine, dried over anhydrous sodium sulfate, filtered and concentrated. The residue was purified by flash chromatography (Biotage) SP1 using a gradient of 0-30% ethyl acetate-hexanes.

Step C

To a solution of the intermediate from step B (1.65 g, 6.79 mmol) in anhydrous THF cooled to −78° C. was added tert-butyl lithium (7.99 mL, 13.58 mmol, 1.7M). After 5 minutes 2-methoxy-4,4,5,5-tetramethyl-1,3,2-dioxaborolane (3.89 mL, 23.76 mmol) was added. The reaction was warmed to room temperature and quenched with saturated ammonium chloride solution. The resulting mixture was extracted with ethyl acetate. The organic layer was washed with brine, dried over anhydrous sodium sulfate, filtered and concentrated. The residue was purified by flash chromatography (Biotage) using a gradient of 0-100% ethyl acetate-hexanes to give the desired product.

Step D

The title compound was prepared using the same procedure as described in Example 2 step I. LC-MS: m/z=519.5 (M+1); rt=1.03 min (Method B); $^1$H NMR (499 MHz, DMSO-$d_6$): δ 8.99 (d, J=9.3 Hz, 1H); 7.92 (s, 1H); 4.61 (s, 2H); 3.86 (s, 3H); 3.57 (s, 1H); 2.64 (s, 3H); 2.37 (s, 2H); 2.15 (s, 3H).

Example 4

5-(2-methylpyridin-4-yl)-2-[7-(2,3,6-trifluorobenzyl) imidazo[1,5-b]pyridazin-5-yl]pyrimidin-4-amine

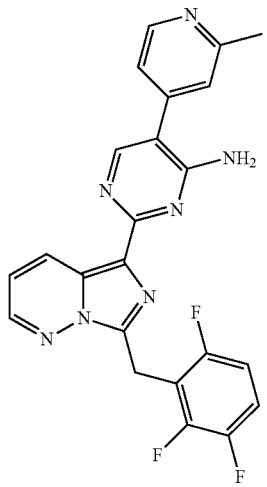 [SMILES: Cc1cc(-c2cnc(-c3nc(Cc4c(F)ccc(F)c4F)n4ncccc34)nc2N)ccn1]

Step A

A solution of 4-bromo-2-methylpyridine (2 g, 9.59 mmol) in 1,4-dioxane in a pressure tube was added potassium acetate (3.39 g, 34.5 mmol), bis(pinacolato)diboron and the resulting mixture de-gassed. Bis(tricyclohexylphosphino)palladium (0) (0.64 g, 0.959 mmol) was added and the reaction stirred at 120° C. for several hours. The reaction mixture was cooled to room temperature and quenched with 1N HCl until the pH was 6. The resulting mixture was concentrated. The residue was purified by reverse phase HPLC (Gilson) using a gradient of 10-10% acetonitrile/water with 0.1% TFA to afford the desired product as a white solid. LC-MS: m/z=138.17 (M+1); rt=0.56 min (Method C).

Step B

The title compound was prepared using the same procedure as described in Example 2 step I. LC-MS: m/z=462.98 (M+1); rt-0.97 min (Method B) NMR δ (ppm) (DMSO-$d_6$): 9.02 (1H, d, J=9.30 Hz), 8.50-8.45 (2H, m), 8.14 (1H, s), 7.48 (1H, dd, J=10.70, 5.59 Hz), 7.34 (1H, s), 7.27 (1H, d, J=5.18 Hz), 7.20-7.13 (1H, m), 7.01 (1H, dd, J=9.67, 4.45 Hz), 4.54 (2H, s), 2.51 (3H, s).

Example 5 methyl {4,6-diamino-2-[7-(2,3,6-trifluorobenzyl) imidazo[1,5-b]pyridazin-5-yl]pyrimidin-5-yl}carbamate

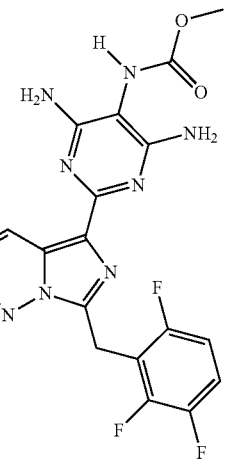

Step A

To a solution of the intermediate from Example 2 step F (1.5 g, 4.25 mmol) in DMF (5 ml) was added zinc cyanide (0.162 ml, 2.55 mmol) Pd$_2$dba$_3$ (0.078 g, 0.085 mmol), DPPF (0.141 g, 0.255 mmol) and water (0.5 mL). The resulting solution was heated at 110° C. for 1 hour. The reaction was cooled to room temperature, diluted with 50% NH$_4$OH solution (10 mL), and extracted with ethyl acetate. The organic layer was washed with brine, dried over anhydrous sodium sulfate, filtered and concentrated. The residue was purified on Biotage SP1 using a gradient of 10-100% ethyl acetate-hexanes to give a light yellow solid. LC-MS: m/z=289.03 (M+1); rt=1.08 min (Method B); $^1$H NMR δ (ppm) (DMSO-d$_6$): 8.64 (1H, dd, J=4.36, 1.56 Hz), 8.40 (1H, dd, J=9.30, 1.51 Hz), 7.52-7.43 (1H, m), 7.25-7.14 (2H, m), 4.52 (3H, s).

Step B

To a suspension of ammonium chloride (1.07 g, 20 mmol) in anhydrous toluene (30 mL) cooled to 0° C. was added trimethyl aluminum (10 mL, 20 mmol 2M/toluene). The ice-bath was removed and the reaction mixture stirred until a clear solution was obtained (1-2 hours). This solution was used in the next step.

Step C

To the intermediate from step A (2 g, 7.93 mmol) in toluene (1 ml) was added the freshly prepared aluminum reagent from step B (6 mL of 0.5 M solution in toluene). The resulting mixture was stirred at 110° C. for 3 hours. The reaction mixture was cooled to room temperature and quenched with silica-gel and 1:1 methanol-chloroform (50 mL) and the resulting slurry stirred vigorously for 30 minutes. The reaction mixture was filtered through silca gel pad (1") and washed with methanol. The filtrate was concentrated to yield a light yellow solid. LC-MS: m/z=306 (M+1), rt=0.22 min (Method B).

Step D

To 3-necked flask fitted with the mechanical stirrer was added aniline (140 g, 1.5 mol) and cooled to 0° C. in an ice-bath. Hydrochloric acid (250 mL, 12M) was added while maintaining the temperature below 15° C. A solution of sodium nitrite (105 g, 1.52 mol) in water (200 mL) was added slowly while maintaining the temperature below 12° C., A solution of sodium acetate (154 g, 1.87 mol) in water (700 mL) was added slowly at 12° C. This was followed by the slow addition of a solution of malononitrile (100 g, 1.521 mol) in ethanol (800 mL). After stirring the reaction mixture at room temperature for 1 hour, it was transferred to a filter funnel, washed with water and dried to give the desired product.

Step E

To a suspension of the intermediate from step C (520 mg, 1.703 mmol), and the intermediate from step D (435 mg, 2.56 mmol) in DMF (10 mL) was added sodium methoxide (138 mg, 2.56 mmol) and the resulting mixture stirred at 110° C. for 6 hours. The reaction was cooled to room temperature and a 1:1 mixture of acetonitrile-water was added. A brown solid precipitated out that was filtered and collected. LC-MS: m/z=476.6 (M+1); rt=1.15 min (Method B).

Step F

To a solution of the intermediate from step E (255 mg, 0.536 mmol) in 1:1 MeOH-DMF (10 mL) was added Pd/C (100 mg). The resulting mixture was stirred under a hydrogen balloon for 6 hours. The reaction mixture was filtered through celite. The filtrate was concentrated. LC-MS: m/z=387.4 (M+1), rt=1.03 min (Method B).

Step G

To a solution of the intermediate from step F (101 mg, 0.261 mmol) in anhydrous pyridine (3 mL) cooled to 0° C. was added methyl chloroformate (0.026 ml, 0.340 mmol). The ice-bath was removed and the reaction was stirred at room temperature for 10 minutes. The reaction mixture was concentrated and purified by reverse phase HPLC (Gilson) to give the desired compound. LC-MS: m/z=444.99 (M+1), rt=0.99 min (Method B); $^1$H NMR δ (ppm) (DMSO-d$_6$): 9.01 (1H, d), 8.40 (1H, s), 7.92 (1H, s), 7.43 (1H, m), 7.18 (1H, t), 6.90 (1H, s), 5.95-6.10 (4H, s), 4.50 (2H, s), 3.60 (3H, s)

Example 6 methyl {4,6-diamino-2-[7-(2,3,6-trifluorobenzyl)imidazo[1,5-b]pyridazin-5-yl]pyrimidin-5-yl}methylcarbamate

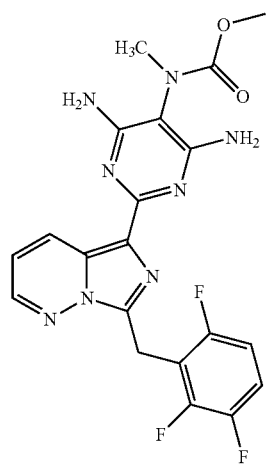 [SMILES: COC(=O)N(C)c1c(N)nc(-c2nc(Cc3c(F)ccc(F)c3F)n3ncccc23)nc1N]

To a solution of the intermediate from Example 5 step G in anhydrous DMF (1 mL) cooled to 0° C. was added drop-wise lithium bis(trimethylsilyl)amide (0.059 mL, 0.059 mmol). After 5 minutes, a solution of methyl iodide (3.38 μl, 0.054 mmol) in DMF (170 μl) was added. The reaction mixture was stirred at room temperature for 5 minutes and quenched by adding water. The resulting mixture was extracted with ethyl acetate (3×). The organic layer was dried over anhydrous sodium sulfate, filtered, concentrated and the residue was purified by reverse phase HPLC (Gilson) to give the title compound. LC-MS: m/z=459.49 (M+1); $^1$H NMR δ (ppm) (DMSO-d$_6$): 9.01 (1H, d), 8.40 (1H, s), 7.45 (1H, m), 7.18 (1H, t), 6.91 (1H, s), 6.05-6.15 (4H, s), 4.50 (2H, s), 3.62 (1H, s), 3.50 (2H, s), 2.97 (3H, s).

The following examples were synthesized using the procedures described in Examples 1-6.

TABLE 1

| Ex. | Z | $R^a$ | $R^b$ | $R^c$ | $R^d$ | $R^e$ | Retention time (min) | m/z (M + 1) | LC Method |
|---|---|---|---|---|---|---|---|---|---|
| 7 | quinolin-5-yl | F | H | H | F | F | 1.01 | 484.54 | B |
| 8 | pyridin-4-yl | F | H | H | F | F | 1.03 | 434.52 | B |
| 9 | pyridin-3-yl | F | H | H | F | F | 1.0 | 434.6 | B |
| 10 | 5-(trifluoromethyl)pyridin-3-yl | F | H | H | F | F | 1.09 | 502.54 | B |
| 11 | 5-fluoropyridin-3-yl | F | H | H | F | F | 1.05 | 452.6 | B |
| 12 | 2-methoxypyridin-3-yl | F | H | H | F | F | 1.06 | 464.6 | B |

TABLE 1-continued
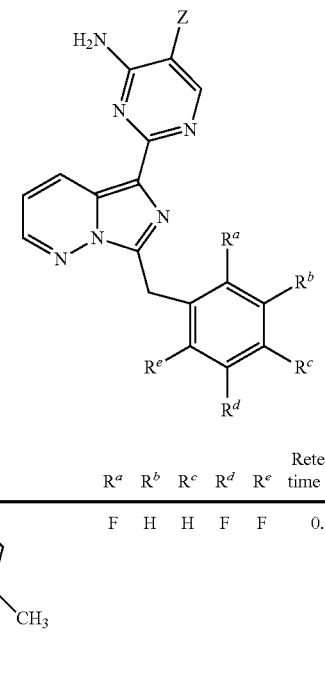
| Ex. | Z | $R^a$ | $R^b$ | $R^c$ | $R^d$ | $R^e$ | Retention time (min) | m/z (M + 1) | LC Method |
|---|---|---|---|---|---|---|---|---|---|
| 13 | 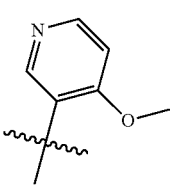 [SMILES: *c1cnccc1OC] | F | H | H | F | F | 0.99 | 448.47 | B |
| 14 | 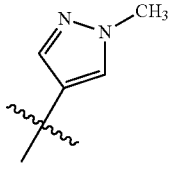 [SMILES: *c1cnn(C)c1] | F | H | H | F | F | 0.95 | 464.56 | B |
| 15 | 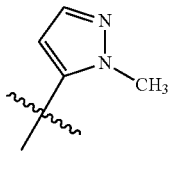 [SMILES: *c1ccnn1C] | F | H | H | F | F | 1.0 | 436.99 | B |
| 16 | 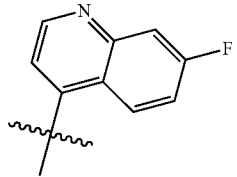 [SMILES: *c1ccnc2cc(F)ccc12] | F | H | H | F | F | 1.08 | 437.44 | B |
| 17 | 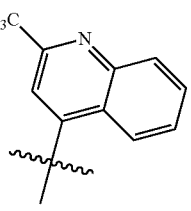 | F | H | H | F | F | 1.03 | 502 | B |
| 18 |  | F | H | H | F | F | 1.07 | 552 | B |

TABLE 1-continued
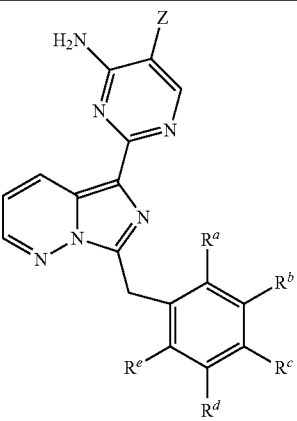
| Ex. | Z | R$^a$ | R$^b$ | R$^c$ | R$^d$ | R$^e$ | Retention time (min) | m/z (M + 1) | LC Method |
|---|---|---|---|---|---|---|---|---|---|
| 19 | 3-fluoropyridin-4-yl | F | H | H | F | F | 1.01 | 452 | B |
| 20 | 2-(trifluoromethyl)pyridin-4-yl | F | H | H | F | F | 1.04 | 502 | B |
| 21 | 2-(trifluoromethyl)quinolin-4-yl | F | H | H | F | F | 1.07 | 552 | B |
| 22 | 1-methyl-3-(trifluoromethyl)-1H-pyrazol-4-yl | F | H | H | F | F | 1.02 | 505 | B |
| 23 | pyridin-4-yl | H | F | H | F | F | 2.3 | 434.19 | A |
| 24 | pyridin-3-yl | H | F | H | F | F | 2.39 | 434.19 | A |

TABLE 1-continued

| Ex. | Z | R$^a$ | R$^b$ | R$^c$ | R$^d$ | R$^e$ | Retention time (min) | m/z (M + 1) | LC Method |
|---|---|---|---|---|---|---|---|---|---|
| 25 | 4-methoxypyridin-3-yl | H | F | H | F | F | 2.33 | 464.23 | A |
| 26 | 4-methylpyridin-3-yl | H | F | H | F | F | 2.33 | 448.13 | A |
| 27 | quinolin-4-yl | H | F | H | F | F | 2.48 | 484.12 | A |
| 28 | 2-methylpyridin-4-yl | H | F | H | F | F | 2.31 | 448.14 | A |
| 29 | pyridin-4-yl | F | H | H | F | Cl | 0.97 | 450 | B |
| 30 | 1,3,5-trimethyl-1H-pyrazol-4-yl | F | H | H | F | Cl | 1.0 | 481 | B |

TABLE 1-continued
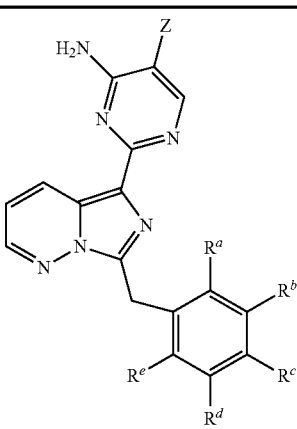
| Ex. | Z | R$^a$ | R$^b$ | R$^c$ | R$^d$ | R$^e$ | Retention time (min) | m/z (M + 1) | LC Method |
|---|---|---|---|---|---|---|---|---|---|
| 31 | 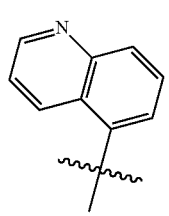 [SMILES: *c1cccc2ncccc12] | F | H | H | F | Cl | 0.95 | 464 | B |
| 32 | 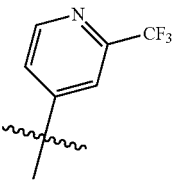 [SMILES: *c1ccnc(C(F)(F)F)c1] | F | H | H | F | Cl | 0.99 | 500 | B |
| 33 | 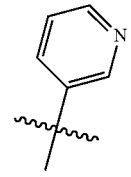 | F | H | H | F | Cl | 1.05 | 518 | B |
| 34 | 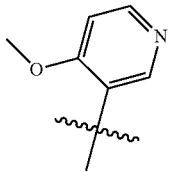 | F | H | H | F | Cl | 0.97 | 450 | B |
| 35 | 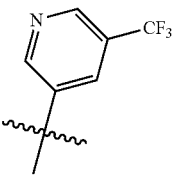 [SMILES: *c1cncc(C(F)(F)F)c1] | F | H | H | F | Cl | 0.92 | 480 | B |
| 36 | | F | H | H | F | Cl | 1.04 | 518 | B |

TABLE 1-continued
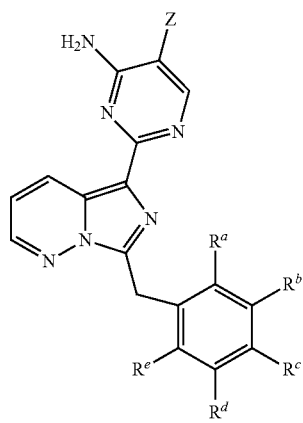
| Ex. | Z | $R^a$ | $R^b$ | $R^c$ | $R^d$ | $R^e$ | Retention time (min) | m/z (M + 1) | LC Method |
|---|---|---|---|---|---|---|---|---|---|
| 37 | 4-methyl-pyridin-3-yl | F | H | H | F | Cl | 0.96 | 464 | B |
| 38 | 1-methyl-pyrazol-4-yl | F | H | H | F | Cl | 0.99 | 453 | B |
| 39 | 1,5-dimethyl-3-CF$_3$-pyrazol-4-yl | F | H | H | F | Cl | 1.04 | 535 | B |
| 40 | 1,5-dimethyl-3-methyl-pyrazol-4-yl | H | F | H | F | F | 2.71 | 465.24 | A |
| 41 | 1,5-dimethyl-3-CF$_3$-pyrazol-4-yl | H | F | H | F | F | 2.88 | 519.23 | A |

TABLE 1-continued
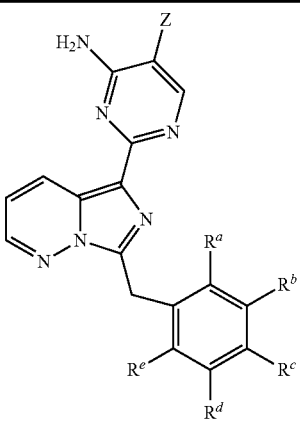
| Ex. | Z | $R^a$ | $R^b$ | $R^c$ | $R^d$ | $R^e$ | Retention time (min) | m/z (M + 1) | LC Method |
|---|---|---|---|---|---|---|---|---|---|
| 42 | H₃C-N-N, H₃C, CH₃ (trimethylpyrazole) | F | H | H | Cl | F | 1.09 | 481 | B |
| 43 | 2-CF₃-pyridin-4-yl | H | F | H | F | F | 2.84 | 502.54 | A |
| 44 | 3-CF₃-pyridin-5-yl | H | F | H | F | F | 2.84 | 502.54 | A |
| 45 | 3-SO₂Me-phenyl | H | F | H | F | F | 2.73 | 511.2 | A |
| 46 | 3-SO₂Me-phenyl | H | F | H | F | Cl | 1.08 | 527 | B |
| 47 | 2-SO₂Me-phenyl | H | F | H | F | F | 2.72 | 511.32 | A |

TABLE 1-continued
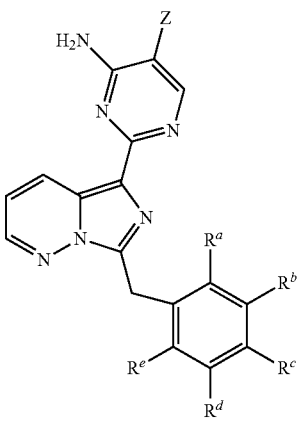
| Ex. | Z | $R^a$ | $R^b$ | $R^c$ | $R^d$ | $R^e$ | Retention time (min) | m/z (M + 1) | LC Method |
|---|---|---|---|---|---|---|---|---|---|
| 48 | 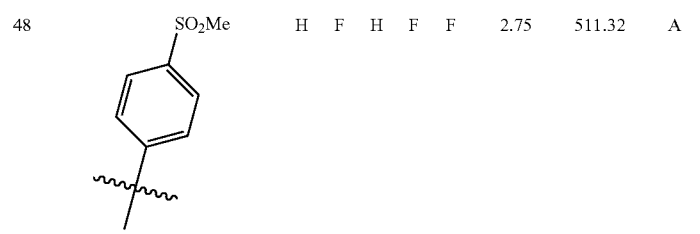 | H | F | H | F | F | 2.75 | 511.32 | A |
| 49 |  | H | F | H | F | F | 2.94 | 463.10 | A |
| 50 | 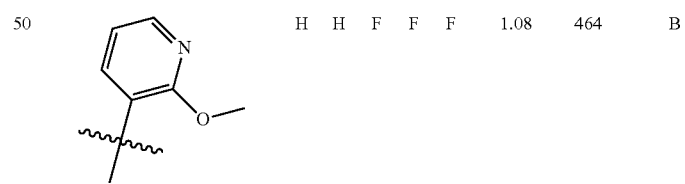 | H | H | F | F | F | 1.08 | 464 | B |
| 51 |  | H | H | F | F | F | 1.01 | 464 | B |

TABLE 1-continued
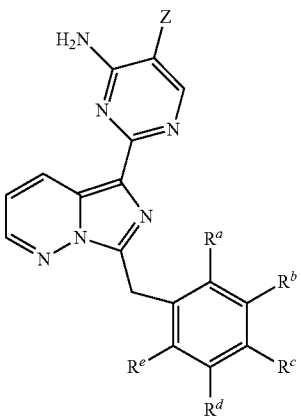
| Ex. | Z | $R^a$ | $R^b$ | $R^c$ | $R^d$ | $R^e$ | Retention time (min) | m/z (M + 1) | LC Method |
|---|---|---|---|---|---|---|---|---|---|
| 52 | 5-(trifluoromethyl)pyridin-3-yl | H | H | F | F | F | 1.09 | 502 | B |
| 53 | pyridin-4-yl | H | H | F | F | F | 0.99 | 434 | B |
| 54 | 1-methyl-1H-pyrazol-5-yl | F | H | H | F | F | 1.08 | 437.4 | B |
| 55 | 3-(methylsulfonyl)phenyl | H | H | F | F | F | 1.07 | 511 | B |

Example 56

2-[6-fluoro-3-(2,3,6-trifluorobenzyl)imidazo[1,5-a]pyridin-1-yl]-5-pyridin-3-ylpyrimidin-4-amine

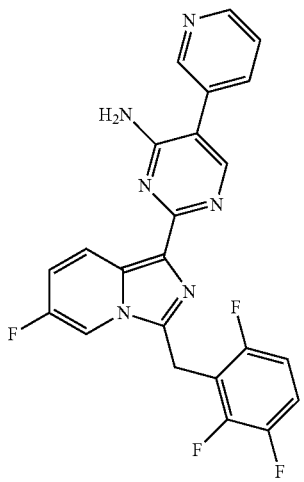 [SMILES: Nc1nc(-c2nc(Cc3c(F)ccc(F)c3F)n3cc(F)ccc23)ncc1-c1cccnc1]

Step A

To a suspension of 5-amino-2-cyano pyridine (20.06 g, 168 mml) in a 2 L Erlenmeyer flask in HF-pyridine (100 g, 3.5 mol) cooled to 0° C. was added sodium nitrite (17.4 g, 251 mmol) in 4 portions. After 45 minutes at 0° C. the reaction was stirred at ambient temperature for 30 minutes, and then heated at 80° C. for 1.5 hours. The reaction mixture was cooled to room temperature and quenched by pouring into ice/water mixture (~400 mL). The resulting solution was extracted with DCM (6×150 mL). The organic layer was dried over anhydrous sodium sulfate, filtered and concentrated to yield an orange solid. LC-MS: m/z=123.09 (M+H); rt=2.32 min (Method A).

Step B

The nitrile was reduced to the amine by following the same procedure as described in Example 2 step C. LC-MS: m/z=127.1 (M+H); rt=0.13 min (Method C).

Step C

To a suspension of 2-(ammoniomethyl)-5-fluoropyridinium dichloride from step B (2 g, 10.05 mmol) and 2-fluoro phenyl acetic acid (1.86 g, 12.06 mmol) in anhydrous dichloromethane (20 mL) was added EDCI (2.3 g, 12.06 mmol) followed by DIEA (7 ml, 40 mmol). The resulting reaction mixture was stirred at room temperature for 18 hours. The reaction mixture was diluted with DCM (50 mL) and washed with water (2×), dried over anhydrous sodium sulfate, filtered and concentrated. The crude product was carried on to next step with out any further purification. LC-MS: m/z=299 (M+1), rt-0.99 min (Method B).

Step D

To a solution of the intermediate from step C (3.0 g, 10.05 mmol) in DCE (20 mL) was added phosphorous oxy chloride (7.49 mL, 80 mmol). The resulting mixture was heated at 85° C. for 3 hours. The reaction mixture was cooled to room temperature and poured into ice-water (100 mL) and neutralized by the addition of solid $Na_2CO_3$ until the pH >8. The resulting mixture was extracted with ethyl acetate (3×50 mL). The organic layer was dried over anhydrous sodium sulfate, filtered and concentrated and the residue was purified on Biotage SP1 system with a gradient of 10-10% ethyl acetate-hexanes to obtain the desired product. LC-MS: m/z=281.37 (M+1); rt=0.16 min (Method B).

Step E

To a solution of the intermediate from step D (1.52 g, 5.4 mmol) in DCM (20 mL) was added NIS (1.34 g, 5.96 mmol) and the resulting mixture stirred at room temperature for 3 hours. The reaction mixture was diluted with DCM, washed with saturated sodium thiosulfate solution (2×50 mL), water (1×), dried over anhydrous sodium sulfate, filtered and concentrated. The residue was purified on Biotage SP1 system with a gradient of 0-50% ethyl acetate-hexanes to afford the desired product as a green solid. LC-MS: m/z=406.94 (M+1); rt-1.17 min (Method B).

Step F

To a solution of the intermediate from Step E (701 mg, 1.72 mmol) in anhydrous THF (5 ml) at 0° C. was added isopropyl magnesium chloride (1.39 ml, 2.79 mmol). After 10 minutes, trimethyl borate (623 µl, 5.57 mmol) was added and the reaction warmed to ambient temperature. After stirring the reaction mixture for 5 minutes 2N HCl (1 mL) was added and the reaction stirred for 2 minutes. The reaction mixture was quenched by being poured into saturated sodium bicarbonate solution. The resulting mixture was extracted with ethyl acetate (3×). The organic layer was washed with brine, dried over anhydrous sodium sulfate, filtered and concentrated. This material was used in the next step without any further purification.

Step G

To a solution of the intermediate from step F in 1,4-dioxane (20 mL) was added the intermediate from Example 1 Step B (398 mg, 1.3 mmol) followed by 1M $K_2CO_3$ (5 ml). The resulting solution was degassed for 1 minute by bubbling nitrogen. The catalyst $PdCl_2$(dppf)-$CH_2Cl_2$ adduct (54 mg, 0.066 mmol) was added the reaction was heated 110° C. for 1 hour. The reaction mixture was cooled to room temperature and diluted with water (50 mL). A solid precipitated which was filtered. The residue was rinsed with methanol (3×5 ml) and dried under vacuum to afford the desired product as a brown solid. LC-MS: m/z=451.8 (M+1); rt=0.99 min (Method B).

Step H

To a solution of the intermediate from step G (10 mg, 0.022 mmol) and 3-pyridyl boronic acid (8.2 mg, 0.066 mmol) in 1,4-dioxane (0.5 ml), was added $K_2CO_3$ (0.11 ml, 0.11 mmol, 1M) and the resulting solution degassed for 2 minutes by bubbling nitrogen. The catalyst $PdCl_2$(dppf).$CH_2Cl_2$ (2 mg, 2.2 µmol) was added and the reaction heated in the microwave at 140° C. for 10 min. The reaction mixture was cooled to room temperature and purified by reverse phase HPLC (Gilson) to afford the title compound. LC-MS: m/z=451.8 (M+1), rt=0.99 min; $^1$H NMR δ (ppm) (DMSO-$d_6$): 8.75 (2H, m), 8.60 (1H, s), 8.48 (1H, d), 8.05 (1H, s), 7.92 (1H, m), 7.45 (2H, m), 7.09 (2H, m), 6.90 (2H, s), 4.50 (2H, s)

The following examples were synthesized using the procedures described in Examples 1-6 and Example 56.

TABLE 2

| Ex. | Substituent Z | Retention time (min) | m/z (M + 1) | LC Method |
|---|---|---|---|---|
| 57 | 5-quinolinyl | 0.99 | 501.6 | B |
| 58 | 4-pyridyl | 0.99 | 451.5 | B |
| 59 | 1,3,5-trimethyl-1H-pyrazol-4-yl | 1.07 | 482.6 | B |
| 60 | 5-(trifluoromethyl)pyridin-3-yl | 1.1 | 519.6 | B |
| 61 | 5-fluoropyridin-3-yl | 1.06 | 469.6 | B |
| 62 | 2-methoxypyridin-3-yl | 1.09 | 481.6 | B |

TABLE 2-continued

| # | Structure | | | |
|---|---|---|---|---|
| 63 | pyridine with CH₃ | 0.99 | 465.6 | B |
| 64 | pyridine with CH₃ | 0.99 | 465.6 | B |
| 65 | pyridine with OCH₃ | 0.99 | 481.5 | B |
| 66 | pyrimidine | 1.03 | 452.6 | B |
| 67 | pyrazole-N-CH₃ | 1.01 | 454.02 | B |
| 68 | pyrazole-N-CH₃ | 1.06 | 454.5 | B |
| 69 | pyrazole with F₃C, CH₃, CH₃ | 1.2 | 521 | B |
| 70 | pyridine with F₃C | 1.03 | 519 | B |

TABLE 2-continued

| 71 | [3-fluoropyridin-4-yl] | 1.0 | 468 | B |
| 72 | [2-(trifluoromethyl)quinolin-4-yl] | 1.28 | 569 | B |
| 73 | [6-fluoroquinolin-4-yl] | 1.03 | 519 | B |
| 74 | [quinolin-4-yl] | 1.15 | 486 | B |
| 75 | [1-methyl-3-(trifluoromethyl)-1H-pyrazol-4-yl] | 1.03 | 522 | B |
| 77 | [1-methyl-1H-pyrrolo[2,3-b]pyridin-4-yl] | 0.9 | 504 | B |
| 78 | [3-methylpyridin-4-yl] | 0.95 | 465 | B |
| 79 | [2-methoxypyridin-4-yl] | 1.01 | 481 | B |

TABLE 2-continued

| Ex. | Structure | Retention time (min) | m/z (M + 1) | LC Method |
|---|---|---|---|---|
| 80 | 3,5-dimethylisoxazol-4-yl | 1.07 | 469 | B |
| 81 | 1-methyl-1H-imidazol-5-yl | 0.98 | 454 | B |
| 82 | 3-(methylsulfonyl)phenyl | 1.07 | 527 | B |
| 76 | (see structure) | 1.00 | 512 | B |

Example 83

2-[5-chloro-3-(2,3,6-trifluorobenzyl)-1H-indazol-1-yl]-5-(1-methyl-1H-pyrazol-4-yl)pyrimidine-4,6-diamine

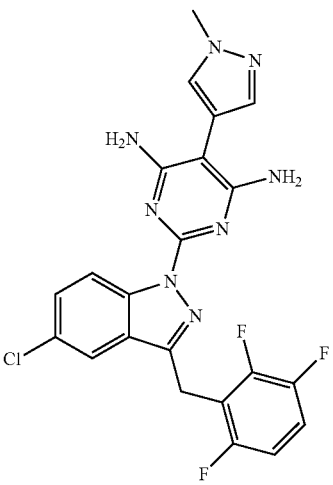 [SMILES: Cn1cc(-c2c(N)nc(-n3nc(Cc4c(F)ccc(F)c4F)c4cc(Cl)ccc43)nc2N)cn1]

Step A

To a solution of 2,3,-6 trifluoro phenyl acetic acid (5 g, 26.3 mmol) and methyl 5-bromo-3-chloro benzoate in anhydrous THF (53 mL) cooled to −78° C. was added slowly NaHMDS (110 mL, 65.7 mmol, 0.6 M). The reaction was warmed to 0° C. After stirring for 30 minutes it was quenched by the addition of 1N HCl (100 mL). The resulting mixture was stirred vigorously at room temperature for 1 hour and concentrated. The residue was extracted with EtOAc. The organic layer was washed with saturated sodium bicarbonate solution (2×), water and brine, then dried over sodium sulfate, filtered and concentrated. The crude material was carried on to the next step. $^1$H NMR δ (ppm)(CH$_3$CN-d$_6$): 7.66-7.61 (2H, m), 7.40 (1H, dd, J=8.58, 2.56 Hz), 7.25 (1H, qd, J=9.52, 5.12 Hz), 6.98 (1H, tdd, J=9.04, 3.76, 2.25 Hz), 4.34 (2H, s).

Step B 4,6-dichloro-2-(methylthio) pyrimidine (25 g, 128 mmol) was dissolved in benzylamine (70 mL, 641 mmol) in an ice bath. After stirring for 20 minutes, the solution was diluted with ethyl acetate, washed with water (3×), brine and dried over anhydrous sodium sulfate. The organic layer was filtered and concentrated to give the desired compound as a pale yellow oil. LC-MS: m/z=265.97 (M+1); rt=1.18 min (Method B).

Step C

The a solution of the intermediate from step B (30 g, 113 mmol) in DCM (150 mL) cooled to −78° C. was added mCPBA (29.2 g, 169 mmol). After stirring at the reaction for 10 minutes the mixture was warmed to room temperature and additional mCPBA (29.2 g, 169 mmol) was added. The reaction was stirred for 90 minutes and then the DCM was removed under reduced pressure. The residue was dissolved in EtOAc and washed several times with saturated sodium bicarbonate, water, and brine. The organic layer was dried over anhydrous sodium sulfate, filtered and concentrated. The crude material was carried on to the next step. LC-MS: m/z=298.18 (M+1); rt=1.58 min, Step D To a solution of the intermediate from step C (33.6 g, 113 mmol) in 1,4-dioxane (113 mL) was added anhydrous hydrazine (17.7 mL, 564 mmol). The solution was stirred at ambient temperature for 1 hour. The dioxane was removed and the resulting orange solid was triturated with MeOH. The filtrate was then concentrated and triturated several more times to yield the desired compound as a white solid. LC-MS: m/z=250.17 (M+1); rt=0.91 min.

Step E

To a solution of the intermediate from step A (9.4 g, 25.9 mmol) and the intermediate from step D (6.78 g, 27.1 mmol) in methanol in a sealed tube was added BF$_3$.OEt$_2$ (9.83 mL, 78 mmol). The resulting mixture was heated at 100° C. for 90 minutes. The reaction mixture was cooled to room temperature and concentrated. The residue was dissolved in ethyl acetate washed with 1M K$_2$CO$_3$ solution (3×), brine, dried over anhydrous sodium sulfate, filtered and concentrated. The crude material was carried on to the next step without any further purification. LC-MS: m/z=595.96 (M+1); rt=1.3 min (Method B).

Step F

To a solution of the intermediate from step E (15.2 g, 25.5 mmol) in DMF (100 mL) was added copper (I) iodide (4.86 g, 25.5 mmol) and ethylenediamine (1.39 mL, 12.77 mmol). After stirring at room temperature for 30 minutes, the reaction mixture was diluted with ethyl acetate and washed several times with 5% ammonium hydroxide solution. The organic layer was washed with brine, dried over anhydrous sodium sulfate, filtered and concentrated. The residue was purified by flash chromatography (Biotage) SP1 system using a gradient of 5-20% ethyl acetate-hexanes to give the desired product. LC-MS: m/z=514.15 (M+1); rt=2.7 min (Method B).

Step G

A solution of the intermediate from step F (9.1 g, 17.7 mmol) in neat benzyl amine (77 ml, 708 mmol) was heated at 140° C. for 45 minutes. The reaction mixture was cooled to room temperature, diluted with ethyl acetate and washed with water (4×). The organic layer was dried over anhydrous sodium sulfate, filtered and concentrated. The crude material was carried on to next step without any further purification. LC-MS: m/z=585.21 (M+1); rt=2.55 min (Method C).

Step H

To a solution of the intermediate from step G (10.3 g, 17.6 mmol) in acetic acid (10 mL) was added bromine (0.9 ml, 17.61 mmol) in AcOH (1 mL) and the resulting mixture stirred at room temperature. Upon completion, it was quenched with water and sodium sulfite solution. After concentration the residue was suspended in ethyl acetate and neutralized with potassium carbonate solution. The organic layer was washed with brine, dried over anhydrous sodium sulfate, filtered and concentrated. The residue was purified by flash chromatography Biotage to give the desired product. LC-MS: m/z=665.06 (M+1); rt=1.36 min (Method B).

Step I

To a solution of the intermediate from step H (500 mg, 0.753 mmol) in 1,4-dioxane (20 mL) was added 1-methyl-4-(4,4,5,5-tetramethyl-1,3-dioxolan-2-yl)-1H-pyrazole (235 mg. 1.13 mmol), 1,1 Bis(Di-tert-butylphosphino)palladium dichloride (25 mg, 0.038 mmol) and potassium carbonate solution (7.53 mL, 1M). The resulting mixture was degassed and heated in the microwave reactor at 90° C. for 5 minutes. The reaction mixture was filtered and purified by reverse phase HPLC (Gilson) using a gradient of 65-100% water: acetonitrile to give the desired compound. LC-MS: m/z=665.23 (M+1); rt-1.36 min (Method B).

Step J

To a solution of the intermediate from step 1 (340 mg, 0.51 mmol) in DCM (3 mL) was added triflic acid (0.68 mL, 7.67 mmol). Upon completion of the reaction it was quenched by the addition of aqueous potassium carbonate solution. The aqueous layer was extracted with 30% iPA/CHCl$_3$. The organic layer was concentrated. The residue was purified by reverse phase HPLC (Gilson) to give the title compound. LC-MS: m/z=485.23 (M+1); rt=1.13 min (Method B); $^1$H NMR δ (ppm)(DMSO-d$_6$): 8.90 (1H, d, J=9.05 Hz), 7.85 (1H, s), 7.74 (1H, s), 7.53-7.42 (3H, m), 7.20 (1H, J=9.15 Hz), 6.07 (4H, s), 4.44 (2H, s), 3.87 (3H, s).

The following examples were synthesized using the procedures described in Example 83.

TABLE 3

| Example | Substituent Z | Retention time (min) | m/z (M + 1) | LC Method |
|---------|---------------|----------------------|-------------|-----------|
| 84 | 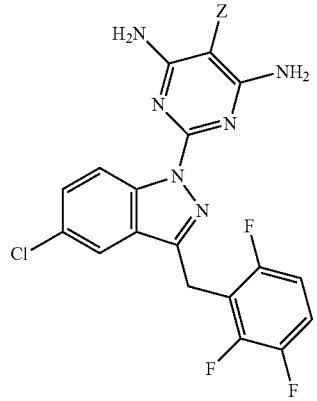 | 1.11 | 497 | B |
| 85 | 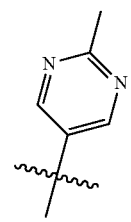 | 1.10 | 482 | B |
| 86 | 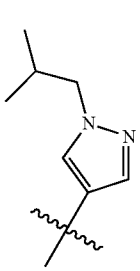 [SMILES: *c1cnn(CC(C)C)c1] | 1.17 | 527.8 | B |
| 87 | 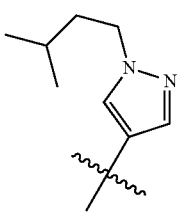 [SMILES: *c1cnn(CCC(C)C)c1] | 1.19 | 570 | B |

TABLE 3-continued

| Example | Substituent Z | Retention time (min) | m/z (M + 1) | LC Method |
|---|---|---|---|---|
| 88 | (1,1-dimethylethyl-3-methylpyrazol-4-yl-methyl) | 1.17 | 541.8 | B |
| 89 | (1-cyclopropylmethyl-3-methylpyrazol-4-yl-methyl) | 1.11 | 553.8 | B |
| 90 | (5-methoxymethyl-1,3-dimethylpyrazol-4-yl-methyl) | 1.14 | 543.73 | B |
| 91 | (1,3,5-trimethylpyrazol-4-yl-methyl) | 1.13 | 513.96 | B |
| 92 | (pyridin-3-yl-methyl) | 1.09 | 482.7 | B |

TABLE 3-continued
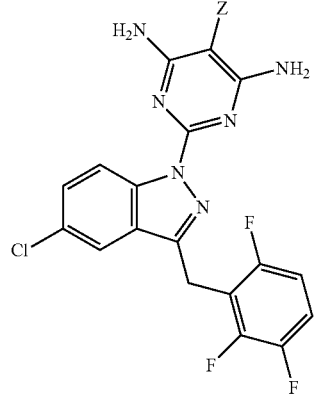
| Example | Substituent Z | Retention time (min) | m/z (M + 1) | LC Method |
|---|---|---|---|---|
| 93 | 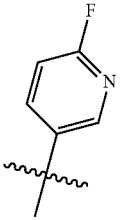 | 1.14 | 500.91 | B |
| 94 | 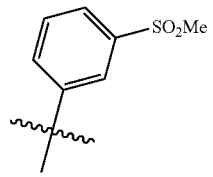 [SMILES: *c1cccc(S(C)(=O)=O)c1] | 1.15 | 559.72 | B |
| 95 | 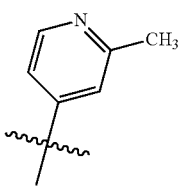 [SMILES: *c1ccnc(C)c1] | 1.08 | 496 | B |
| 96 | 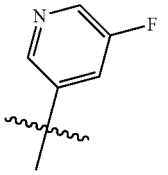 [SMILES: *c1cncc(F)c1] | 1.19 | 500.1 | B |
| 97 | 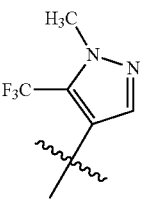 | 1.15 | 553.06 | B |

TABLE 3-continued
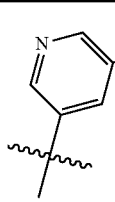
| Example | Substituent Z | Retention time (min) | m/z (M + 1) | LC Method |
|---|---|---|---|---|
| 98 | 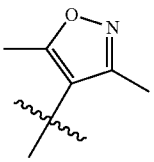 | 1.16 | 512.09 | B |
| 99 | 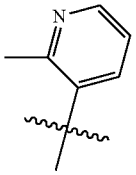 [SMILES: *c1cccnc1C] | 1.18 | 500.1 | B |
| 100 | 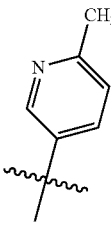 | 1.1 | 496.1 | B |
| 101 | 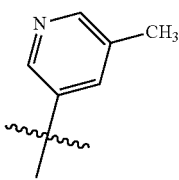 [SMILES: *c1cncc(C)c1] | 1.11 | 495.9 | B |
| 102 | 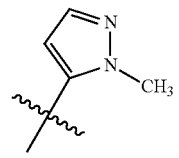 [SMILES: *c1ccnn1C] | 1.14 | 496.13 | B |
| 103 |  | 1.18 | 485.1 | B |

TABLE 3-continued
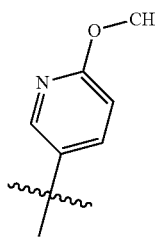
| Example | Substituent Z | Retention time (min) | m/z (M + 1) | LC Method |
|---|---|---|---|---|
| 104 | 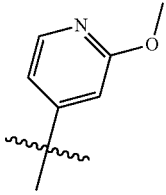 [SMILES: *c1ccnc(OC)c1] | 1.13 | 511.97 | B |
| 105 | 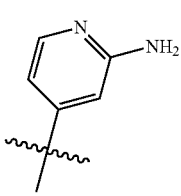 [SMILES: *c1ccnc(N)c1] | 1.14 | 511.98 | B |
| 106 | 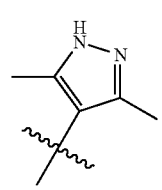 | 1.1 | 496.92 | B |
| 107 | 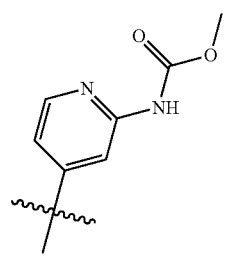 [SMILES: *c1ccnc(NC(=O)OC)c1] | 1.13 | 499.05 | B |
| 108 |  | 1.18 | 559.2 | B |

TABLE 3-continued
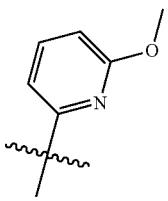 [SMILES: *c1cccc(OC)n1]
| Example | Substituent Z | Retention time (min) | m/z (M + 1) | LC Method |
|---|---|---|---|---|
| 109 | 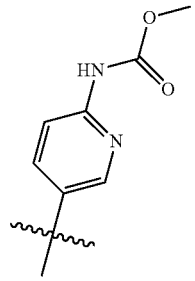 [SMILES: *c1ccc(NC(=O)OC)nc1] | 1.21 | 512.09 | B |
| 110 | 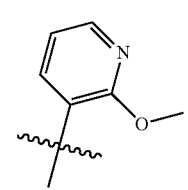 [SMILES: *c1cccnc1OC] | 1.12 | 555.01 | B |
| 111 | 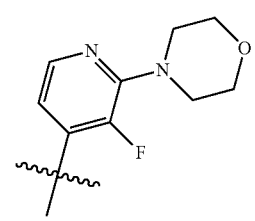 [SMILES: *c1ccnc(N2CCOCC2)c1F] | 1.13 | 511.97 | B |
| 112 | 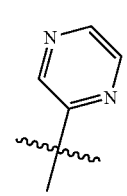 | 1.15 | 585.01 | B |
| 113 | | 1.18 | 483 | B |

TABLE 3-continued

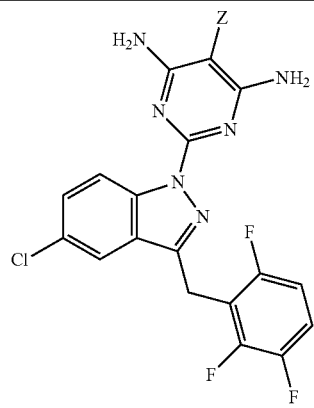

| Example | Substituent Z | Retention time (min) | m/z (M + 1) | LC Method |
|---|---|---|---|---|
| 114 | ![structure] | 1.11 | 538.98 | B |

Example 115

2-[5-fluoro-3-(2,3,6-trifluorobenzyl)-1H-indazol-1-yl]-5-(2-methoxypyridin-4-yl)pyrimidine-4,6-diamine

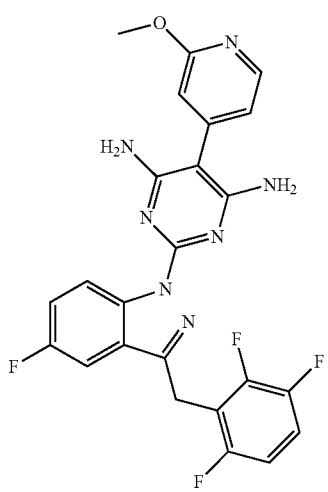 [SMILES: COc1cc(-c2c(N)nc(Nc3ccc(F)cc3C(=N)Cc3c(F)ccc(F)c3F)nc2N)ccn1]

Step A

To a solution of 2,3,-6 trifluoro phenyl acetic acid (0.89 g, 4.73 mmol) and methyl 5-bromo-3-fluoro benzoate in anhydrous THF (15 mL) cooled to −78° C. was added slowly NaHMDS (18.7 mL, 11.26 mmol, 0.6 M). The reaction was warmed to 0° C. After stirring for 30 minutes it was quenched by the addition of 1N HCl (20 mL). The resulting mixture was stirred vigorously at room temperature for 1 hour. The reaction mixture was concentrated to remove the organic solvents. The residue was extracted with EtOAc. The organic layer was washed with 1M potassium carbonate solution (2×), water, and brine, then dried over sodium sulfate, filtered and concentrated. The crude material was carried on to the next step. LC-MS: rt=1.11 min, no m/z detected) $^1$H NMR δ (ppm) (CDCl$_3$): 7.62 (1H, dd, J=8.81, 4.84 Hz), 7.21-7.04 (4H, m), 4.33 (2H, s).

Step B

To a solution of the intermediate from step A (9.0 g, 25.9 mmol) and the intermediate from Example 83 step D (6.80 g, 27.2 mmol) in methanol in a sealed tube was added BF$_3$.OEt$_2$ (9.86 mL, 78 mmol). The resulting mixture was heated at 100° C. for 90 minutes. The reaction mixture was cooled to room temperature and concentrated. The residue was dissolved in ethyl acetate washed with 1M K$_2$CO$_3$ solution (3×), brine, dried over anhydrous sodium sulfate, filtered and concentrated. The crude material was carried on to the next step without any further purification. LC-MS: m/z=580.15 (M+1), retention time=2.46 min (Method C).

Step C

To a solution of the intermediate from step C (15 g, 25.9 mmol) in DMF (30 mL) was added copper (I) iodide (4.94 g, 25.9 mmol) and ethylenediamine (0.85 mL, 7.77 mmol). After stirring at room temperature for 15 minutes, the reaction mixture was diluted with ethyl acetate and washed several times with a 5% ammonium hydroxide solution. The organic layer was washed with brine, dried over anhydrous sodium sulfate, filtered and concentrated. The residue was purified by flash chromatography (Biotage) using a gradient of 5-20% ethyl acetate-hexanes to give the desired product. LC-MS:: m/z=498.07 (M+1); rt=1.31 min (Method B).

Step D

A solution of the intermediate from step C (8 g, 16.07 mmol) in neat benzyl amine (17.5 ml, 161 mmol) was heated at 160° C. for 15 minutes. The reaction mixture was cooled to room temperature, diluted with ethyl acetate and washed with water (4×). The organic layer was dried over anhydrous sodium sulfate, filtered and concentrated. The crude material was carried on to next step without any further purification. LC-MS: m/z=569.27 (M+1); rt-2.43 min (Method C).

Step E

To a solution of the intermediate from step D (9 g, 15.8 mmol) in acetic acid (40 mL) was added bromine (1.6 ml, 31.6 mmol) in AcOH (1 mL). The resulting mixture was stirred at room temperature. Upon completion, it was quenched with water and a 1M sodium sulfite solution and concentrated. The residue was suspended in ethyl acetate and water and neutralized with solid potassium carbonate. The organic layer was washed with brine, dried over anhydrous sodium sulfate, filtered and concentrated. The resulting brownish crystals were triturated with methanol to isolate the desired product as white crystals. LC-MS: m/z=649.14 (M+1); rt=1.38 min (Method B).

Step F

To a solution of the intermediate from step E (70 mg, 0.108 mmol) in 1,4-dioxane (4 mL) was added 3-methoxy-5-pyridine boronic acid (66 mg. 0.54 mmol), 1,1 Bis(Di-tert-butylphosphino)palladium dichloride (3.5 mg, 0.005 mmol) and potassium carbonate solution (1.08 mL, 1M). The resulting mixture was degassed and heated in the microwave reactor at 100° C. for 5 minutes. The reaction mixture was filtered and purified by reverse phase HPLC (Gilson) using a gradient of 65-100% acetonitrile:water to give the desired compound. LC-MS: m/z=676.4 (M+1); rt=1.34 min (Method B).

Step G

To a solution of the intermediate from step F (41 mg, 0.06 mmol) in DCM (2 mL) was added triflic acid (0.68 mL, 7.67 mmol). Upon completion of the reaction it was quenched by the addition of aqueous potassium carbonate solution. The aqueous layer was extracted with 30% iPA/CHCl$_3$ and the organic layer concentrated. The residue was purified by reverse phase HPLC (Gilson) with a gradient of 20-100% acetonitrile:water to give the title compound. LC-MS: m/z=496.13 (M+1), rt=1.07 min (Method B) $^1$H NMR δ (ppm) (DMSO-d$_6$): 8.92 (1H, dd, J=9.28, 4.64 Hz), 8.02 (1H, d, J=2.39 Hz), 7.57-7.43 (3H, m), 7.35 (1H, td, J=9.12, 2.59 Hz), 7.20 (1H, t, J=9.24 Hz), 6.91 (1H, d, J=8.47 Hz), 6.03 (4H, s), 4.43 (2H, s), 3.90 (3H, s).

The following examples were synthesized by following the procedure described in Example 83 and 115.

TABLE 4

| Example | Substituent Z | Retention time (min) | m/z (M + 1) | LC Method |
|---|---|---|---|---|
| 116 | pyridine-CF$_3$ | 1.14 | 534.65 | B |
| 117 | pyridine | 1.07 | 466 | B |
| 118 | F-pyridine | 1.11 | 484 | B |
| 119 | NH$_2$-pyridine | 1.1 | 481 | B |
| 120 | phenyl-SO$_2$Me | 1.11 | 543 | B |

TABLE 4-continued

| Example | Substituent Z | Retention time (min) | m/z (M + 1) | LC Method |
|---|---|---|---|---|
| 121 | quinolin-5-yl | 1.08 | 516 | B |
| 122 | 2-methylpyridin-4-yl | 1.08 | 480 | B |
| 123 | 2-hydroxyquinolin-3-yl | 1.11 | 532 | B |
| 124 | 5-fluoropyridin-3-yl | 1.11 | 483 | B |
| 125 | 2-fluoroquinolin-3-yl | 1.15 | 534 | B |
| 126 | pyridin-4-yl | 1.07 | 466 | B |
| 127 | 1,3,5-trimethyl-1H-pyrazol-4-yl | 1.13 | 497 | B |
| 128 | 1-methyl-5-(trifluoromethyl)-1H-pyrazol-4-yl | 1.12 | 537.1 | B |
| 129 | 1-methyl-3-(trifluoromethyl)-1H-pyrazol-5-yl | 1.14 | 536.87 | B |
| 130 | 3,5-dimethylisoxazol-4-yl | 1.14 | 484.21 | B |

TABLE 4-continued

Common structure (Examples 131–140): 4,6-diamino-5-Z-pyrimidin-2-yl attached to N1 of 5-fluoro-3-(2,3,6-trifluorobenzyl)-1H-indazole.

| Example | Substituent Z | Retention time (min) | m/z (M+1) | LC Method |
|---------|---------------|----------------------|-----------|-----------|
| 131 | 2-methoxypyridin-4-yl | 1.15 | 496.19 | B |
| 132 | 2,4-dimethoxypyrimidin-5-yl | 1.14 | 527.15 | B |
| 133 | 2-methoxypyridin-3-yl | 1.14 | 496.17 | B |
| 134 | 5-methoxypyridin-3-yl | 1.17 | 496.16 | B |
| 135 | 2-methylpyrimidin-5-yl | 1.12 | 481.17 | B |
| 136 | 2-methoxypyrimidin-5-yl | 1.14 | 497.14 | B |
| 137 | 6-methoxypyridin-2-yl | 1.18 | 496.13 | B |
| 138 | 2,6-dimethoxypyridin-3-yl | 1.17 | 526.18 | B |
| 139 | 4-methoxypyridin-3-yl | 1.08 | 496.13 | B |
| 140 | pyrimidin-5-yl | 1.13 | 467.12 | B |

TABLE 4-continued

| Example | Substituent Z | Retention time (min) | m/z (M + 1) | LC Method |
|---|---|---|---|---|
| 141 | 4-fluoro-pyridin-3-yl | 1.16 | 484.14 | B |
| 142 | thiazol-2-yl | 1.13 | 471.8 | B |
| 143 | 4-methyl-2-phenyl-thiazol-5-yl | 1.22 | 562.2 | B |
| 144 | isobutyramido | 2.72 | 472.9 | A |
| 145 | oxazol-2-yl | 1.2 | 456.1 | B |

Example 146

5-(2-methylpyridin-4-yl)-2-[3-(2,3,6-trifluorobenzyl)-1H indazol-1-yl]pyrimidine-4,6-diamine

Step A

To a solution of 2,3,6-trifluoro phenyl acetic acid (6.6 g, 34.7 mmol) and methyl 2-bromo benzoate (4.86 mL, 34.7 mmol) in anhydrous THF (15 mL) cooled to −78° C. was added slowly NaHMDS (18.7 mL, 11.26 mmol, 0.6 M). The reaction was warmed to 0° C. After stirring for 30 minutes it was quenched by the addition of 1N HCl (20 mL). The resulting mixture was stirred vigorously at room temperature for 1 hour. The reaction mixture was concentrated. The residue was extracted with EtOAc, the organic layer was washed with 1M potassium carbonate solution (2×), water and brine, then dried over sodium sulfate, filtered and concentrated. The crude material was carried on to the next step. LC-MS: rt=1.21 min (Method B), no m/z detected, UV signature at 220 nm $^1$H NMR δ (ppm)(CDCl$_3$): 7.70-7.61 (1H, m), 7.52 (1H, t, J=7.66 Hz), 7.50-7.24 (2H, m), 7.12 (1H, qd, J=9.21, 5.07 Hz), 6.90-6.85 (1H, m), 4.37 (2H, s).

Step B

To a solution of the intermediate from step A (11.4 g, 34.6 mmol) and the intermediate from Example 83 step D (8.6 g, 34.6 mmol) in methanol in a sealed tube was added BF$_3$.OEt$_2$ (26.3 mL, 208 mmol). The resulting mixture was heated at 100° C. for 90 minutes. The reaction mixture was cooled to room temperature and concentrated. The residue was dissolved in ethyl acetate washed with 1M K$_2$CO$_3$ solution (3×), brine, dried over anhydrous sodium sulfate, filtered and concentrated. The crude material was carried on to the next step without any further purification. LC-MS: m/z=562.07 (M+1); rt=1.27 min (Method B).

Step C

To a solution of the intermediate from step B (19.4 g, 34.6 mmol) in DMF (30 mL) was added copper (I) iodide (6.59 g, 34.6 mmol) and ethylenediamine (1.89 mL, 17.3 mmol). After stirring at room temperature for 15 minutes, the reaction mixture was diluted with ethyl acetate and washed several times with a 5% ammonium hydroxide solution. The organic layer was washed with brine, dried over anhydrous sodium sulfate, filtered and concentrated. The residue was purified by flash chromatography (Biotage) using a gradient of 5-20% ethyl acetate-hexanes to give the desired product. LC-MS: m/z=480.14 (M+1); rt=1.28 min (Method B).

Step D

A solution of the intermediate from step C (16 g, 33.3 mmol) in neat benzyl amine (36.4 ml, 333 mmol) was heated at 160° C. for 15 minutes. The reaction mixture was cooled to room temperature, diluted with ethyl acetate and washed with water (4×). The organic layer was dried over anhydrous sodium sulfate, filtered, and concentrated. The crude material was carried on to next step without any further purification. LC-MS: m/z=551.30 (M+1); rt=2.32 min (Method B).

Step E

To a solution of the intermediate from step D (12 g, 21.8 mmol) in acetic acid (80 mL) was added bromine (3.3 ml, 65.4 mmol) in AcOH (1 mL). The resulting mixture was stirred at room temperature. Upon completion, it was quenched with water and a 1M sodium sulfite solution and concentrated. The residue was suspended in ethyl acetate and water and neutralized with solid potassium carbonate. The organic layer was washed with brine, dried over anhydrous sodium sulfate, filtered and concentrated. The resulting residue was triturated with methanol to isolate the desired product as white crystals. LC-MS: m/z=631.14 (M+1); rt-1.37 min (Method B).

Step F

To a solution of the intermediate from step E (300 mg, 0.477 mmol) in 1,4-dioxane (20 mL) was added 2-methylpyridine boronic acid from Example 4 step A (131 mg. 0.953 mmol), 1,1 Bis(Di-tert-butylphosphino)palladium dichloride (15.5 mg, 0.024 mmol) and potassium carbonate solution (4.77 mL, 1M). The resulting mixture was degassed and heated in the microwave reactor at 100° C. for 5 minutes. The reaction mixture was filtered and purified by reverse phase HPLC (Gilson) using a gradient of 65-100% acetonitrile: water to give the desired compound. LC-MS: m/z=642.29 (M+1); rt=1.25 min (Method B).

Step G

To a solution of the intermediate from step F (41 mg, 0.06 mmol) in DCM (10 mL) was added triflic acid (152 µL, 1.71 mmol). Upon completion of the reaction it was quenched by the addition of aqueous potassium carbonate solution. The aqueous layer was extracted with 30% iPA/CHCl₃. DMF (15 mL) was added and organic layer concentrated. The residue was purified by reverse phase HPLC (Gilson) to give the title compound. LC-MS: m/z=462.10 (M+1), rt=1.05 min (Method B); $^1$H NMR δ (ppm) (DMSO-d$_6$): 8.89 (1H, d, J=8.65 Hz), 8.50 (1H, d, J=5.35 Hz), 7.70 (1H, d, J=8.12 Hz), 7.48 (2H, t, J=8.59 Hz), 7.28 (1H, t, J=7.81 Hz), 7.18 (2H, s), 7.11 (1H, d, J=5.24 Hz), 6.13 (4H, s), 4.44 (2H, s), 3.55 (3H, s). The following examples were synthesized using the procedures described in Examples 83, 115 and 146.

TABLE 5

| Example | Substituent Z | Retention time (min) | m/z (M + 1) | LC Method |
|---|---|---|---|---|
| 147 | 2-fluoropyridin-4-yl | 1.11 | 466 | B |
| 148 | 1,3,5-trimethylpyrazol-4-yl | 1.14 | 479 | B |
| 149 | 5-fluoropyridin-3-yl | 1.09 | 500 | B |
| 150 | 1-methylpyrazol-4-yl | 1.09 | 466 | B |
| 151 | 2-methylpyridin-5-yl | 1.08 | 450 | B |

TABLE 5-continued
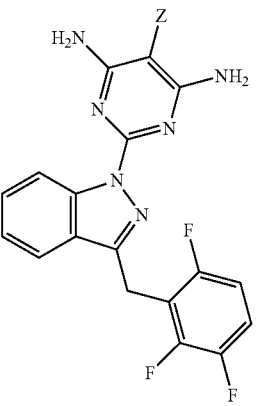
| Example | Substituent Z | Retention time (min) | m/z (M + 1) | LC Method |
|---|---|---|---|---|
| 152 | 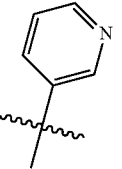 [SMILES: *c1cccnc1] | 1.09 | 448 | B |
| 153 | 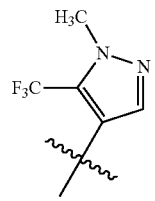 | 1.08 | 448 | B |
| 154 | 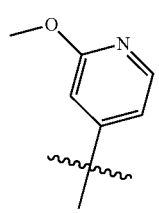 [SMILES: *c1ccnc(OC)c1] | 1.12 | 519.1 | B |
| 155 | 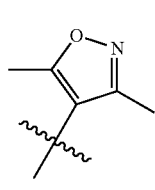 | 1.95 | 478.19 | C |
| 156 | 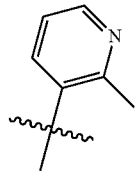 [SMILES: *c1cccnc1C] | 1.11 | 466.2 | B |
| 157 | 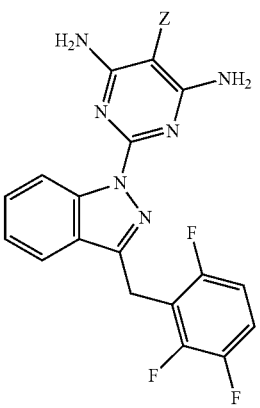 | 1.69 | 462.18 | C |
| 158 | 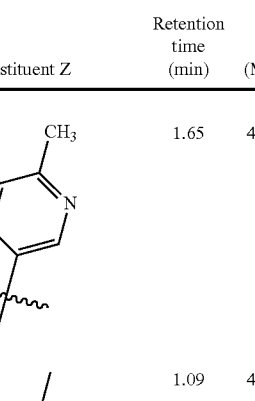 | 1.65 | 462.1 | C |
| 159 | 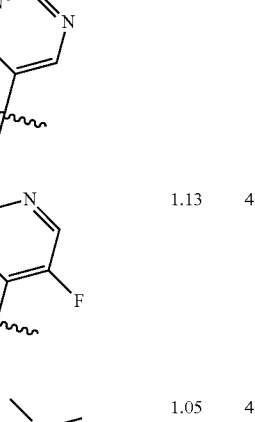 | 1.09 | 463.1 | B |
| 160 | 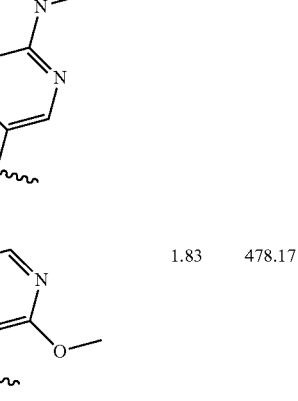 | 1.13 | 466.15 | B |
| 161 |  | 1.05 | 491.18 | B |
| 162 | | 1.83 | 478.17 | C |

TABLE 5-continued

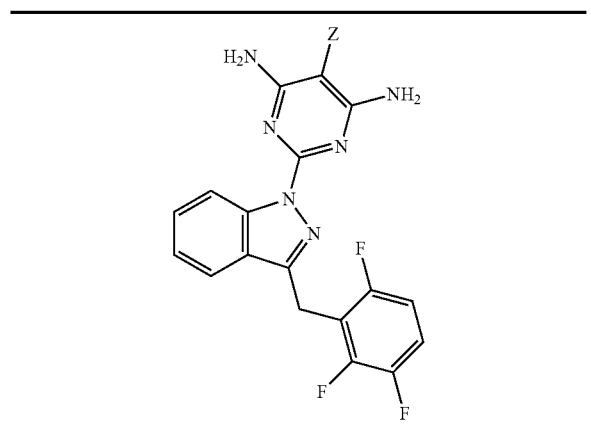

| Example | Substituent Z | Retention time (min) | m/z (M + 1) | LC Method |
|---|---|---|---|---|
| 163 | (2-methoxypyridin-5-yl) | 1.87 | 478.14 | C |
| 164 | (2-phenyl-4-methylthiazol-5-yl) | 1.2 | 544.17 | B |
| 165 | (pyrazin-2-yl) | 1.12 | 449.2 | B |
| 166 | (4-methoxypyridin-3-yl) | 1.05 | 478.1 | B |
| 167 | (2,6-dimethoxypyridin-3-yl) | 1.15 | 508.18 | B |

TABLE 5-continued

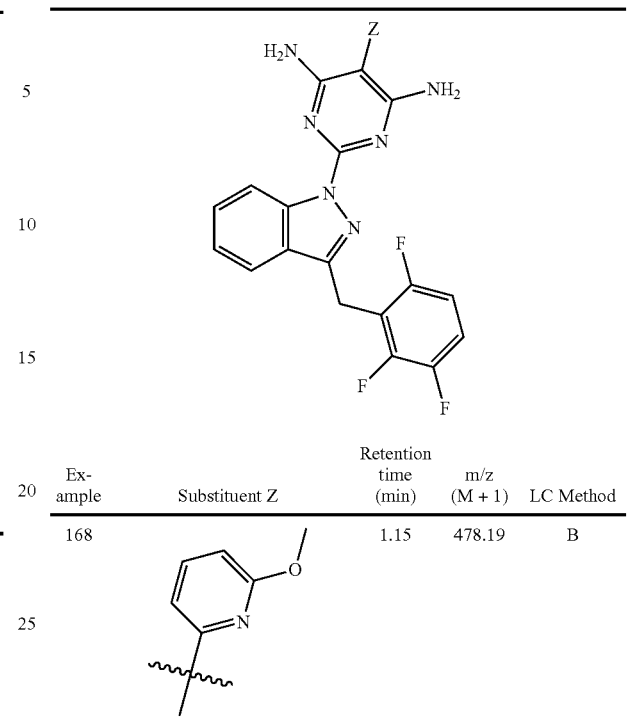

| Example | Substituent Z | Retention time (min) | m/z (M + 1) | LC Method |
|---|---|---|---|---|
| 168 | (6-methoxypyridin-2-yl) | 1.15 | 478.19 | B |
| 169 | (pyridin-2-yl) | 1.09 | 448.17 | B |

TABLE 6

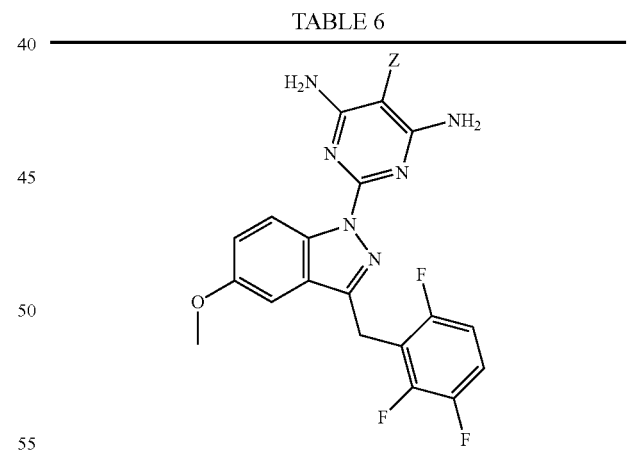

| Example | Substituent Z | Retention time (min) | m/z (M + 1) | LC Method |
|---|---|---|---|---|
| 170 | (1-methylpyrazol-4-yl) | 1.13 | 422.17 | B |

TABLE 6-continued
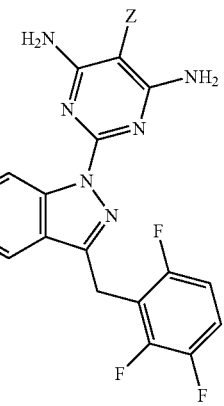
| Example | Substituent Z | Retention time (min) | m/z (M + 1) | LC Method |
|---|---|---|---|---|
| 171 | | 1.08 | 477.95 | B |
| 172 | | 1.13 | 546.02 | B |
| 173 | | 1.64 | 509.01 | C |
TABLE 7
| Example | Structure | Retention time (min) | m/z (M + 1) | LC Method |
|---|---|---|---|---|
| 174 | 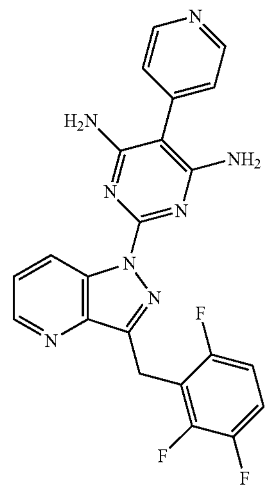 [SMILES: Nc1nc(-n2nc(Cc3c(F)ccc(F)c3F)c3ncccc32)nc(N)c1-c1ccncc1] | 2.47 | 449.3 | A |
| 175 | 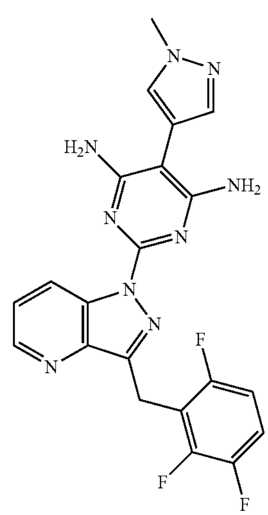 [SMILES: Cn1cc(-c2c(N)nc(-n3nc(Cc4c(F)ccc(F)c4F)c4ncccc43)nc2N)cn1] | 2.58 | 452.3 | A |

Example 176 methyl {4,6-diamino-2-[5-chloro-3-(2,3,6-trifluorobenzyl)-1H-indazol-1-yl]pyrimidin-5-yl}carbamate

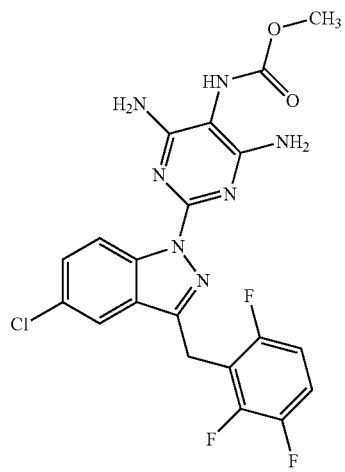 [SMILES: COC(=O)Nc1c(N)nc(-n2nc(Cc3c(F)ccc(F)c3F)c3cc(Cl)ccc32)nc1N]

Step A

Solid 4,6-dihydroxy-2-(methylthio)pyrimidine (10 g, 63.mmol) was added in portions over 30 min. to fuming nitric acid (30 ml) cooled in an ice bath. After stirring for 90 min in an ice bath the solution was poured over ice. The product was collected by filtration, washed with a small amount of ice water and air dried on the filter. $^1$H NMR (400 MHz, CDCl$_3$): δ 7.02 (s, 2H); 2.56 (s, 3H). LC rt=0.49 min (Method A, not ionized).

Step B

Phosphorous oxychloride (20 ml) was added slowly to a suspension of the intermediate from Step A (5 g, 24.6 mmol) and diethyl-aniline (6 ml, 37.7 mmol) cooled in an ice bath. The mixture was then refluxed for 1 hour. The reaction was cooled and concentrated. The residue was partitioned between EtOAc and aqueous 1N HCl. The organic phase was washed with water, brine, dried over anhydrous sodium sulfate filtered and concentrated to give the indicated product, $^1$H NMR (400 MHz, CDCl$_3$): δ 2.98 (s, 3H). LC rt=3.3 min (Method A, not ionized).

Step C

To a 1,4-dioxane (50 ml) solution of the intermediate from Step B (11.8 g, 49.2 mmol) was added DIEA (25.8 ml, 148 mmol) and benzylamine (16.1 ml, 148 mmol). After stirring at room temperature for several hours, the solution was concentrated and the residue partitioned between EtOAc and aqueous 1N HCl. The organic phase was washed with aqueous 1N HCl followed by aqueous 1N NaOH and brine. The organic phase was then dried over anhydrous sodium sulfate filtered and concentrated to give the indicated product. LC-MS: m/z=382 (M+1); rt-3.86 min (Method A); $^1$H NMR (400 MHz, CDCl$_3$): δ 9.66 (s, 2H); 7.37-7.25 (m, 10H); 4.81 (d, J=5.67 Hz, 4H); 2.43 (s, 3H).

Step D m-Chloroperoxybenzoic acid (32.4 g, 55%, 103 mmol) was added in portions to a DCM (50 ml) solution of the intermediate from Step C (17.9 g, 47.0 mmol). An additional 200 ml of DCM was added and the reaction mixture was stirred at room temperature for 24 hours. The mixture was cooled in an ice bath and filtered. The solid was washed with a small amount of DCM and the filtrate solution was concentrate to half volume. The DCM filtrate solution was then washed with sodium thiosulfate (2×), 1N NaOH (2×) and brine. The organic phase was then dried over anhydrous magnesium sulfate filtered and concentrated to give the indicated product. LC-MS: m/z=411 (M+1); rt-3.23 min (Method A).

Step E

The intermediate from Step D (18.7 g, 45.3 mmol) was suspended in 1,4-dioxane (100 ml) and hydrazine hydrate (11.0 ml, 226 mmol) was added. The solution was stirred at room temperature for 1 hour and then concentrated. The residue was suspended in MeOH which formed a heavy precipitate. The crude solid was collected by filtration, washed with cold MeOH and air dried on the filter to give the indicated product. LC-MS: m/z=366 (M+1); rt=2.72 min (Method A); $^1$H NMR (400 MHz, CDCl$_3$): δ 9.94 (broad s, 1H); 9.74 (broad s, 1H); 7.37-7.23 (m, 10H); 4.73 (broad s, 4H).

Step F

A MeOH (15 ml) solution of ketone intermediate from Example 83 step A (1 g, 2.75 mmol), hydrazine intermediate from step E (1.0 g, 2.75 mmol) and boron trifluoride etherate (1.05 ml, 8.2 mmol) were heated in a screw cap pressure tube at 100° C. for 90 min. The solution was then concentrated and the residue partitioned between EtOAc and aqueous NaOH. The organic phase was washed with brine, dried over anhydrous magnesium sulfate filtered and concentrated to give the indicated product. The isolated material was used in the following step without purification. LC-MS: m/z=710 (M+1); rt=4.25 min (Method A).

Step G

A NMP (15 ml) solution of the intermediate form Step F (1.95 g, 2.7 mmol), 1,2-trans-N,N'-dimethyldiaminocylcohexane (0.04 ml, 0.27 mmol) and copper iodide (0.52 g, 2.74 mmol) were heated at 160° C. for 20 minutes. The solution was cooled to room temperature and diluted with EtOAc. The solution was then washed with 5% aqueous ammonium hydroxide (2×) and brine. The organic phase was washed with brine, dried over anhydrous magnesium sulfate filtered and concentrated. The residue was purified by silica gel chromatography using a EtOAc/hexanes/DCM eluent, LC-MS: m/z=630 (M+1); rt=1.35 min (Method B).

Step H

A solution of the intermediate from Step G (200 mg, 0.32 mmol) and tin chloride dihydrate (558 mg, 2.47 mmol) in 1,4-dioxane (5 ml) and ethanol (5 ml) was heated at 90° C. for 48 hours. The solution was cooled to room temperature and a potassium fluoride solution was added (600 mg KF/10 ml water). After stirring for 1 hour the mixture was filtered through celite. The filtrate was diluted with EtOAc and washed with KF solution, water and brine. The organic phase was dried over anhydrous magnesium sulfate filtered and concentrated. The residue was used without purification in the following step. LC-MS: m/z=600 (M+1); rt-3.85 min (Method A).

Step 1

Methyl chloroformate (0.035 ml, 0.455 mmol) was added to a pyridine (2.5 ml) solution of the crude intermediate from Step H (273 mg, ca 0.455 mmol) cooled to 0° C. After 10 minutes the solution was warmed to room temperature and stirred an additional 30 minutes. The solution was then diluted with EtOAc and washed with 1N NaOH and brine. The organic phase was then dried over anhydrous magnesium sulfate filtered and concentrated. The residue was purified by silica gel chromatography using a EtOAc/DCM eluent to give the indicated product. LC-MS: m/z=658 (M+1); rt=3.96 min (Method A).

Step J

The intermediate from Step 1 (75 mg, 0.11 mmol) was suspended in DCM (3 ml) and excess triflic acid (15 drops) was added. After stirring for 1 hour at room temperature the reaction was quenched with 10% ammonium hydroxide in MeOH. The solution was concentrated and the residue purified by preparative TLC using 10% MeOH/DCM (with 1% aqueous ammonium hydroxide) as the eluent to give the indicated product. LC-MS: m/z=478 (M+1); rt=2.94 min (Method A); $^1$H NMR (500 MHz, DMSO-$d_6$): δ 8.82 (d, J=9.03 Hz, 1H); 7.89 (s, 1H); 7.83 (d, J=1.99 Hz, 1H); 7.49-7.41 (m, 1H); 7.18 (t, J=9.75 Hz, 1H); 7.10 (broad s, 1H); 6.35 (s, 4H); 4.42 (s, 3H); 3.60 (s, 2H).

Example 177 methyl {4,6-diamino-2-[5-chloro-3-(2,3,6-trifluorobenzyl)-1H-indazol-1-yl]pyrimidin-5-yl}methylcarbamate

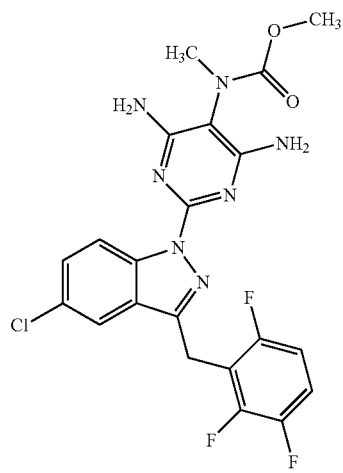 [SMILES: COC(=O)N(C)c1c(N)nc(-n2nc(Cc3c(F)ccc(F)c3F)c3cc(Cl)ccc32)nc1N]

Step A

An acetone (4 ml) solution containing the intermediate from Example 176 Step 1 (75 mg, 0.114 mmol), methyl iodide (0.07 ml, 1.24 mmol) and potassium carbonate (315 mg, 2.28 mmol) was heated at 45° C. overnight. The solution was concentrated and the residue partitioned between EtOAC and water. The organic phase was washed with brine dried over anhydrous magnesium sulfate filtered and concentrated to give the indicated product. LC-MS: m/z=672 (M+1); rt=2.97 min (Method C).

Step B

The indicated product was prepared from the intermediate from Step A using triflic acid as described in Example 176 Step J. LC-MS: m/z=492 (M+1); rt=3.09 min (Method A). NMR (500 MHz, DMSO-$d_6$): δ 8.82 (d, J=9.09 Hz, 1H); 7.84 (s, 1H); 7.51-7.43 (m, 2H); 7.19 (t, J=9.23 Hz, 1H); 6.55 (s, 4H); 4.43 (s, 2H); 3.65 (s, 1H, CO2Me rotamer); 3.53 (s, 2H, CO2Me rotamer); 2.99 (s, 3H).

Example 178

N-{4,6-diamino-2-[5-chloro-3-(2,3,6-trifluorobenzyl)-1H-indazol-1-yl]pyrimidin-5-yl}cyclopropanecarboxamide

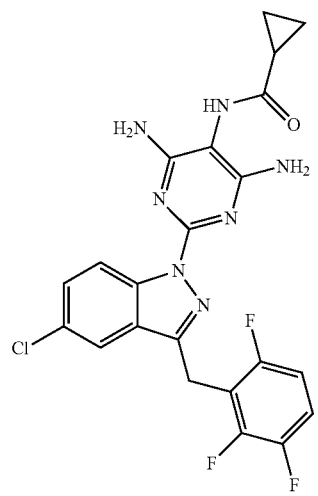 [SMILES: Nc1nc(-n2nc(Cc3c(F)ccc(F)c3F)c3cc(Cl)ccc32)nc(N)c1NC(=O)C1CC1]

The indicated product was prepared from the intermediate from Example 176 step H using the procedure described in Example 176 Step I (substituting methyl chloroformate with cyclopropanecarbonyl chloride). LC-MS: m/z=488 (M+1); rt=2.93 min (Method A); $^1$H NMR (500 MHz, DMSO-$d_6$): δ 8.91 (s, 1H); 8.85 (d, J=8.9 Hz, 1H); 7.85 (d, J=2.00 Hz, 1H); 7.51-7.43 (m, 2H); 7.20 (m, 1H); 6.22 (s, 4H); 4.44 (s, 2H); 1.82-1.75 (m, 1H); 0.83-0.72 (m, 4H).

Example 179

S-methyl {4,6-diamino-2-[5-chloro-3-(2,3,6-trifluorobenzyl)-1H-indazol-1-yl]pyrimidin-5-yl}thiocarbamate

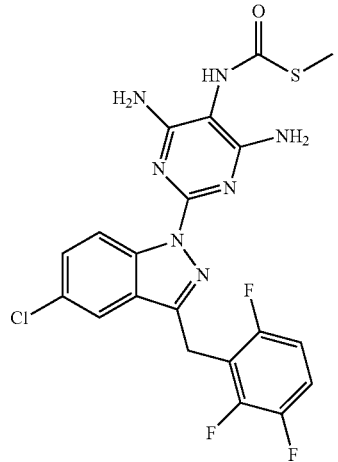 [SMILES: CSC(=O)Nc1c(N)nc(-n2nc(Cc3c(F)ccc(F)c3F)c3cc(Cl)ccc32)nc1N]

The indicated product was prepared from the intermediate from Example 176 step H using the procedure described in Example 176 Step I (substituting methyl chloroformate with methyl chlorothiolformate). LC-MS: m/z=494 (M+1); rt=1.08 min (Method B); ¹H NMR (500 MHz, rotamers, DMSO-d₆): δ 8.94-8.83 (m, 1H); 8.47 (s, 1H); 7.85 (d, J=1.96 Hz, 1H); 7.51-7.43 (m, 2H); 7.20 (t, J=9.27 Hz, 1H); 6.55 (broad s, 3H, rotamer); 6.29 (broad s, 1H, rotamer); 4.44 (s, 2H); 2.29 (s, H, rotamer); 2.12 (s, 2H, rotamer).

The following examples were synthesized using the procedures described in Examples 176-179.

TABLE 8

| Example | Structure | Retention time (min) | m/z (M + 1) | LC Method |
|---------|-----------|----------------------|-------------|-----------|
| 180 | 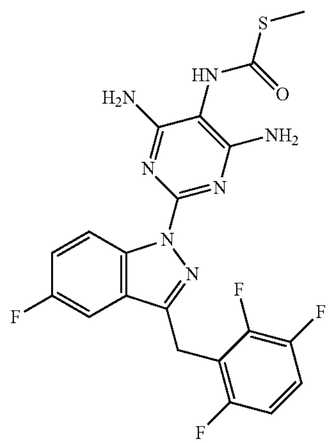 [SMILES: CSC(=O)Nc1c(N)nc(-n2nc(Cc3c(F)ccc(F)c3F)c3cc(F)ccc32)nc1N] | 2.87 | 478 | A |
| 181 | 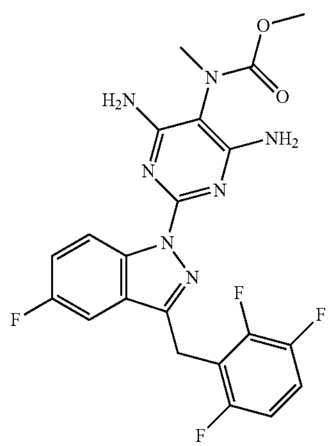 [SMILES: COC(=O)N(C)c1c(N)nc(-n2nc(Cc3c(F)ccc(F)c3F)c3cc(F)ccc32)nc1N] | 2.90 | 476 | A |
| 182 | 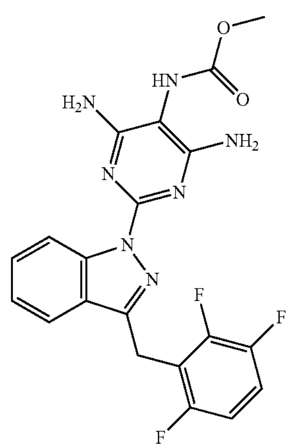 [SMILES: COC(=O)Nc1c(N)nc(-n2nc(Cc3c(F)ccc(F)c3F)c3ccccc32)nc1N] | 2.68 | 444 | A |

TABLE 8-continued

| Example | Structure | Retention time (min) | m/z (M + 1) | LC Method |
|---------|-----------|----------------------|-------------|-----------|
| 183 | 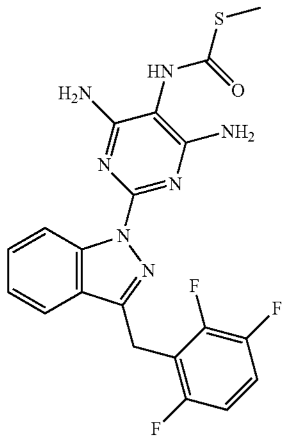 [SMILES: CSC(=O)Nc1c(N)nc(-n2nc(Cc3c(F)ccc(F)c3F)c3ccccc32)nc1N] | 1.04 | 460 | B |
| 184 | 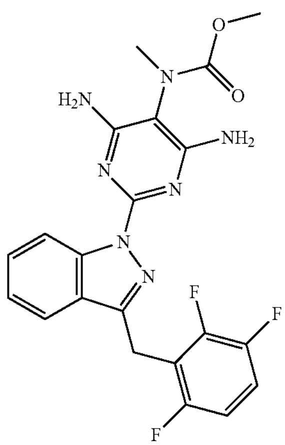 [SMILES: COC(=O)N(C)c1c(N)nc(-n2nc(Cc3c(F)ccc(F)c3F)c3ccccc32)nc1N] | 2.81 | 458 | A |
| 185 | 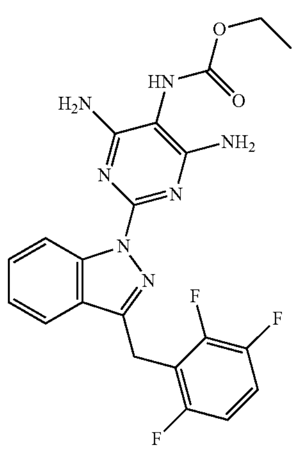 [SMILES: CCOC(=O)Nc1c(N)nc(-n2nc(Cc3c(F)ccc(F)c3F)c3ccccc32)nc1N] | 2.78 | 458 | A |

TABLE 8-continued

| Example | Structure | Retention time (min) | m/z (M + 1) | LC Method |
|---|---|---|---|---|
| 186 | 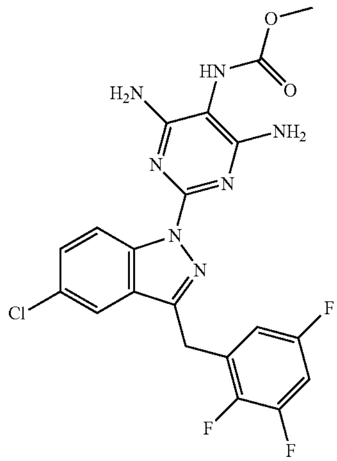 [SMILES: COC(=O)Nc1c(N)nc(-n2nc(Cc3cc(F)cc(F)c3F)c3cc(Cl)ccc32)nc1N] | 2.97 | 478 | A |
| 187 | 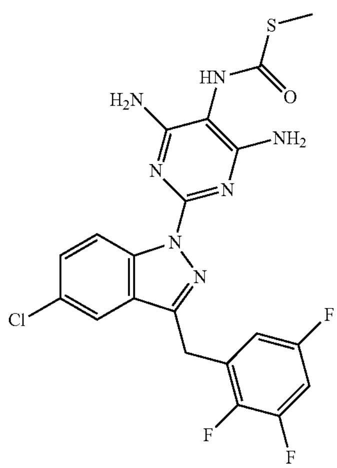 [SMILES: CSC(=O)Nc1c(N)nc(-n2nc(Cc3cc(F)cc(F)c3F)c3cc(Cl)ccc32)nc1N] | 1.48 | 494 | B |
| 188 | 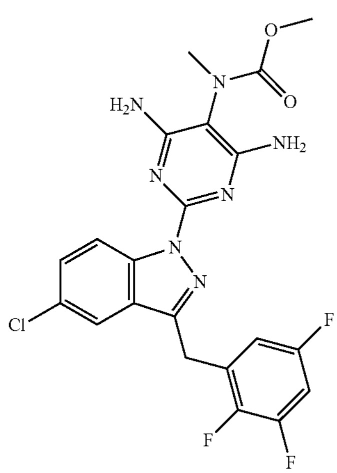 [SMILES: COC(=O)N(C)c1c(N)nc(-n2nc(Cc3cc(F)cc(F)c3F)c3cc(Cl)ccc32)nc1N] | 3.06 | 492 | A |

TABLE 8-continued

| Example | Structure | Retention time (min) | m/z (M + 1) | LC Method |
|---------|-----------|----------------------|-------------|-----------|
| 189 | 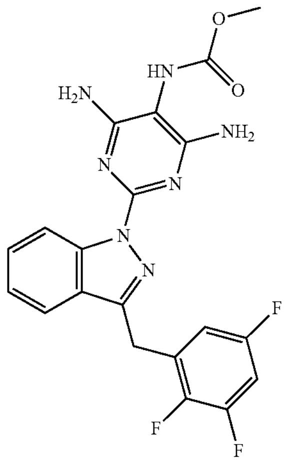 [SMILES: COC(=O)Nc1c(N)nc(-n2nc(Cc3cc(F)cc(F)c3F)c3ccccc32)nc1N] | 1.02 | 444 | B |
| 190 | 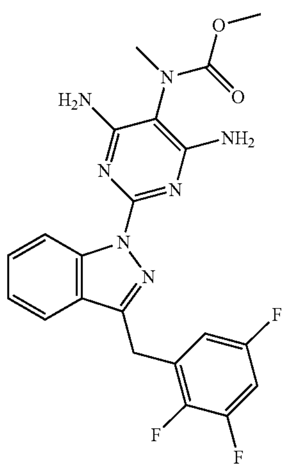 [SMILES: COC(=O)N(C)c1c(N)nc(-n2nc(Cc3cc(F)cc(F)c3F)c3ccccc32)nc1N] | 2.84 | 458 | A |
| 191 | 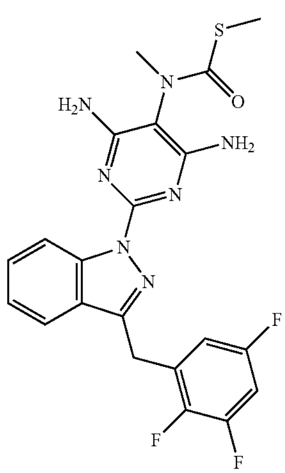 [SMILES: CSC(=O)N(C)c1c(N)nc(-n2nc(Cc3cc(F)cc(F)c3F)c3ccccc32)nc1N] | 1.38 | 460 | B |

TABLE 8-continued
| Example | Structure | Retention time (min) | m/z (M + 1) | LC Method |
|---|---|---|---|---|
| 192 | 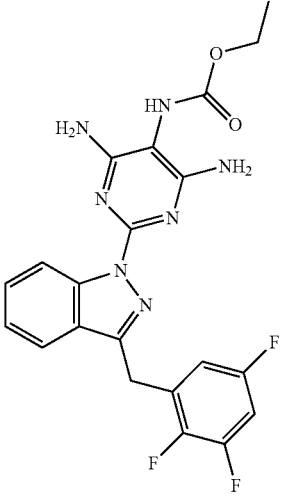 [SMILES: CCOC(=O)Nc1c(N)nc(-n2nc(Cc3cc(F)cc(F)c3F)c3ccccc32)nc1N] | 1.09 | 458 | B |
| 193 | 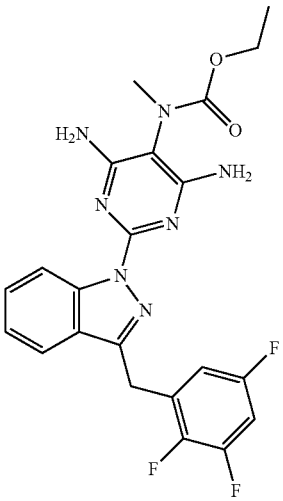 [SMILES: CCOC(=O)N(C)c1c(N)nc(-n2nc(Cc3cc(F)cc(F)c3F)c3ccccc32)nc1N] | 2.91 | 472 | A |
| 194 | 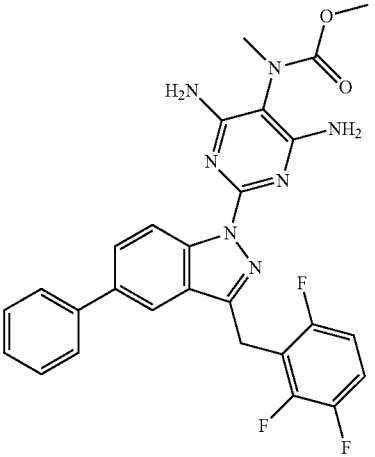 [SMILES: COC(=O)N(C)c1c(N)nc(-n2nc(Cc3c(F)ccc(F)c3F)c3cc(-c4ccccc4)ccc32)nc1N] | 2 | 534 | C |

TABLE 8-continued

| Example | Structure | Retention time (min) | m/z (M + 1) | LC Method |
|---|---|---|---|---|
| 195 | 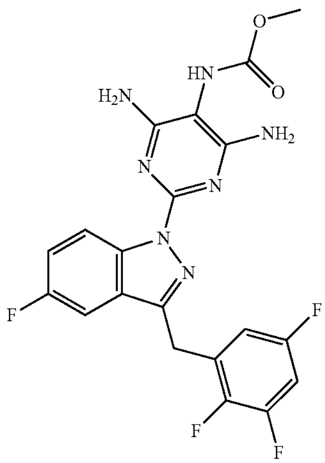 [SMILES: COC(=O)Nc1c(N)nc(-n2nc(Cc3cc(F)cc(F)c3F)c3cc(F)ccc32)nc1N] | 2.78 | 462 | A |
| 196 | 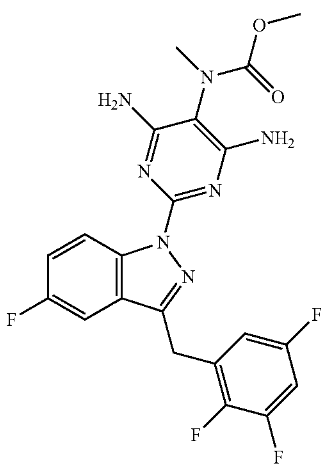 [SMILES: COC(=O)N(C)c1c(N)nc(-n2nc(Cc3cc(F)cc(F)c3F)c3cc(F)ccc32)nc1N] | 2.88 | 476 | A |
| 197 | 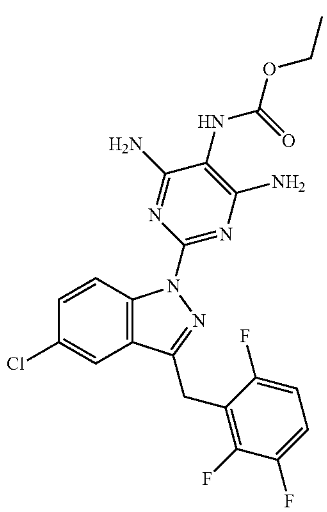 [SMILES: CCOC(=O)Nc1c(N)nc(-n2nc(Cc3c(F)ccc(F)c3F)c3cc(Cl)ccc32)nc1N] | 1.07 | 492 | B |

TABLE 8-continued

| Example | Structure | Retention time (min) | m/z (M + 1) | LC Method |
|---|---|---|---|---|
| 198 | 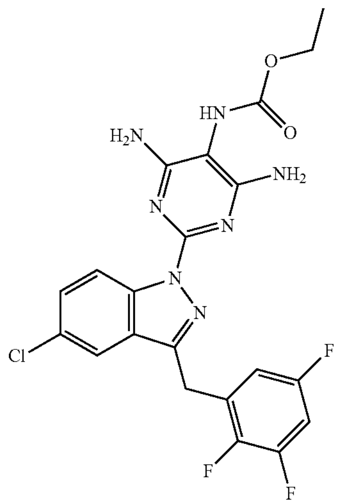 [SMILES: CCOC(=O)Nc1c(N)nc(-n2nc(Cc3cc(F)cc(F)c3F)c3cc(Cl)ccc32)nc1N] | 2.98 | 492 | A |
| 199 | 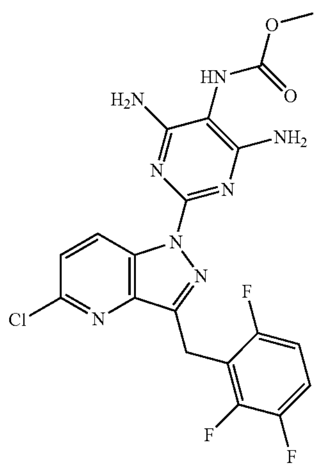 [SMILES: COC(=O)Nc1c(N)nc(-n2nc(Cc3c(F)ccc(F)c3F)c3nc(Cl)ccc32)nc1N] | 1.05 | 479 | B |
| 200 | 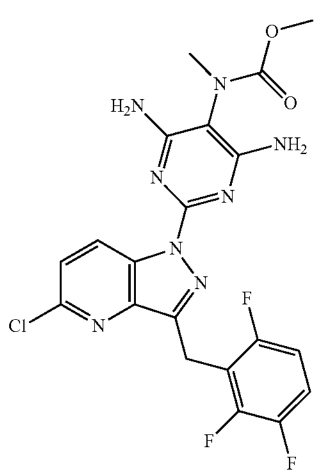 [SMILES: COC(=O)N(C)c1c(N)nc(-n2nc(Cc3c(F)ccc(F)c3F)c3nc(Cl)ccc32)nc1N] | 1.1 | 493 | B |

TABLE 8-continued
| Example | Structure | Retention time (min) | m/z (M + 1) | LC Method |
|---|---|---|---|---|
| 201 | 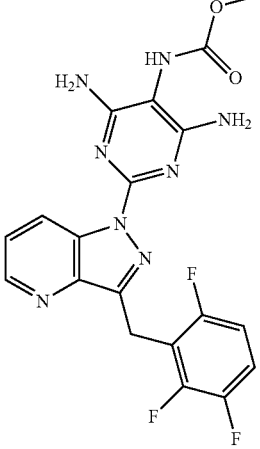 | 1.0 | 445 | B |
| 202 | 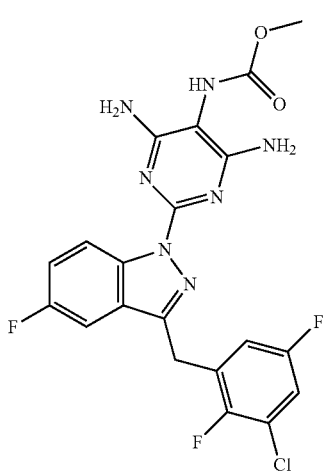 [SMILES: COC(=O)Nc1c(N)nc(-n2nc(Cc3cc(F)cc(Cl)c3F)c3cc(F)ccc32)nc1N] | 2.83 | 478 | A |
| 203 | 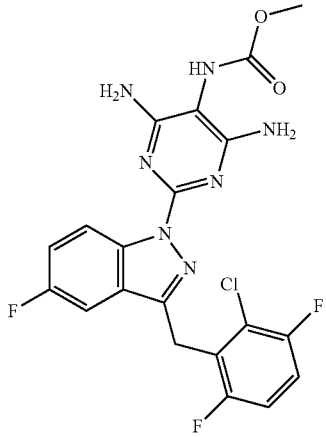 | 2.8 | 478 | A |

TABLE 8-continued

| Example | Structure | Retention time (min) | m/z (M + 1) | LC Method |
|---|---|---|---|---|
| 204 | 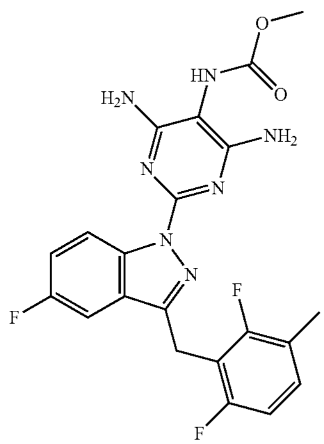 [SMILES: COC(=O)Nc1c(N)nc(-n2nc(Cc3c(F)ccc(C)c3F)c3cc(F)ccc32)nc1N] | 2.94 | 458 | D |
| 205 | 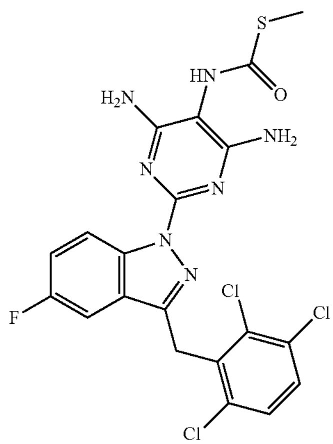 [SMILES: CSC(=O)Nc1c(N)nc(-n2nc(Cc3c(Cl)ccc(Cl)c3Cl)c3cc(F)ccc32)nc1N] | 3.12 | 526 | A |
| 206 | 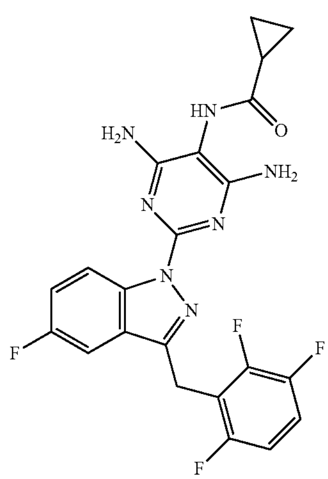 [SMILES: Nc1nc(-n2nc(Cc3c(F)ccc(F)c3F)c3cc(F)ccc32)nc(N)c1NC(=O)C1CC1] | 2.71 | 472 | A |

| Example | Structure | Retention time (min) | m/z (M + 1) | LC Method |
|---|---|---|---|---|
| 207 | 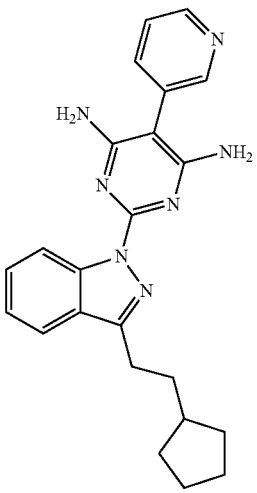 [SMILES: Nc1nc(-n2nc(CCC3CCCC3)c3ccccc32)nc(N)c1-c1cccnc1] | 2.71 | 454 | A |

Example 208

2-[3-(2-cyclopentylethyl)-1H-indazol-1-yl]-5-pyridin-3-ylpyrimidine-4,6-diamine

Step A

To a solution of 2-bromo benzoyl chloride (7.92 ml, 60.6 mmol) and DIEA (21.17 ml, 121 mmol) in DCM (121 ml) was added a solution of N,O-dimethyl hydroxylamine hydrochloride (5.91 g, 60.6 mmol) in DCM (121 ml). After 30 minutes, the reaction was diluted with ethyl acetate, washed with brine, dried over sodium sulfate, filtered and concentrated. The residue was purified by flash chromatography using a gradient of 0-100% ethyl acetate/hexanes.

Step B

To a solution of cyclopentyl acetylene (700 mg, 7.43 mmol) and Weinreb amide from step A (1815 mg, 7.43 mmol) cooled to −78° C. was added LiHMDS (7.43 mL, 7.43 mmol). After 15 min, the ice bath was removed and the reaction was warmed to room temperature. The reaction mixture was quenched by adding saturated ammonium chloride solution. The resulting mixture was extracted with ethyl acetate, washed with brine, dried over sodium sulfate, filtered and concentrated. The residue was purified by flash chromatography Biotage SPI using a gradient of 0-100% ethyl acetate/hexanes to give the desired compound.

Step C

To a solution of the intermediate from step B (300 mg, 1.08 mmol) in ethyl acetate (20 mL) was added to platinum (IV) oxide (25 mg, 0.108 mmol). The resulting reaction mixture was stirred under hydrogen balloon for 24 hours. The reaction was filtered through celite. The filtrate was concentrated and used in the next step without any further purification. $^1$H NMR (CDCl$_3$, 500 MHz) δ 7.62 (d, 1H), 7.38 (d, 2H), 7.30 (m, 1H), 2.95 (t, 2H), 1.85-1.72 (m, 5H), 1.67-1.53 (m, 4H), 1.15 (m, 2H).

Step D

To a solution of the intermediate from step C (2 g, 7.11 mmol) and the intermediate from Example 83 step D (1.77 g, 7.11 mmol) in methanol (36 mL) in a sealed tube was added BF$_3$.OEt$_2$ (2.7 mL, 21.34 mmol). The resulting mixture was heated at 100° C. for 90 minutes. The reaction mixture was cooled to room temperature and concentrated. The residue was dissolved in ethyl acetate washed with 1M K$_2$CO$_3$ solution (3×), brine, dried over anhydrous sodium sulfate, filtered and concentrated. The crude material was carried on to the next step without any further purification.

Step E

To a solution of the intermediate from step D (7.11 mmol) in DMF (36 mL) was added copper (I) iodide (1.35 g, 7.11 mmol) and ethylenediamine (1.89 mL, 17.3 mmol). After stirring at room temperature for 15 minutes, the reaction mixture was diluted with ethyl acetate and washed several times with a 5% ammonium hydroxide solution. The organic layer was washed with brine, dried over anhydrous sodium sulfate, filtered and concentrated. The residue was purified by flash chromatography (Biotage) using a gradient of 0-100% ethyl acetate-hexanes to give the desired product.

Step F

A solution of the intermediate from step F (2 g, 4.63 mmol) in neat benzyl amine (0.51 ml, 4.63 mmol) was heated at 160° C. for 15 minutes. The reaction mixture was cooled to room temperature, diluted with ethyl acetate and washed with water (4x). The organic layer was dried over anhydrous sodium sulfate, filtered and concentrated. The crude material was carried on to next step without any further purification.

Step G

To a solution of the intermediate from step F (4.63 mmol) in acetic acid (15 mL) was added bromine (0.24 ml, 4.63 mmol) in AcOH (3 mL). The resulting mixture was stirred at room temperature. Upon completion, it was quenched with water and a 1M sodium sulfite solution and concentrated. The residue was suspended in ethyl acetate and water and neutralized with solid potassium carbonate. The organic layer was washed with brine, dried over anhydrous sodium sulfate, filtered and concentrated. The residue was purified by flash chromatography Biotage SP1 using a gradient of 0-30% ethyl acetate-hexanes.

Step H

To a solution of the intermediate from step G (100 mg, 0.172 mmol) in 1,4-dioxane (2 mL) was added 3-pyridine boronic acid (106 mg. 0.86 mmol), 1,1 Bis(Di-tert-butylphosphino)palladium dichloride (1.1 mg, 1.72 mmol) and potassium carbonate solution (1.72 mL, 1M). The resulting mixture was degassed and heated in the microwave reactor at 90° C. for 10 minutes. The reaction mixture was filtered and purified by reverse phase HPLC (Gilson) using a gradient of 30-100% acetonitrile:water to give the desired compound.

Step I

To a solution of the intermediate from step H (41 mg, 0.06 mmol) in DCM (2 mL) was added triflic acid (122 µL, 1.37 mmol). Upon completion of the reaction it was quenched by the addition of aqueous potassium carbonate solution. The aqueous layer was extracted with 30% iPA/CHCl$_3$. DMF (15 mL) was added and organic layer concentrated. The residue was purified by reverse phase HPLC (Gilson) to give the title compound. LC-MS: mk=400.13 (M+1); rt=1.05 min, (Method B); $^1$H NMR (DMSO-d$_6$, 500 MHz) δ8.87 (d, 1H), 8.58 (d, 1H), 8.47 (s, 1H), 7.80 (d, 1H), 7.72 (d, 1H), 7.51-7.45 (m, 2H), 7.27 (t, 1H), 6.15 (s, 4H), 2.97 (t, 2H), 1.80-1.75 (m, 5H), 1.59 (m, 2H), 1.48 (m, 2H), 1.15 (m, 2H).

The following examples were synthesized using the procedures described in Example 208.

TABLE 9

| Example | Structure | Retention time (min) | m/z (M + 1) | LC Method |
|---|---|---|---|---|
| 209 | 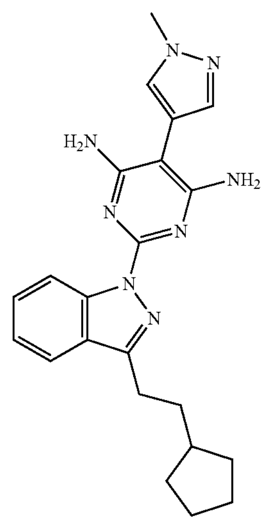 [SMILES: Cn1cc(-c2c(N)nc(-n3nc(CCC4CCCC4)c4ccccc43)nc2N)cn1] | 1.13 | 403.2 | B |
| 210 | 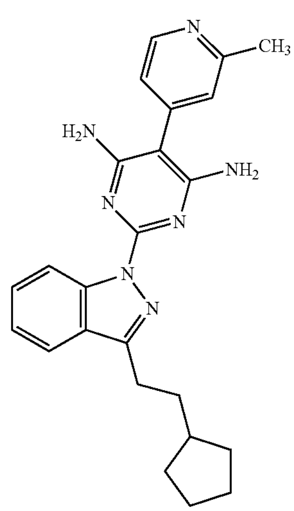 [SMILES: Cc1cc(-c2c(N)nc(-n3nc(CCC4CCCC4)c4ccccc43)nc2N)ccn1] | 1.08 | 414.1 | B |

TABLE 9-continued

| Example | Structure | Retention time (min) | m/z (M + 1) | LC Method |
|---|---|---|---|---|
| 211 | 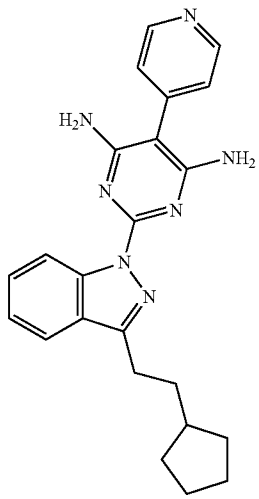 [SMILES: Nc1nc(-n2nc(CCC3CCCC3)c3ccccc32)nc(N)c1-c1ccncc1] | 1.08 | 400.1 | B |
| 212 | 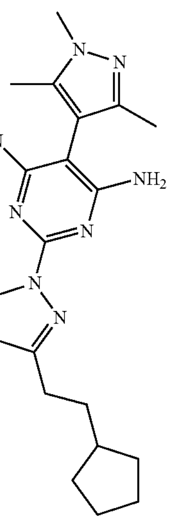 | 1.13 | 431.2 | B |
| 213 | 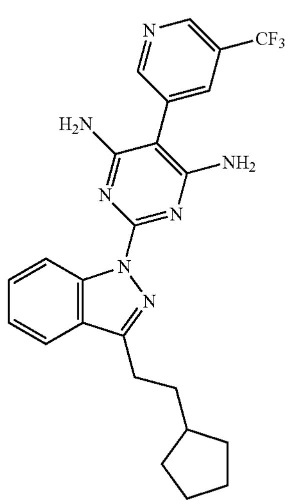 [SMILES: Nc1nc(-n2nc(CCC3CCCC3)c3ccccc32)nc(N)c1-c1cncc(C(F)(F)F)c1] | 1.16 | 468.1 | B |

TABLE 9-continued

| Example | Structure | Retention time (min) | m/z (M + 1) | LC Method |
|---|---|---|---|---|
| 214 | 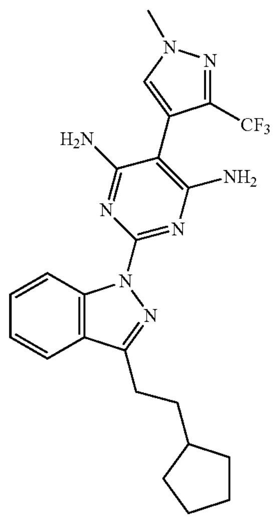 [SMILES: Cn1cc(-c2c(N)nc(-n3nc(CCC4CCCC4)c4ccccc43)nc2N)c(C(F)(F)F)n1] | 1.13 | 537.1 | B |
| 215 | 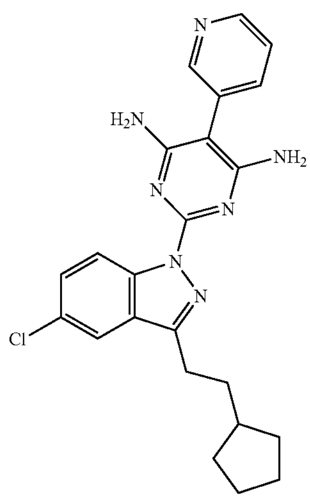 [SMILES: Nc1nc(-n2nc(CCC3CCCC3)c3cc(Cl)ccc32)nc(N)c1-c1cccnc1] | 1.13 | 434.03 | B |
| 216 | 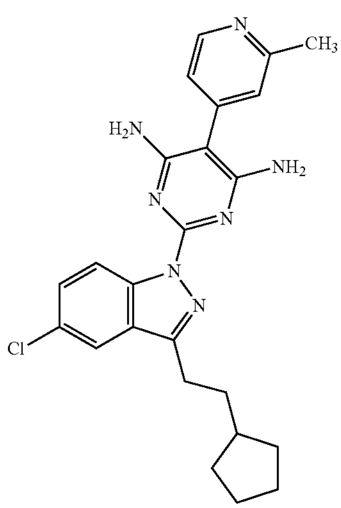 [SMILES: Cc1cc(-c2c(N)nc(-n3nc(CCC4CCCC4)c4cc(Cl)ccc43)nc2N)ccn1] | 1.13 | 448.04 | B |

TABLE 9-continued

| Example | Structure | Retention time (min) | m/z (M + 1) | LC Method |
|---------|-----------|----------------------|-------------|-----------|
| 217 | 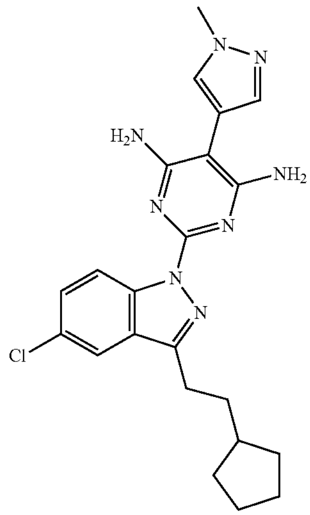 [SMILES: Cn1cc(-c2c(N)nc(-n3nc(CCC4CCCC4)c4cc(Cl)ccc43)nc2N)cn1] | 1.16 | 483.1 | B |
| 218 | 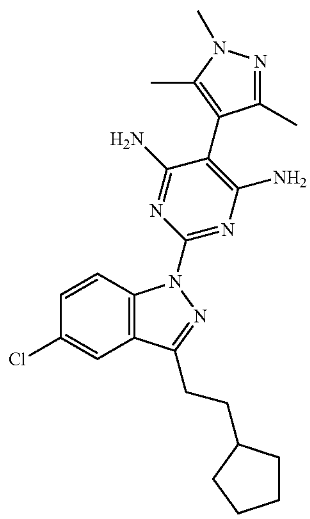 [SMILES: Cc1nn(C)c(C)c1-c1c(N)nc(-n2nc(CCC3CCCC3)c3cc(Cl)ccc32)nc1N] | 1.17 | 465.1 | B |
| 219 | 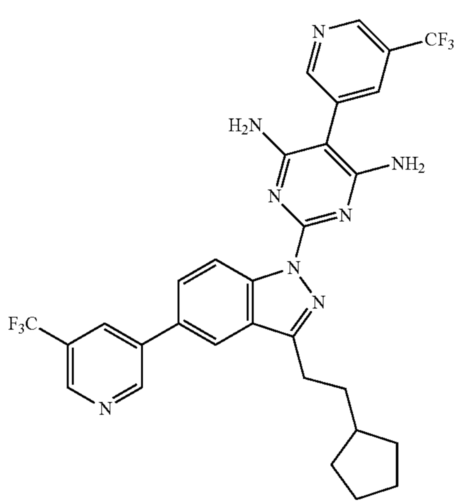 [SMILES: Nc1nc(-n2nc(CCC3CCCC3)c3cc(-c4cncc(C(F)(F)F)c4)ccc32)nc(N)c1-c1cncc(C(F)(F)F)c1] | 1.21 | 613.1 | B |

TABLE 9-continued

| Example | Structure | Retention time (min) | m/z (M + 1) | LC Method |
|---|---|---|---|---|
| 220 | 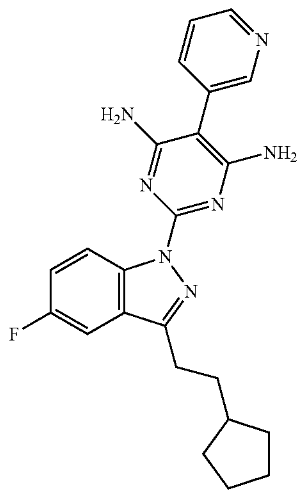 [SMILES: Nc1nc(-n2nc(CCC3CCCC3)c3cc(F)ccc32)nc(N)c1-c1cccnc1] | 1.15 | 418.2 | B |
| 221 | 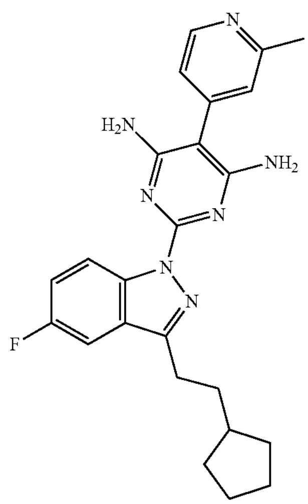 [SMILES: Cc1cc(-c2c(N)nc(-n3nc(CCC4CCCC4)c4cc(F)ccc43)nc2N)ccn1] | 1.13 | 432.1 | B |
| 222 | 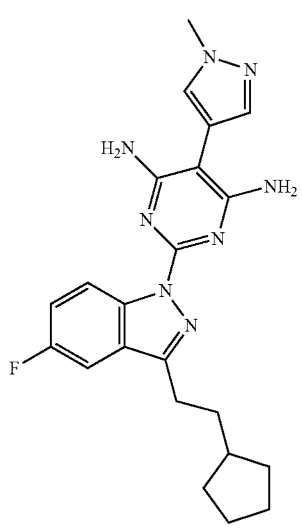 [SMILES: Cn1cc(-c2c(N)nc(-n3nc(CCC4CCCC4)c4cc(F)ccc43)nc2N)cn1] | 1.15 | 421.2 | B |

TABLE 9-continued

| Example | Structure | Retention time (min) | m/z (M + 1) | LC Method |
|---|---|---|---|---|
| 223 | 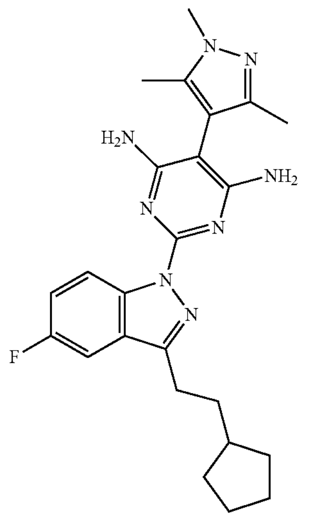 [SMILES: Cc1nn(C)c(C)c1-c1c(N)nc(-n2nc(CCC3CCCC3)c3cc(F)ccc32)nc1N] | 1.16 | 449.3 | B |
| 224 | 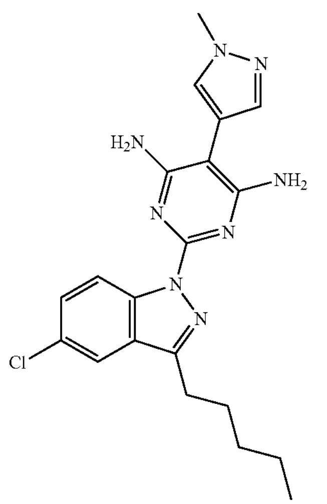 [SMILES: CCCCCc1nn(-c2nc(N)c(-c3cnn(C)c3)c(N)n2)c2ccc(Cl)cc12] | 1.85 | 411 | C |
| 225 | 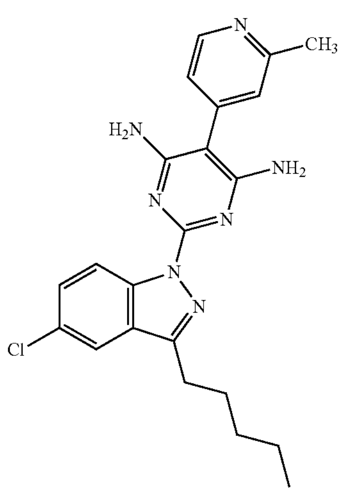 [SMILES: CCCCCc1nn(-c2nc(N)c(-c3ccnc(C)c3)c(N)n2)c2ccc(Cl)cc12] | 1.73 | 422.04 | C |

TABLE 9-continued

| Example | Structure | Retention time (min) | m/z (M + 1) | LC Method |
|---|---|---|---|---|
| 226 | 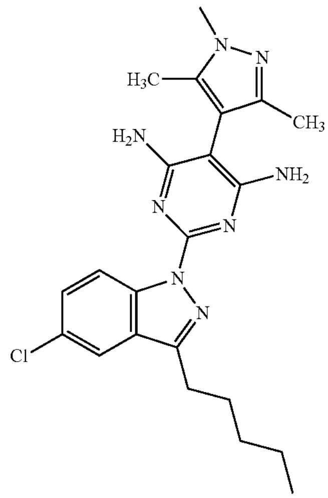 [SMILES: CCCCCc1nn(-c2nc(N)c(-c3c(C)nn(C)c3C)c(N)n2)c2ccc(Cl)cc12] | 1.89 | 439.05 | C |
| 227 | 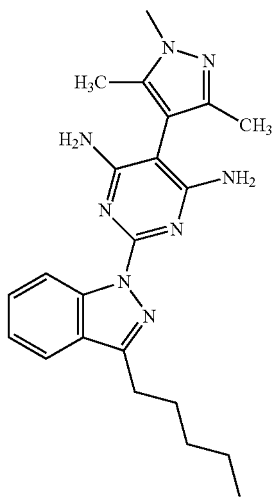 [SMILES: CCCCCc1nn(-c2nc(N)c(-c3c(C)nn(C)c3C)c(N)n2)c2ccccc12] | 1.12 | 405.1 | B |

The chemical names of the compounds depicted in the Examples above are:

| EXAMPLE | IUPAC NAME |
|---|---|
| 2 | 2-[7-(2,3,6-trifluorobenzyl)imidazo[1,5-b]pyridazin-5-yl]-5-(1,3,5-trimethyl-1H-pyrazol-4-yl)pyrimidin-4-amine |
| 3 | 5-[1,5-dimethyl-3-(trifluoromethyl)-1H-pyrazol-4-yl]-2-[7-(2,3,6-trifluorobenzyl)imidazo[1,5-b]pyridazin-5-yl]pyrimidin-4-amine |
| 4 | 5-(2-methylpyridin-4-yl)-2-[7-(2,3,6-trifluorobenzyl)imidazo[1,5-b]pyridazin-5-yl]pyrimidin-4-amine |
| 5 | methyl {4,6-diamino-2-[7-(2,3,6-trifluorobenzyl)imidazo[1,5-b]pyridazin-5-yl]pyrimidin-5-yl}carbamate |
| 6 | methyl {4,6-diamino-2-[7-(2,3,6-trifluorobenzyl)imidazo[1,5-b]pyridazin-5-yl]pyrimidin-5-yl}methylcarbamate |
| 7 | 5-quinolin-5-yl-2-[7-(2,3,6-trifluorobenzyl)imidazo[1,5-b]pyridazin-5-yl]pyrimidin-4-amine |
| 8 | 5-pyridin-4-yl-2-[7-(2,3,6-trifluorobenzyl)imidazo[1,5-b]pyridazin-5-yl]pyrimidin-4-amine |
| 9 | 5-pyridin-3-yl-2-[7-(2,3,6-trifluorobenzyl)imidazo[1,5-b]pyridazin-5-yl]pyrimidin-4-amine |
| 10 | 2-[7-(2,3,6-trifluorobenzyl)imidazo[1,5-b]pyridazin-5-yl]-5-[5-(trifluoromethyl)pyridin-3-yl]pyrimidin-4-amine |
| 11 | 5-(5-fluoropyridin-3-yl)-2-[7-(2,3,6-trifluorobenzyl)imidazo[1,5-b]pyridazin-5-yl]pyrimidin-4-amine |

| EXAMPLE | IUPAC NAME |
|---|---|
| 12 | 5-(2-methoxypyridin-3-yl)-2-[7-(2,3,6-trifluorobenzyl)imidazo[1,5-b]pyridazin-5-yl]pyrimidin-4-amine |
| 13 | 5-(4-methylpyridin-3-yl)-2-[7-(2,3,6-trifluorobenzyl)imidazo[1,5-b]pyridazin-5-yl]pyrimidin-4-amine |
| 14 | 5-(4-methoxypyridin-3-yl)-2-[7-(2,3,6-trifluorobenzyl)imidazo[1,5-b]pyridazin-5-yl]pyrimidin-4-amine |
| 15 | 5-(1-methyl-1H-pyrazol-4-yl)-2-[7-(2,3,6-trifluorobenzyl)imidazo[1,5-b]pyridazin-5-yl]pyrimidin-4-amine |
| 16 | 5-(1-methyl-1H-pyrazol-5-yl)-2-[7-(2,3,6-trifluorobenzyl)imidazo[1,5-b]pyridazin-5-yl]pyrimidin-4-amine |
| 17 | 5-(7-fluoroquinolin-4-yl)-2-[7-(2,3,6-trifluorobenzyl)imidazo[1,5-b]pyridazin-5-yl]pyrimidin-4-amine |
| 18 | 2-[7-(2,3,6-trifluorobenzyl)imidazo[1,5-b]pyridazin-5-yl]-5-[2-(trifluoromethyl)quinolin-4-yl]pyrimidin-4-amine |
| 19 | 5-(3-fluoropyridin-4-yl)-2-[7-(2,3,6-trifluorobenzyl)imidazo[1,5-b]pyridazin-5-yl]pyrimidin-4-amine |
| 20 | 2-[7-(2,3,6-trifluorobenzyl)imidazo[1,5-b]pyridazin-5-yl]-5-[2-(trifluoromethyl)pyridin-4-yl]pyrimidin-4-amine |
| 21 | 2-[7-(2,3,6-trifluorobenzyl)imidazo[1,5-b]pyridazin-5-yl]-5-[2-(trifluoromethyl)quinolin-4-yl]pyrimidin-4-amine |
| 22 | 5-[1-methyl-3-(trifluoromethyl)-1H-pyrazol-4-yl]-2-[7-(2,3,6-trifluorobenzyl)imidazo[1,5-b]pyridazin-5-yl]pyrimidin-4-amine |
| 23 | 5-pyridin-4-yl-2-[7-(2,3,5-trifluorobenzyl)imidazo[1,5-b]pyridazin-5-yl]pyrimidin-4-amine |
| 24 | 5-pyridin-3-yl-2-[7-(2,3,5-trifluorobenzyl)imidazo[1,5-b]pyridazin-5-yl]pyrimidin-4-amine |
| 25 | 5-(4-methoxypyridin-3-yl)-2-[7-(2,3,5-trifluorobenzyl)imidazo[1,5-b]pyridazin-5-yl]pyrimidin-4-amine |
| 26 | 5-(4-methylpyridin-3-yl)-2-[7-(2,3,5-trifluorobenzyl)imidazo[1,5-b]pyridazin-5-yl]pyrimidin-4-amine |
| 27 | 5-quinolin-5-yl-2-[7-(2,3,5-trifluorobenzyl)imidazo[1,5-b]pyridazin-5-yl]pyrimidin-4-amine |
| 28 | 5-(2-methylpyridin-4-yl)-2-[7-(2,3,5-trifluorobenzyl)imidazo[1,5-b]pyridazin-5-yl]pyrimidin-4-amine |
| 29 | 2-[7-(2-chloro-3,6-difluorobenzyl)imidazo[1,5-b]pyridazin-5-yl]-5-pyridin-4-ylpyrimidin-4-amine |
| 30 | 2-[7-(2-chloro-3,6-difluorobenzyl)imidazo[1,5-b]pyridazin-5-yl]-5-(1,3,5-trimethyl-1H-pyrazol-4-yl)pyrimidin-4-amine |
| 31 | 2-[7-(2-chloro-3,6-difluorobenzyl)imidazo[1,5-b]pyridazin-5-yl]-5-(2-methylpyridin-4-yl)pyrimidin-4-amine |
| 32 | 2-[7-(2-chloro-3,6-difluorobenzyl)imidazo[1,5-b]pyridazin-5-yl]-5-quinolin-5-ylpyrimidin-4-amine |
| 33 | 2-[7-(2-chloro-3,6-difluorobenzyl)imidazo[1,5-b]pyridazin-5-yl]-5-[2-(trifluoromethyl)pyridin-4-yl]pyrimidin-4-amine |
| 34 | 2-[7-(2-chloro-3,6-difluorobenzyl)imidazo[1,5-b]pyridazin-5-yl]-5-pyridin-3-ylpyrimidin-4-amine |
| 35 | 2-[7-(2-chloro-3,6-difluorobenzyl)imidazo[1,5-b]pyridazin-5-yl]-5-(4-methoxypyridin-3-yl)pyrimidin-4-amine |
| 36 | 2-[7-(2-chloro-3,6-difluorobenzyl)imidazo[1,5-b]pyridazin-5-yl]-5-[5-(trifluoromethyl)pyridin-3-yl]pyrimidin-4-amine |
| 37 | 2-[7-(2-chloro-3,6-difluorobenzyl)imidazo[1,5-b]pyridazin-5-yl]-5-(4-methylpyridin-3-yl)pyrimidin-4-amine |
| 38 | 2-[7-(2-chloro-3,6-difluorobenzyl)imidazo[1,5-b]pyridazin-5-yl]-5-(1-methyl-1H-pyrazol-4-yl)pyrimidin-4-amine |
| 39 | 2-[7-(2-chloro-3,6-difluorobenzyl)imidazo[1,5-b]pyridazin-5-yl]-5-[1,5-dimethyl-3-(trifluoromethyl)-1H-pyrazol-4-yl]pyrimidin-4-amine |
| 40 | 2-[7-(2,3,5-trifluorobenzyl)imidazo[1,5-b]pyridazin-5-yl]-5-(1,3,5-trimethyl-1H-pyrazol-4-yl)pyrimidin-4-amine |
| 41 | 5-[1,5-dimethyl-3-(trifluoromethyl)-1H-pyrazol-4-yl]-2-[7-(2,3,5-trifluorobenzyl)imidazo[1,5-b]pyridazin-5-yl]pyrimidin-4-amine |
| 42 | 2-[7-(3-chloro-2,6-difluorobenzyl)imidazo[1,5-b]pyridazin-5-yl]-5-(1,3,5-trimethyl-1H-pyrazol-4-yl)pyrimidin-4-amine |
| 43 | 2-[7-(2,3,5-trifluorobenzyl)imidazo[1,5-b]pyridazin-5-yl]-5-[2-(trifluoromethyl)pyridin-4-yl]pyrimidin-4-amine |
| 44 | 2-[7-(2,3,5-trifluorobenzyl)imidazo[1,5-b]pyridazin-5-yl]-5-[5-(trifluoromethyl)pyridin-3-yl]pyrimidin-4-amine |
| 45 | 5-[3-(methylsulfonyl)phenyl]-2-[7-(2,3,5-trifluorobenzyl)imidazo[1,5-b]pyridazin-5-yl]pyrimidin-4-amine |
| 46 | 2-[7-(2-chloro-3,5-difluorobenzyl)imidazo[1,5-b]pyridazin-5-yl]-5-[3-(methylsulfonyl)phenyl]pyrimidin-4-amine |
| 47 | 5-[2-(methylsulfonyl)phenyl]-2-[7-(2,3,5-trifluorobenzyl)imidazo[1,5-b]pyridazin-5-yl]pyrimidin-4-amine |
| 48 | 5-[4-(methylsulfonyl)phenyl]-2-[7-(2,3,5-trifluorobenzyl)imidazo[1,5-b]pyridazin-5-yl]pyrimidin-4-amine |
| 49 | 5-(3-methoxyphenyl)-2-[7-(2,3,5-trifluorobenzyl)imidazo[1,5-b]pyridazin-5-yl]pyrimidin-4-amine |

-continued

| EXAMPLE | IUPAC NAME |
|---|---|
| 50 | 5-(2-methoxypyridin-3-yl)-2-[7-(2,3,4-trifluorobenzyl)imidazo[1,5-b]pyridazin-5-yl]pyrimidin-4-amine |
| 51 | 5-(4-methoxypyridin-3-yl)-2-[7-(2,3,4-trifluorobenzyl)imidazo[1,5-b]pyridazin-5-yl]pyrimidin-4-amine |
| 52 | 2-[7-(2,3,4-trifluorobenzyl)imidazo[1,5-b]pyridazin-5-yl]-5-[5-(trifluoromethyl)pyridin-3-yl]pyrimidin-4-amine |
| 53 | 5-pyridin-4-yl-2-[7-(2,3,4-trifluorobenzyl)imidazo[1,5-b]pyridazin-5-yl]pyrimidin-4-amine |
| 54 | 5-(1-methyl-1H-pyrazol-5-yl)-2-[7-(2,3,6-trifluorobenzyl)imidazo[1,5-b]pyridazin-5-yl]pyrimidin-4-amine |
| 55 | 5-[3-(methylsulfonyl)phenyl]-2-[7-(2,3,4-trifluorobenzyl)imidazo[1,5-b]pyridazin-5-yl]pyrimidin-4-amine |
| 56 | 2-[6-fluoro-3-(2,3,6-trifluorobenzyl)imidazo[1,5-a]pyridin-1-yl]-5-pyridin-3-ylpyrimidin-4-amine |
| 57 | 2-[6-fluoro-3-(2,3,6-trifluorobenzyl)imidazo[1,5-a]pyridin-1-yl]-5-quinolin-5-ylpyrimidin-4-amine |
| 58 | 2-[6-fluoro-3-(2,3,6-trifluorobenzyl)imidazo[1,5-a]pyridin-1-yl]-5-pyridin-4-ylpyrimidin-4-amine |
| 59 | 2-[6-fluoro-3-(2,3,6-trifluorobenzyl)imidazo[1,5-a]pyridin-1-yl]-5-(1,3,5-trimethyl-1H-pyrazol-4-yl)pyrimidin-4-amine |
| 60 | 2-[6-fluoro-3-(2,3,6-trifluorobenzyl)imidazo[1,5-a]pyridin-1-yl]-5-[5-(trifluoromethyl)pyridin-3-yl]pyrimidin-4-amine |
| 61 | 5-(5-fluoropyridin-3-yl)-2-[6-fluoro-3-(2,3,6-trifluorobenzyl)imidazo[1,5-a]pyridin-1-yl]pyrimidin-4-amine |
| 62 | 2-[6-fluoro-3-(2,3,6-trifluorobenzyl)imidazo[1,5-a]pyridin-1-yl]-5-(2-methoxypyridin-3-yl)pyrimidin-4-amine |
| 63 | 2-[6-fluoro-3-(2,3,6-trifluorobenzyl)imidazo[1,5-a]pyridin-1-yl]-5-(4-methylpyridin-3-yl)pyrimidin-4-amine |
| 64 | 2-[6-fluoro-3-(2,3,6-trifluorobenzyl)imidazo[1,5-a]pyridin-1-yl]-5-(2-methylpyridin-4-yl)pyrimidin-4-amine |
| 65 | 2-[6-fluoro-3-(2,3,6-trifluorobenzyl)imidazo[1,5-a]pyridin-1-yl]-5-(4-methoxypyridin-3-yl)pyrimidin-4-amine |
| 66 | 2-[6-fluoro-3-(2,3,6-trifluorobenzyl)imidazo[1,5-a]pyridin-1-yl]-5,5'-bipyrimidin-4-amine |
| 67 | 2-[6-fluoro-3-(2,3,6-trifluorobenzyl)imidazo[1,5-a]pyridin-1-yl]-5-(1-methyl-1H-pyrazol-4-yl)pyrimidin-4-amine |
| 68 | 2-[6-fluoro-3-(2,3,6-trifluorobenzyl)imidazo[1,5-a]pyridin-1-yl]-5-(1-methyl-1H-pyrazol-5-yl)pyrimidin-4-amine |
| 69 | 5-[1,5-dimethyl-3-(trifluoromethyl)-1H-pyrazol-4-yl]-2-[6-fluoro-3-(2,3,6-trifluorobenzyl)imidazo[1,5-a]pyridin-1-yl]pyrimidin-4-amine |
| 70 | 2-[6-fluoro-3-(2,3,6-trifluorobenzyl)imidazo[1,5-a]pyridin-1-yl]-5-[2-(trifluoromethyl)pyridin-4-yl]pyrimidin-4-amine |
| 71 | 5-(3-fluoropyridin-4-yl)-2-[6-fluoro-3-(2,3,6-trifluorobenzyl)imidazo[1,5-a]pyridin-1-yl]pyrimidin-4-amine |
| 72 | 2-[6-fluoro-3-(2,3,6-trifluorobenzyl)imidazo[1,5-a]pyridin-1-yl]-5-[2-(trifluoromethyl)quinolin-4-yl]pyrimidin-4-amine |
| 73 | 5-(6-fluoroquinolin-4-yl)-2-[6-fluoro-3-(2,3,6-trifluorobenzyl)imidazo[1,5-a]pyridin-1-yl]pyrimidin-4-amine |
| 74 | 2-[6-fluoro-3-(2,3,6-trifluorobenzyl)imidazo[1,5-a]pyridin-1-yl]-5-quinolin-4-ylpyrimidin-4-amine |
| 75 | 2-[6-fluoro-3-(2,3,6-trifluorobenzyl)imidazo[1,5-a]pyridin-1-yl]-5-[1-methyl-3-(trifluoromethyl)-1H-pyrazol-4-yl]pyrimidin-4-amine |
| 76 | 5-[5-(methoxymethyl)-1,3-dimethyl-1H-pyrazol-4-yl]-2-[7-(2,3,6-trifluorobenzyl)imidazo[1,5-b]pyridazin-5-yl]pyrimidin-4-amine |
| 77 | 2-[6-fluoro-3-(2,3,6-trifluorobenzyl)imidazo[1,5-a]pyridin-1-yl]-5-(1-methyl-1H-pyrrolo[2,3-b]pyridin-4-yl)pyrimidin-4-amine |
| 78 | 2-[6-fluoro-3-(2,3,6-trifluorobenzyl)imidazo[1,5-a]pyridin-1-yl]-5-(3-methylpyridin-4-yl)pyrimidin-4-amine |
| 79 | 2-[6-fluoro-3-(2,3,6-trifluorobenzyl)imidazo[1,5-a]pyridin-1-yl]-5-(2-methoxypyridin-4-yl)pyrimidin-4-amine |
| 80 | 5-(3,5-dimethylisoxazol-4-yl)-2-[6-fluoro-3-(2,3,6-trifluorobenzyl)imidazo[1,5-a]pyridin-1-yl]pyrimidin-4-amine |
| 81 | 2-[6-fluoro-3-(2,3,6-trifluorobenzyl)imidazo[1,5-a]pyridin-1-yl]-5-(1-methyl-1H-imidazol-5-yl)pyrimidin-4-amine |
| 82 | 2-[6-fluoro-3-(2,3,6-trifluorobenzyl)imidazo[1,5-a]pyridin-1-yl]-5-[3-(methylsulfonyl)phenyl]pyrimidin-4-amine |
| 83 | 2-[5-chloro-3-(2,3,6-trifluorobenzyl)-1H-indazol-1-yl]-5-(1-methyl-1H-pyrazol-4-yl)pyrimidine-4,6-diamine |
| 84 | 2-[5-chloro-3-(2,3,6-trifluorobenzyl)-1H-indazol-1-yl]-2'-methyl-5,5'-bipyrimidine-4,6-diamine |
| 85 | 2-[5-chloro-3-(2,3,6-trifluorobenzyl)-1H-indazol-1-yl]-5-pyridin-4-ylpyrimidine-4,6-diamine |
| 86 | 2-[5-chloro-3-(2,3,6-trifluorobenzyl)-1H-indazol-1-yl]-5-(1-isobutyl-1H-pyrazol-4-yl)pyrimidine-4,6-diamine |
| 87 | 2-[5-chloro-3-(2,3,6-trifluorobenzyl)-1H-indazol-1-yl]-5-[1-(3-methylbutyl)-1H-pyrazol-4-yl]pyrimidine-4,6-diamine |

| EXAMPLE | IUPAC NAME |
|---|---|
| 88 | 5-(1-tert-butyl-3-methyl-1H-pyrazol-4-yl)-2-[5-chloro-3-(2,3,6-trifluorobenzyl)-1H-indazol-1-yl]pyrimidine-4,6-diamine |
| 89 | 2-[5-chloro-3-(2,3,6-trifluorobenzyl)-1H-indazol-1-yl]-5-[1-(cyclopropylmethyl)-3-methyl-1H-pyrazol-4-yl]pyrimidine-4,6-diamine |
| 90 | 2-[5-chloro-3-(2,3,6-trifluorobenzyl)-1H-indazol-1-yl]-5-[5-(methoxymethyl)-1,3-dimethyl-1H-pyrazol-4-yl]pyrimidine-4,6-diamine |
| 91 | 2-[5-chloro-3-(2,3,6-trifluorobenzyl)-1H-indazol-1-yl]-5-(1,3,5-trimethyl-1H-pyrazol-4-yl)pyrimidine-4,6-diamine |
| 92 | 2-[5-chloro-3-(2,3,6-trifluorobenzyl)-1H-indazol-1-yl]-5-pyridin-3-ylpyrimidine-4,6-diamine |
| 93 | 2-[5-chloro-3-(2,3,6-trifluorobenzyl)-1H-indazol-1-yl]-5-(6-fluoropyridin-3-yl)pyrimidine-4,6-diamine |
| 94 | 2-[5-chloro-3-(2,3,6-trifluorobenzyl)-1H-indazol-1-yl]-5-[3-(methylsulfonyl)phenyl]pyrimidine-4,6-diamine |
| 95 | 2-[5-chloro-3-(2,3,6-trifluorobenzyl)-1H-indazol-1-yl]-5-(2-methylpyridin-4-yl)pyrimidine-4,6-diamine |
| 96 | 2-[5-chloro-3-(2,3,6-trifluorobenzyl)-1H-indazol-1-yl]-5-(5-fluoropyridin-3-yl)pyrimidine-4,6-diamine |
| 97 | 2-[5-chloro-3-(2,3,6-trifluorobenzyl)-1H-indazol-1-yl]-5-[1-methyl-5-(trifluoromethyl)-1H-pyrazol-4-yl]pyrimidine-4,6-diamine |
| 98 | 2-[5-chloro-3-(2,3,6-trifluorobenzyl)-1H-indazol-1-yl]-5-(5-methoxypyridin-3-yl)pyrimidine-4,6-diamine |
| 99 | 2-[5-chloro-3-(2,3,6-trifluorobenzyl)-1H-indazol-1-yl]-5-(3,5-dimethylisoxazol-4-yl)pyrimidine-4,6-diamine |
| 100 | 2-[5-chloro-3-(2,3,6-trifluorobenzyl)-1H-indazol-1-yl]-5-(2-methylpyridin-3-yl)pyrimidine-4,6-diamine |
| 101 | 2-[5-chloro-3-(2,3,6-trifluorobenzyl)-1H-indazol-1-yl]-5-(6-methylpyridin-3-yl)pyrimidine-4,6-diamine |
| 102 | 2-[5-chloro-3-(2,3,6-trifluorobenzyl)-1H-indazol-1-yl]-5-(5-methylpyridin-3-yl)pyrimidine-4,6-diamine |
| 103 | 2-[5-chloro-3-(2,3,6-trifluorobenzyl)-1H-indazol-1-yl]-5-(1-methyl-1H-pyrazol-5-yl)pyrimidine-4,6-diamine |
| 104 | 2-[5-chloro-3-(2,3,6-trifluorobenzyl)-1H-indazol-1-yl]-5-(6-methoxypyridin-3-yl)pyrimidine-4,6-diamine |
| 105 | 2-[5-chloro-3-(2,3,6-trifluorobenzyl)-1H-indazol-1-yl]-5-(2-methoxypyridin-4-yl)pyrimidine-4,6-diamine |
| 106 | 5-(2-aminopyridin-4-yl)-2-[5-chloro-3-(2,3,6-trifluorobenzyl)-1H-indazol-1-yl]pyrimidine-4,6-diamine |
| 107 | 2-[5-chloro-3-(2,3,6-trifluorobenzyl)-1H-indazol-1-yl]-5-(3,5-dimethyl-1H-pyrazol-4-yl)pyrimidine-4,6-diamine |
| 108 | methyl (4-{4,6-diamino-2-[5-chloro-3-(2,3,6-trifluorobenzyl)-1H-indazol-1-yl]pyrimidin-5-yl}pyridin-2-yl)carbamate |
| 109 | 2-[5-chloro-3-(2,3,6-trifluorobenzyl)-1H-indazol-1-yl]-5-(6-methoxypyridin-2-yl)pyrimidine-4,6-diamine |
| 110 | methyl (5-{4,6-diamino-2-[5-chloro-3-(2,3,6-trifluorobenzyl)-1H-indazol-1-yl]pyrimidin-5-yl}pyridin-2-yl)carbamate |
| 111 | 2-[5-chloro-3-(2,3,6-trifluorobenzyl)-1H-indazol-1-yl]-5-(2-methoxypyridin-3-yl)pyrimidine-4,6-diamine |
| 112 | 2-[5-chloro-3-(2,3,6-trifluorobenzyl)-1H-indazol-1-yl]-5-(3-fluoro-2-morpholin-4-ylpyridin-4-yl)pyrimidine-4,6-diamine |
| 113 | 2-[5-chloro-3-(2,3,6-trifluorobenzyl)-1H-indazol-1-yl]-5-pyrazin-2-ylpyrimidine-4,6-diamine |
| 114 | N-(5-{4,6-diamino-2-[5-chloro-3-(2,3,6-trifluorobenzyl)-1H-indazol-1-yl]pyrimidin-5-yl}pyridin-2-yl)acetamide |
| 115 | 2-[5-fluoro-3-(2,3,6-trifluorobenzyl)-1H-indazol-1-yl]-5-(2-methoxypyridin-4-yl)pyrimidine-4,6-diamine |
| 116 | 2-[5-fluoro-3-(2,3,6-trifluorobenzyl)-1H-indazol-yl]-5-[5-(trifluoromethyl)pyridin-3-yl]pyrimidine-4,6-diamine |
| 117 | 2-[5-fluoro-3-(2,3,6-trifluorobenzyl)-1H-indazol-1-yl]-5-pyridin-3-ylpyrimidine-4,6-diamine |
| 118 | 5-(6-fluoropyridin-3-yl)-2-[5-fluoro-3-(2,3,6-trifluorobenzyl)-1H-indazol-1-yl]pyrimidine-4,6-diamine |
| 119 | 5-(6-aminopyridin-3-yl)-2-[5-fluoro-3-(2,3,6-trifluorobenzyl)-1H-indazol-1-yl]pyrimidine-4,6-diamine |
| 120 | 2-[5-fluoro-3-(2,3,6-trifluorobenzyl)-1H-indazol-1-yl]-5-[3-(methylsulfonyl)phenyl]pyrimidine-4,6-diamine |
| 121 | 2-[5-fluoro-3-(2,3,6-trifluorobenzyl)-1H-indazol-1-yl]-5-quinolin-5-ylpyrimidine-4,6-diamine |
| 122 | 2-[5-fluoro-3-(2,3,6-trifluorobenzyl)-1H-indazol-1-yl]-5-(2-methylpyridin-4-yl)pyrimidine-4,6-diamine |
| 123 | 3-{4,6-diamino-2-[5-fluoro-3-(2,3,6-trifluorobenzyl)-1H-indazol-1-yl]pyrimidin-5-yl}quinolin-2-ol |
| 124 | 5-(5-fluoropyridin-3-yl)-2-[5-fluoro-3-(2,3,6-trifluorobenzyl)-1H-indazol-1-yl]pyrimidine-4,6-diamine |
| 125 | 5-(2-fluoroquinolin-3-yl)-2-[5-fluoro-3-(2,3,6-trifluorobenzyl)-1H-indazol-1-yl]pyrimidine-4,6-diamine |

| EXAMPLE | IUPAC NAME |
|---|---|
| 126 | 2-[5-fluoro-3-(2,3,6-trifluorobenzyl)-1H-indazol-1-yl]-5-pyridin-4-ylpyrimidine-4,6-diamine |
| 127 | 2-[5-fluoro-3-(2,3,6-trifluorobenzyl)-1H-indazol-1-yl]-5-(1,3,5-trimethyl-1H-pyrazol-4-yl)pyrimidine-4,6-diamine |
| 128 | 2-[5-fluoro-3-(2,3,6-trifluorobenzyl)-1H-indazol-1-yl]-5-[1-methyl-5-(trifluoromethyl)-1H-pyrazol-4-yl]pyrimidine-4,6-diamine |
| 129 | 2-[5-fluoro-3-(2,3,6-trifluorobenzyl)-1H-indazol-1-yl]-5-[1-methyl-3-(trifluoromethyl)-1H-pyrazol-5-yl]pyrimidine-4,6-diamine |
| 130 | 5-(3,5-dimethylisoxazol-4-yl)-2-[5-fluoro-3-(2,3,6-trifluorobenzyl)-1H-indazol-1-yl]pyrimidine-4,6-diamine |
| 131 | 2-[5-fluoro-3-(2,3,6-trifluorobenzyl)-1H-indazol-1-yl]-5-(2-methoxypyridin-4-yl)pyrimidine-4,6-diamine |
| 132 | 2-[5-fluoro-3-(2,3,6-trifluorobenzyl)-1H-indazol-1-yl]-2',4'-dimethoxy-5,5'-bipyrimidine-4,6-diamine |
| 133 | 2-[5-fluoro-3-(2,3,6-trifluorobenzyl)-1H-indazol-1-yl]-5-(2-methoxypyridin-3-yl)pyrimidine-4,6-diamine |
| 134 | 2-[5-fluoro-3-(2,3,6-trifluorobenzyl)-1H-indazol-1-yl]-5-(5-methoxypyridin-3-yl)pyrimidine-4,6-diamine |
| 135 | 2-[5-fluoro-3-(2,3,6-trifluorobenzyl)-1H-indazol-1-yl]-2'-methyl-5,5'-bipyrimidine-4,6-diamine |
| 136 | 2-[5-fluoro-3-(2,3,6-trifluorobenzyl)-1H-indazol-1-yl]-2'-methoxy-5,5'-bipyrimidine-4,6-diamine |
| 137 | 2-[5-fluoro-3-(2,3,6-trifluorobenzyl)-1H-indazol-1-yl]-5-(6-methoxypyridin-2-yl)pyrimidine-4,6-diamine |
| 138 | 5-(2,6-dimethoxypyridin-3-yl)-2-[5-fluoro-3-(2,3,6-trifluorobenzyl)-1H-indazol-1-yl]pyrimidine-4,6-diamine |
| 139 | 2-[5-fluoro-3-(2,3,6-trifluorobenzyl)-1H-indazol-1-yl]-5-(4-methoxypyridin-3-yl)pyrimidine-4,6-diamine |
| 140 | 2-[5-fluoro-3-(2,3,6-trifluorobenzyl)-1H-indazol-1-yl]-5,5'-bipyrimidine-4,6-diamine |
| 141 | 5-(4-fluoropyridin-3-yl)-2-[5-fluoro-3-(2,3,6-trifluorobenzyl)-1H-indazol-1-yl]pyrimidine-4,6-diamine |
| 142 | 2-[5-fluoro-3-(2,3,6-trifluorobenzyl)-1H-indazol-1-yl]-5-(1,3-thiazol-2-yl)pyrimidine-4,6-diamine |
| 143 | 2-[5-fluoro-3-(2,3,6-trifluorobenzyl)-1H-indazol-1-yl]-5-(4-methyl-2-phenyl-1,3-thiazol-5-yl)pyrimidine-4,6-diamine |
| 144 | N-{4,6-diamino-2-[5-fluoro-3-(2,3,6-trifluorobenzyl)-1H-indazol-1-yl]pyrimidin-5-yl}-2-methylpropanamide |
| 145 | 2-[5-fluoro-3-(2,3,6-trifluorobenzyl)-1H-indazol-1-yl]-5-(1,3-oxazol-2-yl)pyrimidine-4,6-diamine |
| 146 | 5-(2-methylpyridin-4-yl)-2-[3-(2,3,6-trifluorobenzyl)-1H-indazol-1-yl]pyrimidine-4,6-diamine |
| 147 | 5-(6-fluoropyridin-3-yl)-2-[3-(2,3,6-trifluorobenzyl)-1H-indazol-1-yl]pyrimidine-4,6-diamine |
| 148 | 2-[3-(2,3,6-trifluorobenzyl)-1H-indazol-1-yl]-5-(1,3,5-trimethyl-1H-pyrazol-4-yl)pyrimidine-4,6-diamine |
| 149 | 5-(5-fluoropyridin-3-yl)-2-[3-(2,3,6-trifluorobenzyl)-1H-indazol-1-yl]pyrimidine-4,6-diamine |
| 150 | 5-(1-methyl-1H-pyrazol-4-yl)-2-[3-(2,3,6-trifluorobenzyl)-1H-indazol-1-yl]pyrimidine-4,6-diamine |
| 151 | 5-(2-methylpyridin-4-yl)-2-[3-(2,3,6-trifluorobenzyl)-1H-indazol-1-yl]pyrimidine-4,6-diamine |
| 152 | 5-pyridin-4-yl-2-[3-(2,3,6-trifluorobenzyl)-1H-indazol-1-yl]pyrimidine-4,6-diamine |
| 153 | 5-pyridin-3-yl-2-[3-(2,3,6-trifluorobenzyl)-1H-indazol-1-yl]pyrimidine-4,6-diamine |
| 154 | 5-[1-methyl-5-(trifluoromethyl)-1H-pyrazol-4-yl]-2-[3-(2,3,6-trifluorobenzyl)-1H-indazol-1-yl]pyrimidine-4,6-diamine |
| 155 | 5-(2-methoxypyridin-4-yl)-2-[3-(2,3,6-trifluorobenzyl)-1H-indazol-1-yl]pyrimidine-4,6-diamine |
| 156 | 5-(3,5-dimethylisoxazol-4-yl)-2-[3-(2,3,6-trifluorobenzyl)-1H-indazol-1-yl]pyrimidine-4,6-diamine |
| 157 | 5-(2-methylpyridin-3-yl)-2-[3-(2,3,6-trifluorobenzyl)-1H-indazol-1-yl]pyrimidine-4,6-diamine |
| 158 | 5-(6-methylpyridin-3-yl)-2-[3-(2,3,6-trifluorobenzyl)-1H-indazol-1-yl]pyrimidine-4,6-diamine |
| 159 | 2'-methyl-2-[3-(2,3,6-trifluorobenzyl)-1H-indazol-1-yl]-5,5'-bipyrimidine-4,6-diamine |
| 160 | 5-(3-fluoropyridin-4-yl)-2-[3-(2,3,6-trifluorobenzyl)-1H-indazol-1-yl]pyrimidine-4,6-diamine |
| 161 | 5-[6-(dimethylamino)pyridin-3-yl]-2-[3-(2,3,6-trifluorobenzyl)-1H-indazol-1-yl]pyrimidine-4,6-diamine |
| 162 | 5-(2-methoxypyridin-3-yl)-2-[3-(2,3,6-trifluorobenzyl)-1H-indazol-1-yl]pyrimidine-4,6-diamine |
| 163 | 5-(6-methoxypyridin-3-yl)-2-[3-(2,3,6-trifluorobenzyl)-1H-indazol-1-yl]pyrimidine-4,6-diamine |

| EXAMPLE | IUPAC NAME |
|---|---|
| 164 | 5-(4-methyl-2-phenyl-1,3-thiazol-5-yl)-2-[3-(2,3,6-trifluorobenzyl)-1H-indazol-1-yl]pyrimidine-4,6-diamine |
| 165 | 5-pyrazin-2-yl-2-[3-(2,3,6-trifluorobenzyl)-1H-indazol-1-yl]pyrimidine-4,6-diamine |
| 166 | 5-(4-methoxypyridin-3-yl)-2-[3-(2,3,6-trifluorobenzyl)-1H-indazol-1-yl]pyrimidine-4,6-diamine |
| 167 | 5-(2,6-dimethoxypyridin-3-yl)-2-[3-(2,3,6-trifluorobenzyl)-1H-indazol-1-yl]pyrimidine-4,6-diamine |
| 168 | 5-(6-methoxypyridin-2-yl)-2-[3-(2,3,6-trifluorobenzyl)-1H-indazol-1-yl]pyrimidine-4,6-diamine |
| 169 | 5-pyridin-2-yl-2-[3-(2,3,6-trifluorobenzyl)-1H-indazol-1-yl]pyrimidine-4,6-diamine |
| 170 | 2-[5-methoxy-3-(2,3,6-trifluorobenzyl)-1H-indazol-1-yl]-5-(1-methyl-1H-pyrazol-4-yl)pyrimidine-4,6-diamine |
| 171 | 2-[5-methoxy-3-(2,3,6-trifluorobenzyl)-1H-indazol-1-yl]-5-pyridin-3-ylpyrimidine-4,6-diamine |
| 172 | 2-[5-methoxy-3-(2,3,6-trifluorobenzyl)-1H-indazol-1-yl]-5-[5-(trifluoromethyl)pyridin-3-yl]pyrimidine-4,6-diamine |
| 173 | 2-[5-methoxy-3-(2,3,6-trifluorobenzyl)-1H-indazol-1-yl]-5-(1,3,5-trimethyl-1H-pyrazol-4-yl)pyrimidine-4,6-diamine |
| 174 | 5-pyridin-4-yl-2-[3-(2,3,6-trifluorobenzyl)-1H-pyrazolo[4,3-b]pyridin-1-yl]pyrimidine-4,6-diamine |
| 175 | 5-(1-methyl-1H-pyrazol-4-yl)-2-[3-(2,3,6-trifluorobenzyl)-1H-pyrazolo[4,3-b]pyridin-1-yl]pyrimidine-4,6-diamine |
| 176 | methyl {4,6-diamino-2-[5-chloro-3-(2,3,6-trifluorobenzyl)-1H-indazol-1-yl]pyrimidin-5-yl}carbamate |
| 177 | methyl {4,6-diamino-2-[5-chloro-3-(2,3,6-trifluorobenzyl)-1H-indazol-1-yl]pyrimidin-5-yl}methylcarbamate |
| 178 | N-{4,6-diamino-2-[5-chloro-3-(2,3,6-trifluorobenzyl)-1H-indazol-1-yl]pyrimidin-5-yl}cyclopropanecarboxamide |
| 179 | S-methyl {4,6-diamino-2-[5-chloro-3-(2,3,6-trifluorobenzyl)-1H-indazol-1-yl]pyrimidin-5-yl}thiocarbamate |
| 180 | S-methyl {4,6-diamino-2-[5-fluoro-3-(2,3,6-trifluorobenzyl)-1H-indazol-1-yl]pyrimidin-5-yl}thiocarbamate |
| 181 | methyl {4,6-diamino-2-[5-fluoro-3-(2,3,6-trifluorobenzyl)-1H-indazol-1-yl]pyrimidin-5-yl}methylcarbamate |
| 182 | methyl {4,6-diamino-2-[3-(2,3,6-trifluorobenzyl)-1H-indazol-1-yl]pyrimidin-5-yl}carbamate |
| 183 | S-methyl {4,6-diamino-2-[3-(2,3,6-trifluorobenzyl)-1H-indazol-1-yl]pyrimidin-5-yl}thiocarbamate |
| 184 | methyl {4,6-diamino-2-[3-(2,3,6-trifluorobenzyl)-1H-indazol-1-yl]pyrimidin-5-yl}methylcarbamate |
| 185 | ethyl {4,6-diamino-2-[3-(2,3,6-trifluorobenzyl)-1H-indazol-1-yl]pyrimidin-5-yl}carbamate |
| 186 | methyl {4,6-diamino-2-[5-chloro-3-(2,3,5-trifluorobenzyl)-1H-indazol-1-yl]pyrimidin-5-yl}carbamate |
| 187 | S-methyl {4,6-diamino-2-[5-chloro-3-(2,3,5-trifluorobenzyl)-1H-indazol-1-yl]pyrimidin-5-yl}thiocarbamate |
| 188 | methyl {4,6-diamino-2-[5-chloro-3-(2,3,5-trifluorobenzyl)-1H-indazol-1-yl]pyrimidin-5-yl}methylcarbamate |
| 189 | methyl {4,6-diamino-2-[3-(2,3,5-trifluorobenzyl)-1H-indazol-1-yl]pyrimidin-5-yl}carbamate |
| 190 | methyl {4,6-diamino-2-[3-(2,3,5-trifluorobenzyl)-1H-indazol-1-yl]pyrimidin-5-yl}methylcarbamate |
| 191 | S-methyl {4,6-diamino-2-[3-(2,3,5-trifluorobenzyl)-1H-indazol-1-yl]pyrimidin-5-yl}methylthiocarbamate |
| 192 | ethyl {4,6-diamino-2-[3-(2,3,5-trifluorobenzyl)-1H-indazol-1-yl]pyrimidin-5-yl}carbamate |
| 193 | ethyl {4,6-diamino-2-[3-(2,3,5-trifluorobenzyl)-1H-indazol-1-yl]pyrimidin-5-yl}methylcarbamate |
| 194 | methyl {4,6-diamino-2-[5-phenyl-3-(2,3,6-trifluorobenzyl)-1H-indazol-1-yl]pyrimidin-5-yl}methylcarbamate |
| 195 | methyl {4,6-diamino-2-[5-fluoro-3-(2,3,5-trifluorobenzyl)-1H-indazol-1-yl]pyrimidin-5-yl}carbamate |
| 196 | methyl {4,6-diamino-2-[5-fluoro-3-(2,3,5-trifluorobenzyl)-1H-indazol-1-yl]pyrimidin-5-yl}methylcarbamate |
| 197 | ethyl {4,6-diamino-2-[5-chloro-3-(2,3,6-trifluorobenzyl)-1H-indazol-1-yl]pyrimidin-5-yl}carbamate |
| 198 | ethyl {4,6-diamino-2-[5-chloro-3-(2,3,5-trifluorobenzyl)-1H-indazol-1-yl]pyrimidin-5-yl}carbamate |
| 199 | methyl {4,6-diamino-2-[5-chloro-3-(2,3,6-trifluorobenzyl)-1H-pyrazolo[4,3-b]pyridin-1-yl]pyrimidin-5-yl}carbamate |
| 200 | methyl {4,6-diamino-2-[5-chloro-3-(2,3,6-trifluorobenzyl)-1H-pyrazolo[4,3-b]pyridin-1-yl]pyrimidin-5-yl}methylcarbamate |
| 201 | methyl {4,6-diamino-2-[3-(2,3,6-trifluorobenzyl)-1H-pyrazolo[4,3-b]pyridin-1-yl]pyrimidin-5-yl}carbamate |

| EXAMPLE | IUPAC NAME |
|---|---|
| 202 | methyl {4,6-diamino-2-[3-(3-chloro-2,5-difluorobenzyl)-5-fluoro-1H-indazol-1-yl]pyrimidin-5-yl}carbamate |
| 203 | methyl {4,6-diamino-2-[3-(2-chloro-3,6-difluorobenzyl)-5-fluoro-1H-indazol-1-yl]pyrimidin-5-yl}carbamate |
| 204 | methyl {4,6-diamino-2-[3-(2,6-difluoro-3-methylbenzyl)-5-fluoro-1H-indazol-1-yl]pyrimidin-5-yl}carbamate |
| 205 | S-methyl {4,6-diamino-2-[5-fluoro-3-(2,3,6-trichlorobenzyl)-1H-indazol-1-yl]pyrimidin-5-yl}thiocarbamate |
| 206 | N-{4,6-diamino-2-[5-fluoro-3-(2,3,6-trifluorobenzyl)-1H-indazol-1-yl]pyrimidin-5-yl}cyclopropanecarboxamide |
| 207 | N-{4,6-diamino-2-[3-(2,3,6-trifluorobenzyl)-1H-indazol-1-yl]pyrimidin-5-yl}cyclopropanecarboxamide |
| 208 | 2-[3-(2-cyclopentylethyl)-1H-indazol-1-yl]-5-pyridin-3-ylpyrimidine-4,6-diamine |
| 209 | 2-[3-(2-cyclopentylethyl)-1H-indazol-1-yl]-5-(1-methyl-1H-pyrazol-4-yl)pyrimidine-4,6-diamine |
| 210 | 2-[3-(2-cyclopentylethyl)-1H-indazol-1-yl]-5-(2-methylpyridin-4-yl)pyrimidine-4,6-diamine |
| 211 | 2-[3-(2-cyclopentylethyl)-1H-indazol-1-yl]-5-pyridin-4-ylpyrimidine-4,6-diamine |
| 212 | 2-[3-(2-cyclopentylethyl)-1H-indazol-1-yl]-5-(1,3,5-trimethyl-1H-pyrazol-4-yl)pyrimidine-4,6-diamine |
| 213 | 2-[3-(2-cyclopentylethyl)-1H-indazol-1-yl]-5-[5-(trifluoromethyl)pyridin-3-yl]pyrimidine-4,6-diamine |
| 214 | 2-[3-(2-cyclopentylethyl)-1H-indazol-1-yl]-5-[1-methyl-3-(trifluoromethyl)-1H-pyrazol-4-yl]pyrimidine-4,6-diamine |
| 215 | 2-[5-chloro-3-(2-cyclopentylethyl)-1H-indazol-1-yl]-5-pyridin-3-ylpyrimidine-4,6-diamine |
| 216 | 2-[5-chloro-3-(2-cyclopentylethyl)-1H-indazol-1-yl]-5-(2-methylpyridin-4-yl)pyrimidine-4,6-diamine |
| 217 | 2-[5-chloro-3-(2-cyclopentylethyl)-1H-indazol-1-yl]-5-(1-methyl-1H-pyrazol-4-yl)pyrimidine-4,6-diamine |
| 218 | 2-[5-chloro-3-(2-cyclopentylethyl)-1H-indazol-1-yl]-5-(1,3,5-trimethyl-1H-pyrazol-4-yl)pyrimidine-4,6-diamine |
| 219 | 2-{3-(2-cyclopentylethyl)-5-[5-(trifluoromethyl)pyridin-3-yl]-1H-indazol-1-yl}-5-[5-(trifluoromethyl)pyridin-3-yl]pyrimidine-4,6-diamine |
| 220 | 2-[3-(2-cyclopentylethyl)-5-fluoro-1H-indazol-1-yl]-5-pyridin-3-ylpyrimidine-4,6-diamine |
| 221 | 2-[3-(2-cyclopentylethyl)-5-fluoro-1H-indazol-1-yl]-5-(2-methylpyridin-4-yl)pyrimidine-4,6-diamine |
| 222 | 2-[3-(2-cyclopentylethyl)-5-fluoro-1H-indazol-1-yl]-5-(1-methyl-1H-pyrazol-4-yl)pyrimidine-4,6-diamine |
| 223 | 2-[3-(2-cyclopentylethyl)-5-fluoro-1H-indazol-1-yl]-5-(1,3,5-trimethyl-1H-pyrazol-4-yl)pyrimidine-4,6-diamine |
| 224 | 2-(5-chloro-3-pentyl-1H-indazol-1-yl)-5-(1-methyl-1H-pyrazol-4-yl)pyrimidine-4,6-diamine |
| 225 | 2-(5-chloro-3-pentyl-1H-indazol-1-yl)-5-(2-methylpyridin-4-yl)pyrimidine-4,6-diamine |
| 226 | 2-(5-chloro-3-pentyl-1H-indazol-1-yl)-5-(1,3,5-trimethyl-1H-pyrazol-4-yl)pyrimidine-4,6-diamine |
| 227 | 2-(3-pentyl-1H-indazol-1-yl)-5-(1,3,5-trimethyl-1H-pyrazol-4-yl)pyrimidine-4,6-diamine |

Cell-based sGC Functional Assay (CASA Assay)

Rationale: sGC is a heme-containing enzyme that converts GTP to secondary messenger cGMP. Increases in cGMP levels affect several physiological processes including vasorelaxation through multiple downstream pathways. The rate by which sGC catalyzes cGMP formation is greatly increased by NO and by recently discovered NO-independent activators and stimulators. Heme-dependent activators (HDAs) preferentially activate sGC containing a ferrous Deme group. To determine the effect of sGC activators on enzyme activity, the CASA assay was developed to monitor the generation of cGMP in a cell line that stably expresses the heterodimeric sGC protein.

Methods: A CHO-K1 cell line stably expressing the sGC α1/β1 heterodimer was generated using a standard transfection protocol. CHO-K1 cells were transfected with plasmids pIREShyghsGCα1 and pIRESneo-hsGCβ1 simultaneously using FUGENE reagent. Clones that stably express both subunits were selected with hygromycin and neomycin for ~2 weeks. Clone #7 was chosen for the assay and was designated CHO-K1/sGC. CHO-K1/sGC cells were maintained in F-K12 medium containing 10% heat-inactivated Fetal Bovine Serum (FBS), 100 µg/mL penicillin/streptomycin, 0.5 mg/mL hygromycin and 0.25 mg/mL G418. On the day of the assay, cells were harvested in EBSS Assay Buffer (EAB) containing 5 mM MgCl2, 10 mM HEPES (4-(2-hydroxyethyl)piperazine-1-ethanesulfonic acid) and 0.05% BSA (bovine serum albumin) and cell density was adjusted to 2×106/mL with EAB. IBMX (3-isobutyl-1-methylxanthin, 0.5 mM) was added to inhibit degradation of cGMP. Compounds were diluted from DMSO stock solutions and added to the assay at a final DMSO concentration of 1%. Cells were incubated with compounds of the invention, in the presence and/or absence of 10 µM of 1H-(1,2,4)oxadiazolo(4,3-a) quinoxalin-1-one (ODQ), for 1 hr at 37° C. At the end of the incubation period, the reaction was terminated and the cells were lysed. The level of intracellular cGMP was determined using an HTRF-based assay kit (from CisBio, 62GM2PEC), which detects the displacement of a fluorescence labeled cGMP from its specific antibody. HTRF is a TR-FRET based technology that uses the principles of TRF and FRET. The amount of cGMP was plotted against compound concentration in PRISM software and the inflection point (IP) and maximum fold induction over DMSO control were derived from the plot.

The compounds of the instant invention had inflection points (IP) less than or equal to 10 μM and a maximum fold induction over DMSO control of at least 4-fold in the cell based assay described above (without ODQ incubation), and more particularly less than or equal to about 200 nM and equal to or greater than about 20-fold. Preferred compounds had an IP of less than or equal to about 100 nM and a maximum fold induction over DMSO control of at least 50-fold.

Cell-based assay results (without ODQ incubation) for the following representative compounds are provided. Data are listed as inflection points (IP) and the maximal fold induction over DMSO control:

| Example # | IUPAC Name | IP (nM) | Maximum fold induction over DMSO control |
|---|---|---|---|
| 3 | 5-[1,5-dimethyl-3-(trifluoromethyl)-1H-pyrazol-4-yl]-2-[7-(2,3,6-trifluorobenzyl)imidazo[1,5-b]pyridazin-5-yl]pyrimidin-4-amine | 499 | 71 |
| 4 | 5-(2-methylpyridin-4-yl)-2-[7-(2,3,6-trifluorobenzyl)imidazo[1,5-b]pyridazin-5-yl]pyrimidin-4-amine | 178 | 55 |
| 7 | 5-quinolin-5-yl-2-[7-(2,3,6-trifluorobenzyl)imidazo[1,5-b]pyridazin-5-yl]pyrimidin-4-amine | 296 | 129 |
| 56 | 2-[6-fluoro-3-(2,3,6-trifluorobenzyl)imidazo[1,5-a]pyridin-1-yl]-5-pyridin-3-ylpyrimidin-4-amine | 397 | 322 |
| 73 | 5-(6-fluoroquinolin-4-yl)-2-[6-fluoro-3-(2,3,6-trifluoro-benzyl)imidazo[1,5-a]pyridin-1-yl]pyrimidin-4-amine | 170 | 234 |
| 83 | 2-[5-chloro-3-(2,3,6-trifluoro-benzyl)-1H-indazol-1-yl]-5-(1-methyl-1H-pyrazol-4-yl)pyrimidine-4,6-diamine | 34 | 127 |
| 176 | methyl {4,6-diamino-2-[5-chloro-3-(2,3,6-trifluorobenzyl)-1H-indazol-1-yl]pyrimidin-5-yl}carbamate | 906 | 94 |
| 177 | methyl {4,6-diamino-2-[5-chloro-3-(2,3,6-trifluorobenzyl)-1H-indazol-1-yl]pyrimidin-5-yl}methylcarbamate | 194 | 137 |
| 178 | N-{4,6-diamino-2-[5-chloro-3-(2,3,6-trifluorobenzyl)-1H-indazol-1-yl]pyrimidin-5-yl} cyclopropanecarboxamide | 524 | 74 |
| 208 | 2-[3-(2-cyclopentylethyl)-1H-indazol-1-yl]-5-pyridin-3-ylpyrimidine-4,6-diamine | 540 | 244 |

While the invention has been described with reference to certain particular embodiments thereof, numerous alternative embodiments will be apparent to those skilled in the art from the teachings described herein. Recitation of a specific compound in the claims (i.e., a species) without a chiral designation is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:
1. A compound selected from the group consisting of:
1) 2-[7-(2,3,6-trifluorobenzyl)imidazo[1,5-b]pyridazin-5-yl]-5-(1,3,5-trimethyl-1H-pyrazol-4-yl)pyrimidin-4-amine,
2) 5-[1,5-dimethyl-3-(trifluoromethyl)-1H-pyrazol-4-yl]-2-[7-(2,3,6-trifluorobenzyl)imidazo[1,5-b]pyridazin-5-yl]pyrimidin-4-amine,
3) 5-(2-methylpyridin-4-yl)-2-[7-(2,3,6-trifluorobenzyl)imidazo[1,5-b]pyridazin-5-yl]pyrimidin-4-amine,
4) 5-quinolin-5-yl-2-[7-(2,3,6-trifluorobenzyl)imidazo[1,5-b]pyridazin-5-yl]pyrimidin-4-amine,
5) 5-pyridin-4-yl-2-[7-(2,3,6-trifluorobenzyl)imidazo[1,5-b]pyridazin-5-yl]pyrimidin-4-amine,
6) 5-pyridin-3-yl-2-[7-(2,3,6-trifluorobenzyl)imidazo[1,5-b]pyridazin-5-yl]pyrimidin-4-amine,
7) 2-[7-(2,3,6-trifluorobenzyl)imidazo[1,5-b]pyridazin-5-yl]-5-[5-(trifluoromethyl)pyridin-3-yl]pyrimidin-4-amine,
8) 5-(5-fluoropyridin-3-yl)-2-[7-(2,3,6-trifluorobenzyl)imidazo[1,5-b]pyridazin-5-yl]pyrimidin-4-amine,
9) 5-(2-methoxypyridin-3-yl)-2-[7-(2,3,6-trifluorobenzyl)imidazo[1,5-b]pyridazin-5-yl]pyrimidin-4-amine,
10) 5-(4-methylpyridin-3-yl)-2-[7-(2,3,6-trifluorobenzyl)imidazo[1,5-b]pyridazin-5-yl]pyrimidin-4-amine,
11) 5-(4-methoxypyridin-3-yl)-2-[7-(2,3,6-trifluorobenzyl)imidazo[1,5-b]pyridazin-5-yl]pyrimidin-4-amine,
12) 5-(1-methyl-1H-pyrazol-4-yl)-2-[7-(2,3,6-trifluorobenzyl)imidazo[1,5-b]pyridazin-5-yl]pyrimidin-4-amine,
13) 5-(1-methyl-1H-pyrazol-5-yl)-2-[7-(2,3,6-trifluorobenzyl)imidazo[1,5-b]pyridazin-5-yl]pyrimidin-4-amine,
14) 5-(7-fluoroquinolin-4-yl)-2-[7-(2,3,6-trifluorobenzyl)imidazo[1,5-b]pyridazin-5-yl]pyrimidin-4-amine,
15) 2-[7-(2,3,6-trifluorobenzyl)imidazo[1,5-b]pyridazin-5-yl]-5-[2-(trifluoromethyl)quinolin-4-yl]pyrimidin-4-amine,
16) 5-(3-fluoropyridin-4-yl)-2-[7-(2,3,6-trifluorobenzyl)imidazo[1,5-b]pyridazin-5-yl]pyrimidin-4-amine,
17) 2-[7-(2,3,6-trifluorobenzyl)imidazo[1,5-b]pyridazin-5-yl]-5-[2-(trifluoromethyl)pyridin-4-yl]pyrimidin-4-amine,
18) 2-[7-(2,3,6-trifluorobenzyl)imidazo[1,5-b]pyridazin-5-yl]-5-[2-(trifluoromethyl)quinolin-4-yl]pyrimidin-4-amine,
19) 5-[1-methyl-3-(trifluoromethyl)-1H-pyrazol-4-yl]-2-[7-(2,3,6-trifluorobenzyl)imidazo[1,5-b]pyridazin-5-yl]pyrimidin-4-amine,
20) 5-pyridin-4-yl-2-[7-(2,3,5-trifluorobenzyl)imidazo[1,5-b]pyridazin-5-yl]pyrimidin-4-amine,
21) 5-pyridin-3-yl-2-[7-(2,3,5-trifluorobenzyl)imidazo[1,5-b]pyridazin-5-yl]pyrimidin-4-amine,
22) 5-(4-methoxypyridin-3-yl)-2-[7-(2,3,5-trifluorobenzyl)imidazo[1,5-b]pyridazin-5-yl]pyrimidin-4-amine,
23) 5-(4-methylpyridin-3-yl)-2-[7-(2,3,5-trifluorobenzyl)imidazo[1,5-b]pyridazin-5-yl]pyrimidin-4-amine,
24) 5-quinolin-5-yl-2-[7-(2,3,5-trifluorobenzyl)imidazo[1,5-b]pyridazin-5-yl]pyrimidin-4-amine,
25) 5-(2-methylpyridin-4-yl)-2-[7-(2,3,5-trifluorobenzyl)imidazo[1,5-b]pyridazin-5-yl]pyrimidin-4-amine,
26) 2-[7-(2-chloro-3,6-difluorobenzyl)imidazo[1,5-b]pyridazin-5-yl]-5-pyridin-4-ylpyrimidin-4-amine,
27) 2-[7-(2-chloro-3,6-difluorobenzyl)imidazo[1,5-b]pyridazin-5-yl]-5-(1,3,5-trimethyl-1H-pyrazol-4-yl)pyrimidin-4-amine,

28) 2-[7-(2-chloro-3,6-difluorobenzyl)imidazo[1,5-b]pyridazin-5-yl]-5-(2-methylpyridin-4-yl)pyrimidin-4-amine,
29) 2-[7-(2-chloro-3,6-difluorobenzyl)imidazo[1,5-b]pyridazin-5-yl]-5-quinolin-5-ylpyrimidin-4-amine,
30) 2-[7-(2-chloro-3,6-difluorobenzyl)imidazo[1,5-b]pyridazin-5-yl]-5-[2-(trifluoromethyl)pyridin-4-yl]pyrimidin-4-amine,
31) 2-[7-(2-chloro-3,6-difluorobenzyl)imidazo[1,5-b]pyridazin-5-yl]-5-pyridin-3-ylpyrimidin-4-amine,
32) 2-[7-(2-chloro-3,6-difluorobenzyl)imidazo[1,5-b]pyridazin-5-yl]-5-(4-methoxypyridin-3-yl)pyrimidin-4-amine,
33) 2-[7-(2-chloro-3,6-difluorobenzyl)imidazo[1,5-b]pyridazin-5-yl]-5-[5-(trifluoromethyl)pyridin-3-yl]pyrimidin-4-amine,
34) 2-[7-(2-chloro-3,6-difluorobenzyl)imidazo[1,5-b]pyridazin-5-yl]-5-(4-methylpyridin-3-yl)pyrimidin-4-amine,
35) 2-[7-(2-chloro-3,6-difluorobenzyl)imidazo[1,5-b]pyridazin-5-yl]-5-(1-methyl-1H-pyrazol-4-yl)pyrimidin-4-amine,
36) 2-[7-(2-chloro-3,6-difluorobenzyl)imidazo[1,5-b]pyridazin-5-yl]-5-[1,5-dimethyl-3-(trifluoromethyl)-1H-pyrazol-4-yl]pyrimidin-4-amine,
37) 2-[7-(2,3,5-trifluorobenzyl)imidazo[1,5-b]pyridazin-5-yl]-5-(1,3,5-trimethyl-1H-pyrazol-4-yl)pyrimidin-4-amine,
38) 5-[1,5-dimethyl-3-(trifluoromethyl)-1H-pyrazol-4-yl]-2-[7-(2,3,5-trifluorobenzyl)imidazo[1,5-b]pyridazin-5-yl]pyrimidin-4-amine,
39) 2-[7-(3-chloro-2,6-difluorobenzyl)imidazo[1,5-b]pyridazin-5-yl]-5-(1,3,5-trimethyl-1H-pyrazol-4-yl)pyrimidin-4-amine,
40) 2-[7-(2,3,5-trifluorobenzyl)imidazo[1,5-b]pyridazin-5-yl]-5-[2-(trifluoromethyl)pyridin-4-yl]pyrimidin-4-amine,
41) 2-[7-(2,3,5-trifluorobenzyl)imidazo[1,5-b]pyridazin-5-yl]-5-[5-(trifluoromethyl)pyridin-3-yl]pyrimidin-4-amine,
42) 5-[3-(methylsulfonyl)phenyl]-2-[7-(2,3,5-trifluorobenzyl)imidazo[1,5-b]pyridazin-5-yl]pyrimidin-4-amine,
43) 2-[7-(2-chloro-3,5-difluorobenzyl)imidazo[1,5-b]pyridazin-5-yl]-5-[3-(methylsulfonyl)phenyl]pyrimidin-4-amine,
44) 5-[2-(methylsulfonyl)phenyl]-2-[7-(2,3,5-trifluorobenzyl)imidazo[1,5-b]pyridazin-5-yl]pyrimidin-4-amine,
45) 5-[4-(methylsulfonyl)phenyl]-2-[7-(2,3,5-trifluorobenzyl)imidazo[1,5-b]pyridazin-5-yl]pyrimidin-4-amine,
46) 5-(3-methoxyphenyl)-2-[7-(2,3,5-trifluorobenzyl)imidazo[1,5-b]pyridazin-5-yl]pyrimidin-4-amine;
47) 5-(2-methoxypyridin-3-yl)-2-[7-(2,3,4-trifluorobenzyl)imidazo[1,5-b]pyridazin-5-yl]pyrimidin-4-amine,
48) 5-(4-methoxypyridin-3-yl)-2-[7-(2,3,4-trifluorobenzyl)imidazo[1,5-b]pyridazin-5-yl]pyrimidin-4-amine,
49) 2-[7-(2,3,4-trifluorobenzyl)imidazo[1,5-b]pyridazin-5-yl]-5-[5-(trifluoromethyl)pyridin-3-yl]pyrimidin-4-amine,
50) 5-pyridin-4-yl-2-[7-(2,3,4-trifluorobenzyl)imidazo[1,5-b]pyridazin-5-yl]pyrimidin-4-amine,
51) 5-(1-methyl-1H-pyrazol-5-yl)-2-[7-(2,3,6-trifluorobenzyl)imidazo[1,5-b]pyridazin-5-yl]pyrimidin-4-amine,
52) 5-[3-(methylsulfonyl)phenyl]-2-[7-(2,3,4-trifluorobenzyl)imidazo[1,5-b]pyridazin-5-yl]pyrimidin-4-amine,
53) 2-[6-fluoro-3-(2,3,6-trifluorobenzyl)imidazo[1,5-a]pyridin-1-yl]-5-pyridin-3-ylpyrimidin-4-amine,
54) 2-[6-fluoro-3-(2,3,6-trifluorobenzyl)imidazo[1,5-a]pyridin-1-yl]-5-quinolin-5-ylpyrimidin-4-amine,
55) 2-[6-fluoro-3-(2,3,6-trifluorobenzyl)imidazo[1,5-a]pyridin-1-yl]-5-pyridin-4-ylpyrimidin-4-amine,
56) 2-[6-fluoro-3-(2,3,6-trifluorobenzyl)imidazo[1,5-a]pyridin-1-yl]-5-(1,3,5-trimethyl-1H-pyrazol-4-yl)pyrimidin-4-amine,
57) 2-[6-fluoro-3-(2,3,6-trifluorobenzyl)imidazo[1,5-a]pyridin-1-yl]-5-[5-(trifluoromethyl)pyridin-3-yl]pyrimidin-4-amine,
58) 5-(5-fluoropyridin-3-yl)-2-[6-fluoro-3-(2,3,6-trifluorobenzyl)imidazo[1,5-a]pyridin-1-yl]pyrimidin-4-amine,
59) 2-[6-fluoro-3-(2,3,6-trifluorobenzyl)imidazo[1,5-a]pyridin-1-yl]-5-(2-methoxypyridin-3-yl)pyrimidin-4-amine,
60) 2-[6-fluoro-3-(2,3,6-trifluorobenzyl)imidazo[1,5-a]pyridin-1-yl]-5-(4-methylpyridin-3-yl)pyrimidin-4-amine,
61) 2-[6-fluoro-3-(2,3,6-trifluorobenzyl)imidazo[1,5-a]pyridin-1-yl]-5-(2-methylpyridin-4-yl)pyrimidin-4-amine,
62) 2-[6-fluoro-3-(2,3,6-trifluorobenzyl)imidazo[1,5-a]pyridin-1-yl]-5-(4-methoxypyridin-3-yl)pyrimidin-4-amine,
63) 2-[6-fluoro-3-(2,3,6-trifluorobenzyl)imidazo[1,5-a]pyridin-1-yl]-5,5'-bipyrimidin-4-amine,
64) 2-[6-fluoro-3-(2,3,6-trifluorobenzyl)imidazo[1,5-a]pyridin-1-yl]-5-(1-methyl-1H-pyrazol-4-yl)pyrimidin-4-amine,
65) 2-[6-fluoro-3-(2,3,6-trifluorobenzyl)imidazo[1,5-a]pyridin-1-yl]-5-(1-methyl-1H-pyrazol-5-yl)pyrimidin-4-amine,
66) 5-[1,5-dimethyl-3-(trifluoromethyl)-1H-pyrazol-4-yl]-2-[6-fluoro-3-(2,3,6-trifluorobenzyl)imidazo[1,5-a]pyridin-1-yl]pyrimidin-4-amine,
67) 2-[6-fluoro-3-(2,3,6-trifluorobenzyl)imidazo[1,5-a]pyridin-1-yl]-5-[2-(trifluoromethyl)pyridin-4-yl]pyrimidin-4-amine,
68) 5-(3-fluoropyridin-4-yl)-2-[6-fluoro-3-(2,3,6-trifluorobenzyl)imidazo[1,5-a]pyridin-1-yl]pyrimidin-4-amine,
69) 2-[6-fluoro-3-(2,3,6-trifluorobenzyl)imidazo[1,5-a]pyridin-1-yl]-5-[2-(trifluoromethyl)quinolin-4-yl]pyrimidin-4-amine,
70) 5-(6-fluoroquinolin-4-yl)-2-[6-fluoro-3-(2,3,6-trifluorobenzyl)imidazo[1,5-a]pyridin-1-yl]pyrimidin-4-amine,
71) 2-[6-fluoro-3-(2,3,6-trifluorobenzyl)imidazo[1,5-a]pyridin-1-yl]-5-quinolin-4-ylpyrimidin-4-amine,
72) 2-[6-fluoro-3-(2,3,6-trifluorobenzyl)imidazo[1,5-a]pyridin-1-yl]-5-[1-methyl-3-(trifluoromethyl)-1H-pyrazol-4-yl]pyrimidin-4-amine,
73) 5-[5-(methoxymethyl)-1,3-dimethyl-1H-pyrazol-4-yl]-2-[7-(2,3,6-trifluorobenzyl)imidazo[1,5-b]pyridazin-5-yl]pyrimidin-4-amine,
74) 2-[6-fluoro-3-(2,3,6-trifluorobenzyl)imidazo[1,5-a]pyridin-1-yl]-5-(1-methyl-1H-pyrrolo[2,3-b]pyridin-4-yl)pyrimidin-4-amine,
75) 2-[6-fluoro-3-(2,3,6-trifluorobenzyl)imidazo[1,5-a]pyridin-1-yl]-5-(3-methylpyridin-4-yl)pyrimidin-4-amine, 76) 2-[6-fluoro-3-(2,3,6-trifluorobenzyl)imidazo[1,5-a]pyridin-1-yl]-5-(2-methoxypyridin-4-yl)pyrimidin-4-amine,
77) 5-(3,5-dimethylisoxazol-4-yl)-2-[6-fluoro-3-(2,3,6-trifluorobenzyl)imidazo[1,5-a]pyridin-1-yl]pyrimidin-4-amine,
78) 2-[6-fluoro-3-(2,3,6-trifluorobenzyl)imidazo[1,5-a]pyridin-1-yl]-5-(1-methyl-1H-imidazol-5-yl)pyrimidin-4-amine,
79) 2-[6-fluoro-3-(2,3,6-trifluorobenzyl)imidazo[1,5-a]pyridin-1-yl]-5-[3-(methylsulfonyl)phenyl]pyrimidin-4-amine,
80) 2-[5-chloro-3-(2,3,6-trifluorobenzyl)-1H-indazol-1-yl]-5-(1-methyl-1H-pyrazol-4-yl)pyrimidine-4,6-diamine,
81) 2-[5-chloro-3-(2,3,6-trifluorobenzyl)-1H-indazol-1-yl]-2'-methyl-5,5'-bipyrimidine-4,6-diamine,
82) 2-[5-chloro-3-(2,3,6-trifluorobenzyl)-1H-indazol-1-yl]-5-pyridin-4-ylpyrimidine-4,6-diamine,
83) 2-[5-chloro-3-(2,3,6-trifluorobenzyl)-1H-indazol-1-yl]-5-(1-isobutyl-1H-pyrazol-4-yl)pyrimidine-4,6-diamine,
84) 2-[5-chloro-3-(2,3,6-trifluorobenzyl)-1H-indazol-1-yl]-5-[1-(3-methylbutyl)-1H-pyrazol-4-yl]pyrimidine-4,6-diamine,
85) 5-(1-tert-butyl-3-methyl-1H-pyrazol-4-yl)-2-[5-chloro-3-(2,3,6-trifluorobenzyl)-1H-indazol-1-yl]pyrimidine-4,6-diamine,
86) 2-[5-chloro-3-(2,3,6-trifluorobenzyl)-1H-indazol-1-yl]-5-[1-(cyclopropylmethyl)-3-methyl-1H-pyrazol-4-yl]pyrimidine-4,6-diamine,
87) 2-[5-chloro-3-(2,3,6-trifluorobenzyl)-1H-indazol-1-yl]-5-[5-(methoxymethyl)-1,3-dimethyl-1H-pyrazol-4-yl]pyrimidine-4,6-diamine,
88) 2-[5-chloro-3-(2,3,6-trifluorobenzyl)-1H-indazol-1-yl]-5-(1,3,5-trimethyl-1H-pyrazol-4-yl)pyrimidine-4,6-diamine,
89) 2-[5-chloro-3-(2,3,6-trifluorobenzyl)-1H-indazol-1-yl]-5-pyridin-3-ylpyrimidine-4,6-diamine,
90) 2-[5-chloro-3-(2,3,6-trifluorobenzyl)-1H-indazol-1-yl]-5-(6-fluoropyridin-3-yl)pyrimidine-4,6-diamine,
91) 2-[5-chloro-3-(2,3,6-trifluorobenzyl)-1H-indazol-1-yl]-5-[3-(methylsulfonyl)phenyl]pyrimidine-4,6-diamine,
92) 2-[5-chloro-3-(2,3,6-trifluorobenzyl)-1H-indazol-1-yl]-5-(2-methylpyridin-4-yl)pyrimidine-4,6-diamine,
93) 2-[5-chloro-3-(2,3,6-trifluorobenzyl)-1H-indazol-1-yl]-5-(5-fluoropyridin-3-yl)pyrimidine-4,6-diamine,
94) 2-[5-chloro-3-(2,3,6-trifluorobenzyl)-1H-indazol-1-yl]-5-[1-methyl-5-(trifluoromethyl)-1H-pyrazol-4-yl]pyrimidine-4,6-diamine,
95) 2-[5-chloro-3-(2,3,6-trifluorobenzyl)-1H-indazol-1-yl]-5-(5-methoxypyridin-3-yl)pyrimidine-4,6-diamine,
96) 2-[5-chloro-3-(2,3,6-trifluorobenzyl)-1H-indazol-1-yl]-5-(3,5-dimethylisoxazol-4-yl)pyrimidine-4,6-diamine;
97) 2-[5-chloro-3-(2,3,6-trifluorobenzyl)-1H-indazol-1-yl]-5-(2-methylpyridin-3-yl)pyrimidine-4,6-diamine,
98) 2-[5-chloro-3-(2,3,6-trifluorobenzyl)-1H-indazol-1-yl]-5-(6-methylpyridin-3-yl)pyrimidine-4,6-diamine,
99) 2-[5-chloro-3-(2,3,6-trifluorobenzyl)-1H-indazol-1-yl]-5-(5-methylpyridin-3-yl)pyrimidine-4,6-diamine,
100) 2-[5-chloro-3-(2,3,6-trifluorobenzyl)-1H-indazol-1-yl]-5-(1-methyl-1H-pyrazol-5-yl)pyrimidine-4,6-diamine,
101) 2-[5-chloro-3-(2,3,6-trifluorobenzyl)-1H-indazol-1-yl]-5-(6-methoxypyridin-3-yl)pyrimidine-4,6-diamine,
102) 2-[5-chloro-3-(2,3,6-trifluorobenzyl)-1H-indazol-1-yl]-5-(2-methoxypyridin-4-yl)pyrimidine-4,6-diamine,
103) 5-(2-aminopyridin-4-yl)-2-[5-chloro-3-(2,3,6-trifluorobenzyl)-1H-indazol-1-yl]pyrimidine-4,6-diamine,
104) 2-[5-chloro-3-(2,3,6-trifluorobenzyl)-1H-indazol-1-yl]-5-(3,5-dimethyl-1H-pyrazol-4-yl)pyrimidine-4,6-diamine,
105) methyl (4-{4,6-diamino-2-[5-chloro-3-(2,3,6-trifluorobenzyl)-1H-indazol-1-yl]pyrimidin-5-yl}pyridin-2-yl)carbamate,
106) 2-[5-chloro-3-(2,3,6-trifluorobenzyl)-1H-indazol-1-yl]-5-(6-methoxypyridin-2-yl)pyrimidine-4,6-diamine,
107) methyl (5-{4,6-diamino-2-[5-chloro-3-(2,3,6-trifluorobenzyl)-1H-indazol-1-yl]pyrimidin-5-yl}pyridin-2-yl)carbamate,
108) 2-[5-chloro-3-(2,3,6-trifluorobenzyl)-1H-indazol-1-yl]-5-(2-methoxypyridin-3-yl)pyrimidine-4,6-diamine,
109) 2-[5-chloro-3-(2,3,6-trifluorobenzyl)-1H-indazol-1-yl]-5-(3-fluoro-2-morpholin-4-ylpyridin-4-yl)pyrimidine-4,6-diamine,
110) 2-[5-chloro-3-(2,3,6-trifluorobenzyl)-1H-indazol-1-yl]-5-pyrazin-2-ylpyrimidine-4,6-diamine,
111) N-(5-{4,6-diamino-2-[5-chloro-3-(2,3,6-trifluorobenzyl)-1H-indazol-1-yl]pyrimidin-5-yl}pyridin-2-yl)acetamide,
112) 2-[5-fluoro-3-(2,3,6-trifluorobenzyl)-1H-indazol-1-yl]-5-(2-methoxypyridin-4-yl)pyrimidine-4,6-diamine,
113) 2-[5-fluoro-3-(2,3,6-trifluorobenzyl)-1H-indazol-1-yl]-5-[5-(trifluoromethyl)pyridin-3-yl]pyrimidine-4,6-diamine,
114) 2-[5-fluoro-3-(2,3,6-trifluorobenzyl)-1H-indazol-1-yl]-5-pyridin-3-ylpyrimidine-4,6-diamine,
115) 5-(6-fluoropyridin-3-yl)-2-[5-fluoro-3-(2,3,6-trifluorobenzyl)-1H-indazol-1-yl]pyrimidine-4,6-diamine,
116) 5-(6-aminopyridin-3-yl)-2-[5-fluoro-3-(2,3,6-trifluorobenzyl)-1H-indazol-1-yl]pyrimidine-4,6-diamine,
117) 2-[5-fluoro-3-(2,3,6-trifluorobenzyl)-1H-indazol-1-yl]-5-[3-(methylsulfonyl)phenyl]pyrimidine-4,6-diamine,
118) 2-[5-fluoro-3-(2,3,6-trifluorobenzyl)-1H-indazol-1-yl]-5-quinolin-5-ylpyrimidine-4,6-diamine,
119) 2-[5-fluoro-3-(2,3,6-trifluorobenzyl)-1H-indazol-1-yl]-5-(2-methylpyridin-4-yl)pyrimidine-4,6-diamine,
120) 3-{4,6-diamino-2-[5-fluoro-3-(2,3,6-trifluorobenzyl)-1H-indazol-1-yl]pyrimidin-5-yl}quinolin-2-ol,
121) 5-(5-fluoropyridin-3-yl)-2-[5-fluoro-3-(2,3,6-trifluorobenzyl)-1H-indazol-1-yl]pyrimidine-4,6-diamine,
122) 5-(2-fluoroquinolin-3-yl)-2-[5-fluoro-3-(2,3,6-trifluorobenzyl)-1H-indazol-1-yl]pyrimidine-4,6-diamine,
123) 2-[5-fluoro-3-(2,3,6-trifluorobenzyl)-1H-indazol-1-yl]-5-pyridin-4-ylpyrimidine-4,6-diamine,
124) 2-[5-fluoro-3-(2,3,6-trifluorobenzyl)-1H-indazol-1-yl]-5-(1,3,5-trimethyl-1H-pyrazol-4-yl)pyrimidine-4,6-diamine,
125) 2-[5-fluoro-3-(2,3,6-trifluorobenzyl)-1H-indazol-1-yl]-5-[1-methyl-5-(trifluoromethyl)-1H-pyrazol-4-yl]pyrimidine-4,6-diamine,
126) 2-[5-fluoro-3-(2,3,6-trifluorobenzyl)-1H-indazol-1-yl]-5-[1-methyl-3-(trifluoromethyl)-1H-pyrazol-5-yl]pyrimidine-4,6-diamine,
127) 5-(3,5-dimethylisoxazol-4-yl)-2-[5-fluoro-3-(2,3,6-trifluorobenzyl)-1H-indazol-1-yl]pyrimidine-4,6-diamine,
128) 2-[5-fluoro-3-(2,3,6-trifluorobenzyl)-1H-indazol-1-yl]-5-(2-methoxypyridin-4-yl)pyrimidine-4,6-diamine,
129) 2-[5-fluoro-3-(2,3,6-trifluorobenzyl)-1H-indazol-1-yl]-2',4'-dimethoxy-5,5'-bipyrimidine-4,6-diamine, 130) 2-[5-fluoro-3-(2,3,6-trifluorobenzyl)-1H-indazol-1-yl]-5-(2-methoxypyridin-3-yl)pyrimidine-4,6-diamine,
131) 2-[5-fluoro-3-(2,3,6-trifluorobenzyl)-1H-indazol-1-yl]-5-(5-methoxypyridin-3-yl)pyrimidine-4,6-diamine,
132) 2-[5-fluoro-3-(2,3,6-trifluorobenzyl)-1H-indazol-1-yl]-2'-methyl-5,5'-bipyrimidine-4,6-diamine,
133) 2-[5-fluoro-3-(2,3,6-trifluorobenzyl)-1H-indazol-1-yl]-2'-methoxy-5,5'-bipyrimidine-4,6-diamine,
134) 2-[5-fluoro-3-(2,3,6-trifluorobenzyl)-1H-indazol-1-yl]-5-(6-methoxypyridin-2-yl)pyrimidine-4,6-diamine,
135) 5-(2,6-dimethoxypyridin-3-yl)-2-[5-fluoro-3-(2,3,6-trifluorobenzyl)-1H-indazol-1-yl]pyrimidine-4,6-diamine,
136) 2-[5-fluoro-3-(2,3,6-trifluorobenzyl)-1H-indazol-1-yl]-5-(4-methoxypyridin-3-yl)pyrimidine-4,6-diamine,
137) 2-[5-fluoro-3-(2,3,6-trifluorobenzyl)-1H-indazol-1-yl]-5,5'-bipyrimidine-4,6-diamine,
138) 5-(4-fluoropyridin-3-yl)-2-[5-fluoro-3-(2,3,6-trifluorobenzyl)-1H-indazol-1-yl]pyrimidine-4,6-diamine,
139) 2-[5-fluoro-3-(2,3,6-trifluorobenzyl)-1H-indazol-1-yl]-5-(1,3-thiazol-2-yl)pyrimidine-4,6-diamine,
140) 2-[5-fluoro-3-(2,3,6-trifluorobenzyl)-1H-indazol-1-yl]-5-(4-methyl-2-phenyl-1,3-thiazol-5-yl)pyrimidine-4,6-diamine,
141) N-{4,6-diamino-2-[5-fluoro-3-(2,3,6-trifluorobenzyl)-1H-indazol-1-yl]pyrimidin-5-yl}-2-methylpropanamide,
142) 2-[5-fluoro-3-(2,3,6-trifluorobenzyl)-1H-indazol-1-yl]-5-(1,3-oxazol-2-yl)pyrimidine-4,6-diamine,
143) 5-(2-methylpyridin-4-yl)-2-[3-(2,3,6-trifluorobenzyl)-1H-indazol-1-yl]pyrimidine-4,6-diamine,
144) 5-(6-fluoropyridin-3-yl)-2-[3-(2,3,6-trifluorobenzyl)-1H-indazol-1-yl]pyrimidine-4,6-diamine,
145) 2-[3-(2,3,6-trifluorobenzyl)-1H-indazol-1-yl]-5-(1,3,5-trimethyl-1H-pyrazol-4-yl)pyrimidine-4,6-diamine,
146) 5-(5-fluoropyridin-3-yl)-2-[3-(2,3,6-trifluorobenzyl)-1H-indazol-1-yl]pyrimidine-4,6-diamine,
147) 5-(1-methyl-1H-pyrazol-4-yl)-2-[3-(2,3,6-trifluorobenzyl)-1H-indazol-1-yl]pyrimidine-4,6-diamine,
148) 5-(2-methylpyridin-4-yl)-2-[3-(2,3,6-trifluorobenzyl)-1H-indazol-1-yl]pyrimidine-4,6-diamine,
149) 5-pyridin-4-yl-2-[3-(2,3,6-trifluorobenzyl)-1H-indazol-1-yl]pyrimidine-4,6-diamine,
150) 5-pyridin-3-yl-2-[3-(2,3,6-trifluorobenzyl)-1H-indazol-1-yl]pyrimidine-4,6-diamine,
151) 5-[1-methyl-5-(trifluoromethyl)-1H-pyrazol-4-yl]-2-[3-(2,3,6-trifluorobenzyl)-1H-indazol-1-yl]pyrimidine-4,6-diamine,
152) 5-(2-methoxypyridin-4-yl)-2-[3-(2,3,6-trifluorobenzyl)-1H-indazol-1-yl]pyrimidine-4,6-diamine,
153) 5-(3,5-dimethylisoxazol-4-yl)-2-[3-(2,3,6-trifluorobenzyl)-1H-indazol-1-yl]pyrimidine-4,6-diamine,
154) 5-(2-methylpyridin-3-yl)-2-[3-(2,3,6-trifluorobenzyl)-1H-indazol-1-yl]pyrimidine-4,6-diamine,
155) 5-(6-methylpyridin-3-yl)-2-[3-(2,3,6-trifluorobenzyl)-1H-indazol-1-yl]pyrimidine-4,6-diamine,
156) 2'-methyl-2-[3-(2,3,6-trifluorobenzyl)-1H-indazol-1-yl]-5,5'-bipyrimidine-4,6-diamine,
157) 5-(3-fluoropyridin-4-yl)-2-[3-(2,3,6-trifluorobenzyl)-1H-indazol-1-yl]pyrimidine-4,6-diamine,
158) 5-[6-(dimethylamino)pyridin-3-yl]-2-[3-(2,3,6-trifluorobenzyl)-1H-indazol-1-yl]pyrimidine-4,6-diamine,
159) 5-(2-methoxypyridin-3-yl)-2-[3-(2,3,6-trifluorobenzyl)-1H-indazol-1-yl]pyrimidine-4,6-diamine,
160) 5-(6-methoxypyridin-3-yl)-2-[3-(2,3,6-trifluorobenzyl)-1H-indazol-1-yl]pyrimidine-4,6-diamine,
161) 5-(4-methyl-2-phenyl-1,3-thiazol-5-yl)-2-[3-(2,3,6-trifluorobenzyl)-1H-indazol-1-yl]pyrimidine-4,6-diamine,
162) 5-pyrazin-2-yl-2-[3-(2,3,6-trifluorobenzyl)-1H-indazol-1-yl]pyrimidine-4,6-diamine,
163) 5-(4-methoxypyridin-3-yl)-2-[3-(2,3,6-trifluorobenzyl)-1H-indazol-1-yl]pyrimidine-4,6-diamine,
164) 5-(2,6-dimethoxypyridin-3-yl)-2-[3-(2,3,6-trifluorobenzyl)-1H-indazol-1-yl]pyrimidine-4,6-diamine,
165) 5-(6-methoxypyridin-2-yl)-2-[3-(2,3,6-trifluorobenzyl)-1H-indazol-1-yl]pyrimidine-4,6-diamine,
166) 5-pyridin-2-yl-2-[3-(2,3,6-trifluorobenzyl)-1H-indazol-1-yl]pyrimidine-4,6-diamine,
167) 2-[5-methoxy-3-(2,3,6-trifluorobenzyl)-1H-indazol-1-yl]-5-(1-methyl-1H-pyrazol-4-yl)pyrimidine-4,6-diamine,
168) 2-[5-methoxy-3-(2,3,6-trifluorobenzyl)-1H-indazol-1-yl]-5-pyridin-3-ylpyrimidine-4,6-diamine,
169) 2-[5-methoxy-3-(2,3,6-trifluorobenzyl)-1H-indazol-1-yl]-5-[5-(trifluoromethyl)pyridin-3-yl]pyrimidine-4,6-diamine,
170) 2-[5-methoxy-3-(2,3,6-trifluorobenzyl)-1H-indazol-1-yl]-5-(1,3,5-trimethyl-1H-pyrazol-4-yl)pyrimidine-4,6-diamine,
171) 5-pyridin-4-yl-2-[3-(2,3,6-trifluorobenzyl)-1H-pyrazolo[4,3-b]pyridin-1-yl]pyrimidine-4,6-diamine,
172) 5-(1-methyl-1H-pyrazol-4-yl)-2-[3-(2,3,6-trifluorobenzyl)-1H-pyrazolo[4,3-b]pyridin-1-yl]pyrimidine-4,6-diamine,
173) N-{4,6-diamino-2-[5-chloro-3-(2,3,6-trifluorobenzyl)-1H-indazol-1-yl]pyrimidin-5-yl}cyclopropanecarboxamide,
174) N-{4,6-diamino-2-[5-fluoro-3-(2,3,6-trifluorobenzyl)-1H-indazol-1-yl]pyrimidin-5-yl}cyclopropanecarboxamide,
175) N-{4,6-diamino-2-[3-(2,3,6-trifluorobenzyl)-1H-indazol-1-yl]pyrimidin-5-yl}cyclopropanecarboxamide,
176) 2-[3-(2-cyclopentylethyl)-1H-indazol-1-yl]-5-pyridin-3-ylpyrimidine-4,6-diamine,
177) 2-[3-(2-cyclopentylethyl)-1H-indazol-1-yl]-5-(1-methyl-1H-pyrazol-4-yl)pyrimidine-4,6-diamine,
178) 2-[3-(2-cyclopentylethyl)-1H-indazol-1-yl]-5-(2-methylpyridin-4-yl)pyrimidine-4,6-diamine,
179) 2-[3-(2-cyclopentylethyl)-1H-indazol-1-yl]-5-pyridin-4-ylpyrimidine-4,6-diamine,
180) 2-[3-(2-cyclopentylethyl)-1H-indazol-1-yl]-5-(1,3,5-trimethyl-1H-pyrazol-4-yl)pyrimidine-4,6-diamine,
181) 2-[3-(2-cyclopentylethyl)-1H-indazol-1-yl]-5-[5-(trifluoromethyl)pyridin-3-yl]pyrimidine-4,6-diamine,
182) 2-[3-(2-cyclopentylethyl)-1H-indazol-1-yl]-5-[1-methyl-3-(trifluoromethyl)-1H-pyrazol-4-yl]pyrimidine-4,6-diamine,
183) 2-[5-chloro-3-(2-cyclopentylethyl)-1H-indazol-1-yl]-5-pyridin-3-ylpyrimidine-4,6-diamine,
184) 2-[5-chloro-3-(2-cyclopentylethyl)-1H-indazol-1-yl]-5-(2-methylpyridin-4-yl)pyrimidine-4,6-diamine,
185) 2-[5-chloro-3-(2-cyclopentylethyl)-1H-indazol-1-yl]-5-(1-methyl-1H-pyrazol-4-yl)pyrimidine-4,6-diamine,
186) 2-[5-chloro-3-(2-cyclopentylethyl)-1H-indazol-1-yl]-5-(1,3,5-trimethyl-1H-pyrazol-4-yl)pyrimidine-4,6-diamine,
187) 2-{3-(2-cyclopentylethyl)-5-[5-(trifluoromethyl)pyridin-3-yl]-1H-indazol-1-yl}-5-[5-(trifluoromethyl)pyridin-3-yl]pyrimidine-4,6-diamine,
188) 2-[3-(2-cyclopentylethyl)-5-fluoro-1H-indazol-1-yl]-5-pyridin-3-ylpyrimidine-4,6-diamine, 189) 2-[3-(2-cyclopentylethyl)-5-fluoro-1H-indazol-1-yl]-5-(2-methylpyridin-4-yl)pyrimidine-4,6-diamine,
190) 2-[3-(2-cyclopentylethyl)-5-fluoro-1H-indazol-1-yl]-5-(1-methyl-1H-pyrazol-4-yl)pyrimidine-4,6-diamine,
191) 2-[3-(2-cyclopentylethyl)-5-fluoro-1H-indazol-1-yl]-5-(1,3,5-trimethyl-1H-pyrazol-4-yl)pyrimidine-4,6-diamine,
192) 2-(5-chloro-3-pentyl-1H-indazol-1-yl)-5-(1-methyl-1H-pyrazol-4-yl)pyrimidine-4,6-diamine,
193) 2-(5-chloro-3-pentyl-1H-indazol-1-yl)-5-(2-methylpyridin-4-yl)pyrimidine-4,6-diamine,
194) 2-(5-chloro-3-pentyl-1H-indazol-1-yl)-5-(1,3,5-trimethyl-1H-pyrazol-4-yl)pyrimidine-4,6-diamine, and
195) 2-(3-pentyl-1H-indazol-1-yl)-5-(1,3,5-trimethyl-1H-pyrazol-4-yl)pyrimidine-4,6-diamine,
or a pharmaceutically acceptable salt thereof.

2. The compound of claim 1, selected from the group consisting of:
73) 5-[5-(methoxymethyl)-1,3-dimethyl-1H-pyrazol-4-yl]-2-[7-(2,3,6-trifluorobenzyl)imidazo[1,5-b]pyridazin-5-yl]pyrimidin-4-amine,
80) 2-[5-chloro-3-(2,3,6-trifluorobenzyl)-1H-indazol-1-yl]-5-(1-methyl-1H-pyrazol-4-yl)pyrimidine-4,6-diamine,
88) 2-[5-chloro-3-(2,3,6-trifluorobenzyl)-1H-indazol-1-yl]-5-(1,3,5-trimethyl-1H-pyrazol-4-yl)pyrimidine-4,6-diamine,
89) 2-[5-chloro-3-(2,3,6-trifluorobenzyl)-1H-indazol-1-yl]-5-pyridin-3-ylpyrimidine-4,6-diamine,
90) 2-[5-chloro-3-(2,3,6-trifluorobenzyl)-1H-indazol-1-yl]-5-(6-fluoropyridin-3-yl)pyrimidine-4,6-diamine,
93) 2-[5-chloro-3-(2,3,6-trifluorobenzyl)-1H-indazol-1-yl]-5-(5-fluoropyridin-3-yl)pyrimidine-4,6-diamine,
96) 2-[5-chloro-3-(2,3,6-trifluorobenzyl)-1H-indazol-1-yl]-5-(3,5-dimethylisoxazol-4-yl)pyrimidine-4,6-diamine,
97) 2-[5-chloro-3-(2,3,6-trifluorobenzyl)-1H-indazol-1-yl]-5-(2-methylpyridin-3-yl)pyrimidine-4,6-diamine,
102) 2-[5-chloro-3-(2,3,6-trifluorobenzyl)-1H-indazol-1-yl]-5-(2-methoxypyridin-4-yl)pyrimidine-4,6-diamine,
115) 5-(6-fluoropyridin-3-yl)-2-[5-fluoro-3-(2,3,6-trifluorobenzyl)-1H-indazol-1-yl]pyrimidine-4,6-diamine,
119) 2-[5-fluoro-3-(2,3,6-trifluorobenzyl)-1H-indazol-1-yl]-5-(2-methylpyridin-4-yl)pyrimidine-4,6-diamine,
121) 5-(5-fluoropyridin-3-yl)-2-[5-fluoro-3-(2,3,6-trifluorobenzyl)-1H-indazol-1-yl]pyrimidine-4,6-diamine,
123) 2-[5-fluoro-3-(2,3,6-trifluorobenzyl)-1H-indazol-1-yl]-5-pyridin-4-ylpyrimidine-4,6-diamine,
145) 2-[3-(2,3,6-trifluorobenzyl)-1H-indazol-1-yl]-5-(1,3,5-trimethyl-1H-pyrazol-4-yl)pyrimidine-4,6-diamine,
146) 5-(5-fluoropyridin-3-yl)-2-[3-(2,3,6-trifluorobenzyl)-1H-indazol-1-yl]pyrimidine-4,6-diamine,
147) 5-(1-methyl-1H-pyrazol-4-yl)-2-[3-(2,3,6-trifluorobenzyl)-1H-indazol-1-yl]pyrimidine-4,6-diamine,
148) 5-(2-methylpyridin-4-yl)-2-[3-(2,3,6-trifluorobenzyl)-1H-indazol-1-yl]pyrimidine-4,6-diamine
149) 5-pyridin-4-yl-2-[3-(2,3,6-trifluorobenzyl)-1H-indazol-1-yl]pyrimidine-4,6-diamine,
150) 5-pyridin-3-yl-2-[3-(2,3,6-trifluorobenzyl)-1H-indazol-1-yl]pyrimidine-4,6-diamine,
151) 5-[1-methyl-5-(trifluoromethyl)-1H-pyrazol-4-yl]-2-[3-(2,3,6-trifluorobenzyl)-1H-indazol-1-yl]pyrimidine-4,6-diamine,
154) 5-(2-methylpyridin-3-yl)-2-[3-(2,3,6-trifluorobenzyl)-1H-indazol-1-yl]pyrimidine-4,6-diamine,
159) 5-(2-methoxypyridin-3-yl)-2-[3-(2,3,6-trifluorobenzyl)-1H-indazol-1-yl]pyrimidine-4,6-diamine, and
160) 5-(6-methoxypyridin-3-yl)-2-[3-(2,3,6-trifluorobenzyl)-1H-indazol-1-yl]pyrimidine-4,6-diamine,
or a pharmaceutically acceptable salt thereof.

3. A pharmaceutical composition comprising a compound of claim 1 and a pharmaceutically acceptable carrier.

4. A pharmaceutical composition comprising a compound of claim 1 and a compound selected from the group consisting of an angiotensin converting enzyme inhibitor, an angiotensin II receptor antagonist, a neutral endopeptidase inhibitor, an aldosterone antagonist, a renin inhibitor, an endothelin receptors antagonist, a vasodilator, a calcium channel blocker, a potassium channel activator, a diuretic, a sympatholitic, a beta-adrenergic blocking drug, an alpha adrenergic blocking drug, a central alpha adrenergic agonist, a peripheral vasodilator, a lipid lowering agent, and a metabolic altering agent.

* * * * *